(12) United States Patent
Khan et al.

US011078286B2

(10) Patent No.: US 11,078,286 B2
(45) Date of Patent: Aug. 3, 2021

(54) MONOCLONAL ANTIBODIES SPECIFIC FOR FIBROBLAST GROWTH FACTOR RECEPTOR 4 (FGFR4) AND METHODS OF THEIR USE

(71) Applicant: The U.S.A., as represented by the Secretary, Department of Health and Human Services, Bethesda, MD (US)

(72) Inventors: Javed Khan, Derwood, MD (US); Sivasubramanian Baskar, Ellicott City, MD (US); Rimas J. Orentas, Seattle, WA (US); Dimiter S. Dimitrov, Frederick, MD (US); Zhongyu Zhu, Frederick, MD (US); Tai Chi Cheuk, Germantown, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 160 days.

(21) Appl. No.: 15/761,398

(22) PCT Filed: Sep. 19, 2016

(86) PCT No.: PCT/US2016/052496
§ 371 (c)(1),
(2) Date: Mar. 19, 2018

(87) PCT Pub. No.: WO2017/049296
PCT Pub. Date: Mar. 23, 2017

(65) Prior Publication Data
US 2018/0318440 A1 Nov. 8, 2018

Related U.S. Application Data

(60) Provisional application No. 62/221,045, filed on Sep. 20, 2015.

(51) Int. Cl.
*C07K 16/28* (2006.01)
*A61K 47/68* (2017.01)
*A61K 47/69* (2017.01)
*A61P 35/00* (2006.01)
*A61K 39/395* (2006.01)

(52) U.S. Cl.
CPC .... *C07K 16/2863* (2013.01); *A61K 39/39558* (2013.01); *A61K 47/6803* (2017.08); *A61K 47/6849* (2017.08); *A61K 47/6911* (2017.08);

*A61P 35/00* (2018.01); *C07K 2317/622* (2013.01); *C07K 2317/77* (2013.01); *C07K 2317/92* (2013.01)

(58) Field of Classification Search
None
See application file for complete search history.

(56) References Cited

U.S. PATENT DOCUMENTS 8,071,323 B2   12/2011   Dimitrov et al.
8,337,842 B2   12/2012   Hansen
8,900,588 B2   12/2014   Floch et al.

FOREIGN PATENT DOCUMENTS

WO   WO 2014/165287 A1   9/2014

OTHER PUBLICATIONS

Dondelinger (2018) Frontiers in Immunology 9:1-15.*
Baskar et al., "FGFR4 as a potential therapeutic target for monoclonal antibody based intervention in rhabdomyosarcoma," *Cancer Res.*, vol. 75(15 Suppl) Abstract No. 2488, 2015.
Baskar et al., "Development and characterization of anti-FGFR4 monoclonal antibodies as therapeutic agents for human rhabdomyosarcoma," poster presentation, Annual Meeting of the American Association for Cancer Research, Apr. 6, 2014.
Baskar et al., "FGFR4 as therapeutic target for monoclonal antibody based on intervention in Rhabdomyosarcoma," poster presentation, Annual Meeting of the American Association for Cancer Research, Apr. 20, 2015.
GenBank Accession No. AGN91335, deposited Aug. 31, 2014.
GenBank Accession No. AFF72614, deposited Jul. 11, 2013.
Siwak et al., "The Potential of Drug-carrying Immunoliposomes as Anticancer Agents," *Clin. Cancer Res.*, vol. 8:955-956, 2002.

* cited by examiner

Primary Examiner — Michael D Pak
(74) *Attorney, Agent, or Firm* — Klarquist Sparkman, LLP

(57) ABSTRACT

Monoclonal antibodies selected from immunized mice, immunized rabbits and a human scFv library that specifically bind fibroblast growth factor receptor 4 (FGFR4) are described. Chimeric antigen receptors, antibody-drug conjugates, immunoconjugates, bispecific antibodies and immunoliposomes comprising the disclosed FGFR4-specific antibodies are also described. The antibody compositions can be used to diagnose or treat a FGFR4-positive cancer, such as rhabdomyosarcoma, lung cancer, liver cancer, breast cancer, pancreatic cancer or prostate cancer.

9 Claims, 13 Drawing Sheets
Specification includes a Sequence Listing.

MONOCLONAL ANTIBODIES SPECIFIC FOR FIBROBLAST GROWTH FACTOR RECEPTOR 4 (FGFR4) AND METHODS OF THEIR USE

CROSS REFERENCE TO RELATED APPLICATIONS

This application is the U.S. National Stage of International Application No. PCT/US2016/052496, filed Sep. 19, 2016, published in English under PCT Article 21(2), which claims the benefit of U.S. Application No. 62/221,045, filed Sep. 20, 2015, which is herein incorporated by reference in its entirety.

SEQUENCE LISTING

The amino acid sequences listed in the accompanying sequence listing are shown using standard three letter code for amino acids, as defined in 37 C.F.R. 1.822. The Sequence Listing is submitted as an ASCII text file, created on Feb. 13,2018, 104 KB, which is incorporated by reference herein. In the accompanying sequence listing:

FIELD

This disclosure concerns monoclonal antibodies that specifically bind fibroblast growth factor receptor 4 (FGFR4) and conjugates thereof. This disclosure further concerns use of the FGFR4-specific monoclonal antibodies and conjugates for the treatment of FGFR4-positive cancer.

BACKGROUND

Rhabdomyosarcoma (RMS) is the most common soft tissue sarcoma in childhood and adolescence, arising from skeletal myoblasts. There are two major subtypes of RMS—alveolar RMS (ARMS) and embryonal RMS (ERMS). With current treatment methods, relapse-free survival rates have improved to 70%-80%. However, the five-year survival rate for patients with metastatic disease remains only 30%. The main drivers of tumor progression and metastatic regulation are still unknown. It is speculated, like in most cancers, there could be many factors that are involved in metastasis. One such factor known to play a role as a metastatic regulator is fibroblast growth factor receptor 4 (FGFR4). FGFR4, a member of the FGFR gene family, is a receptor tyrosine kinase that is highly expressed in RMS.

Previous studies have associated activating mutations in FGFR4 to RMS metastasis. FGFR4 is overexpressed in both subtypes of RMS, and in ARMS, the PAX3/7-FOX01 fusion gene directly induces FGFR4 expression. High FGFR4 expression in RMS tumors is associated with advanced-stage cancer, an aggressive phenotype and poor survival. These findings suggest that FGFR4 can be further exploited as a potential therapeutic target in RMS. Recent reports have also shown overexpression of FGFR4 in several other human cancers including liver, lung, pancreas, ovary, prostate and bladder cancer.

SUMMARY

Disclosed herein are monoclonal antibodies, or antigen-binding fragments thereof, that specifically bind fibroblast growth factor receptor 4 (FGFR4). The antibodies were selected from mice and rabbits immunized with the extracellular domain of human FGFR4 (hFGFR4-ECD), and from a human scFv library. Chimeric antigen receptors, antibody-drug conjugates, immunoconjugates, bispecific antibodies, immunoliposomes and compositions comprising the FGFR4-specific antibodies are also disclosed herein. The monoclonal antibodies and antibody compositions can be used to diagnose or treat a FGFR4-positive cancer, such as rhabdomyosarcoma, lung cancer, liver cancer, breast cancer, pancreatic cancer or prostate cancer.

Provided herein are monoclonal antibodies, or antigen-binding fragments thereof, that specifically bind FGFR4. In some embodiments, the monoclonal antibodies or antigen-binding fragments comprise the VH domain and VL domain complementarity determining region (CDR) sequences of a mouse antibody selected from BT53, 3A11 and 1G5, a rabbit antibody selected from 29.2 and 57.1, or a human antibody selected from M408, M409, M410, M412, M414, M415, M417, M418, M422 and M424, as disclosed herein. Also provided herein are antibody drug conjugates (ADCs), chimeric antigen receptors (CARs), immunoconjugates, bispecific antibodies, immunoliposomes and compositions that include the FGFR4-specific monoclonal antibodies and antigen-binding fragments. Isolated cells expressing a CAR are also provided. Further provided herein are nucleic acid molecules and vectors encoding the FGFR4-specific monoclonal antibodies, antigen-binding fragments, CARs, immunoconjugates and bispecific antibodies disclosed herein.

Also provided herein is a method of inhibiting tumor growth or metastasis of a FGFR4-positive cancer by selecting a subject with a FGFR4-positive cancer and administering to the subject a therapeutically effective amount of a monoclonal antibody, antigen-binding fragment, ADC, CAR, isolated CAR-expressing cell, immunoconjugate, bispecific antibody, immunoliposome or composition disclosed herein. Further provided is a method of treating a FGFR4-positive cancer in a subject by selecting a subject with a FGFR4-positive cancer and administering to the subject a therapeutically effective amount of a monoclonal antibody, antigen-binding fragment, ADC, CAR, isolated CAR-expressing cell, immunoconjugate, bispecific antibody, immunoliposome or composition disclosed herein. In some embodiments, the FGFR-positive cancer is a rhabdomyosarcoma (RMS), such as alveolar RMS or embryonal RMS, lung cancer, liver cancer, breast cancer, pancreatic cancer or prostate cancer.

A method of detecting expression of FGFR4 in a sample (such as a biopsy sample) is also provided herein. In some embodiments, the method includes contacting the sample with a FGFR4-specific monoclonal antibody or antigen-binding fragment disclosed herein and detecting binding of the antibody or antigen-binding fragment to the sample. In some examples, the sample is obtained from a subject suspected of having a FGFR4-positive cancer.

The foregoing and other objects, features, and advantages of the invention will become more apparent from the following detailed description, which proceeds with reference to the accompanying figures.

Figure 2B:
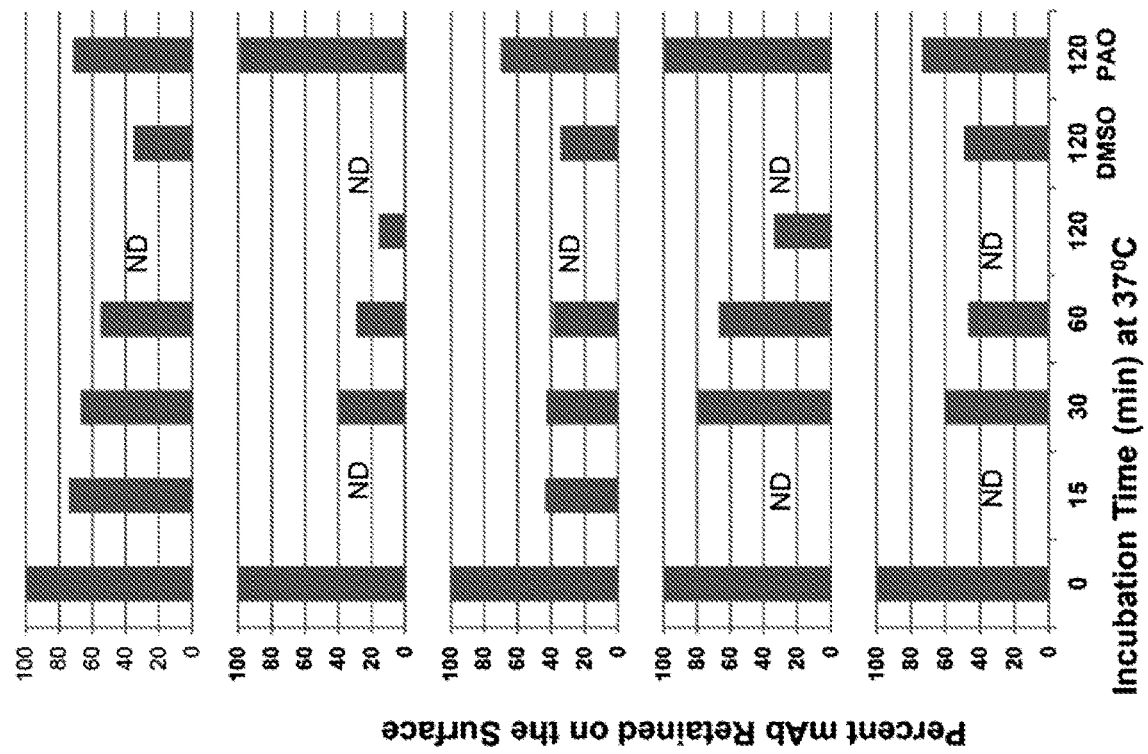
Figure 2A:
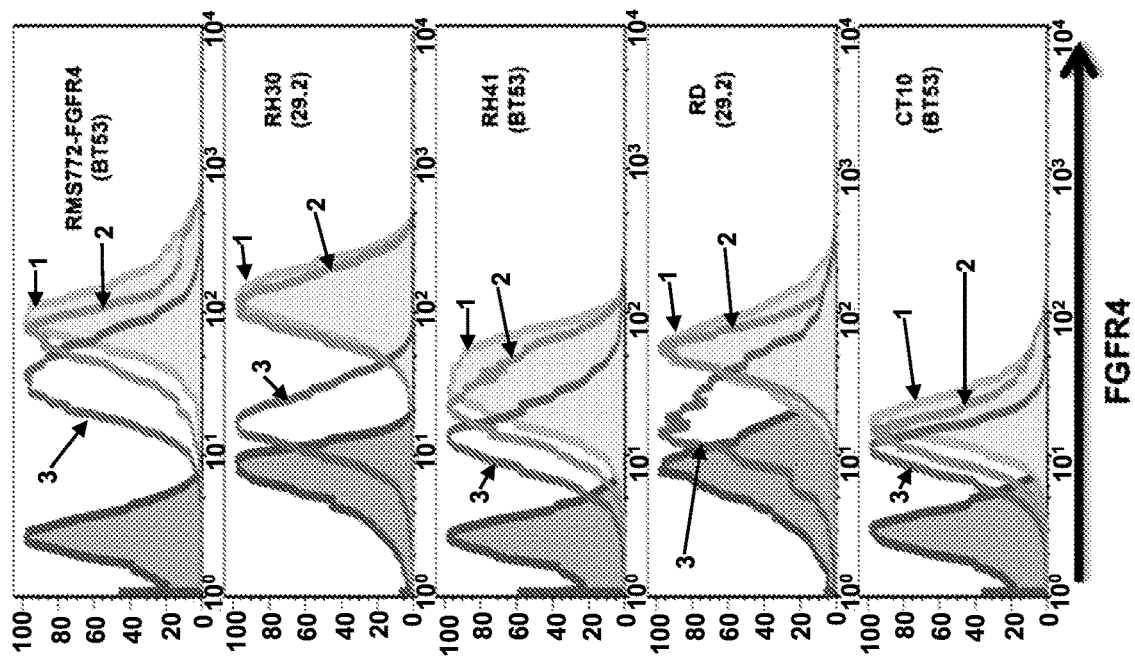

FIGS. 2A-2B show that cell surface FGFR4 facilitates rapid internalization of bound mAbs. RMS cell lines were incubated with saturating amounts of mAb 29.2 or BT53 at 40° C. After washing, the cells were maintained at 40° C. (1), or further incubated at 37° C. for the indicated time in the presence of 10 μM phenylarsine oxide (PAO) (2), or its diluent DMSO or medium only (3). Subsequently all cells were stained with fluorochrome-conjugated appropriate secondary antibody. FIG. 2A shows internalization that occurred at 2 hours in the indicated cell lines. FIG. 2B indicates the percent monoclonal antibody retained on the surface (MFI without incubation at 37° C. was set as 100%) during the time course of the experiment.

Figure 3:
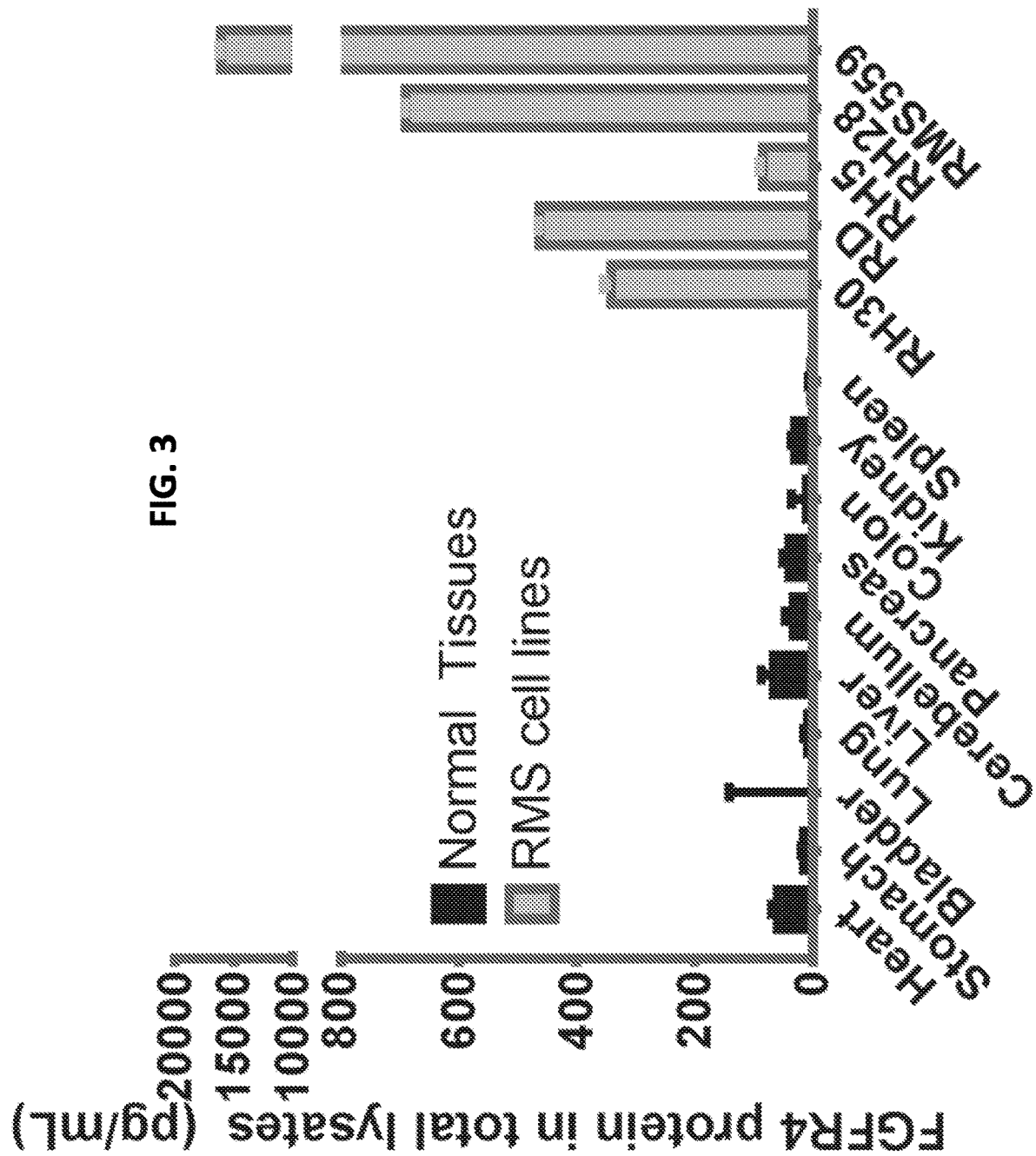

FIG. 3 is a graph showing FGFR4 protein expression in RMS cell lines is significantly higher than in normal tissues. Whole cell lysates of normal tissues and RMS cell lines were normalized to total protein concentration of 1 mg/mL and tested on Meso Scale Discovery (MSD) assay (a noncompetitive sandwich assay). A standard curve was obtained using human FGFR4 extracellular domain (ECD) protein. Samples were measured based on electrochemiluminescence signal.

Figure 4:
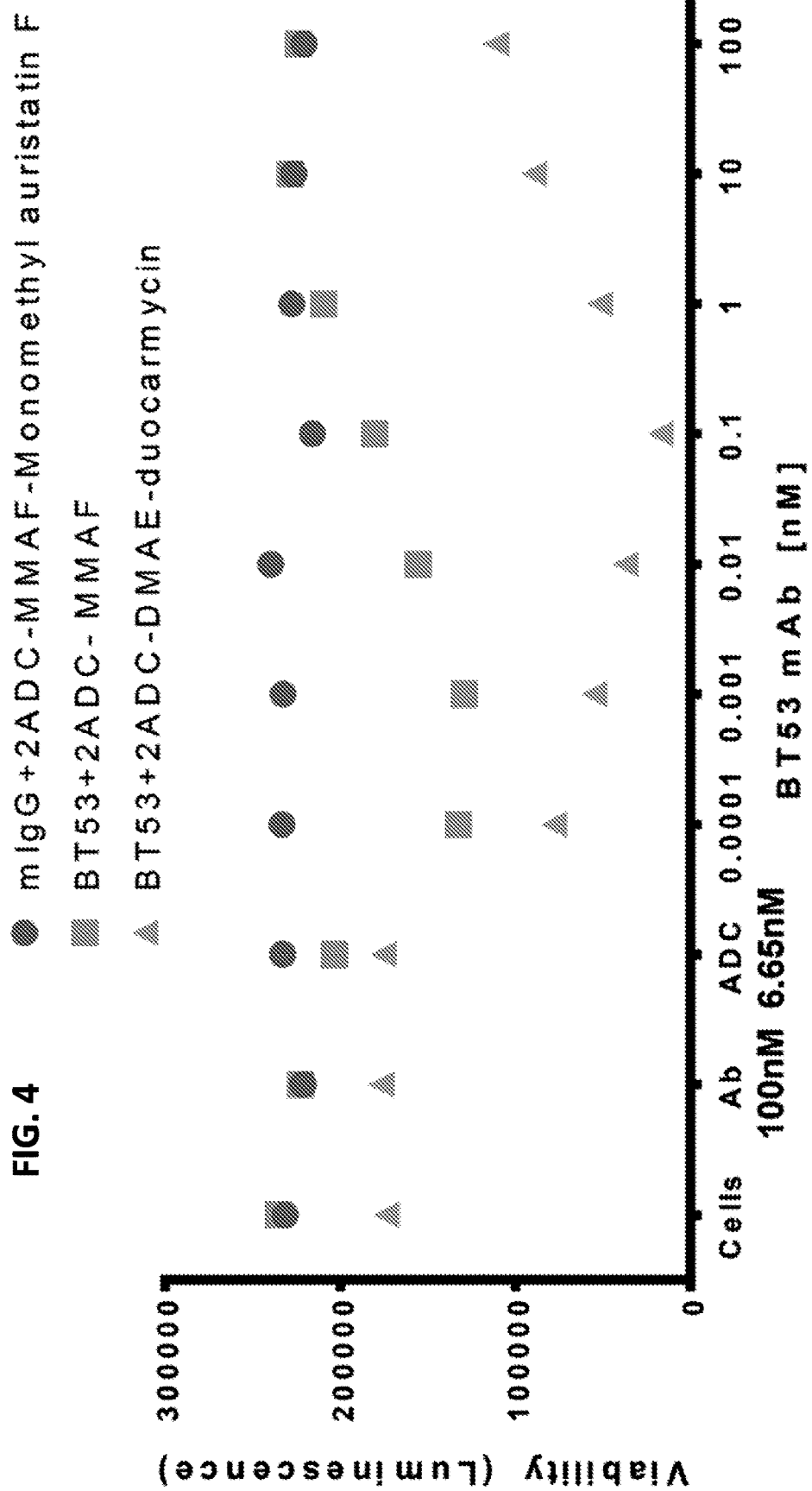

FIG. 4 is a graph showing BT53 in conjunction with secondary antibody-drug conjugate can mediate cytotoxicity in RMS cell lines. RMS cell line (RH30) was incubated with differing amounts of mIgG or BT53 mAb at the indicated concentrations. Subsequently, secondary ADC (anti-mouse-Fc-drug) was added at 6.6 nM. Dose-dependent cytotoxic activity was observed following the addition of secondary ADC. Among the two drugs tested, duocarmycin DM (DMDM) showed more potent activity than monomethyl auristatin F (MMAF).

Figure 5:
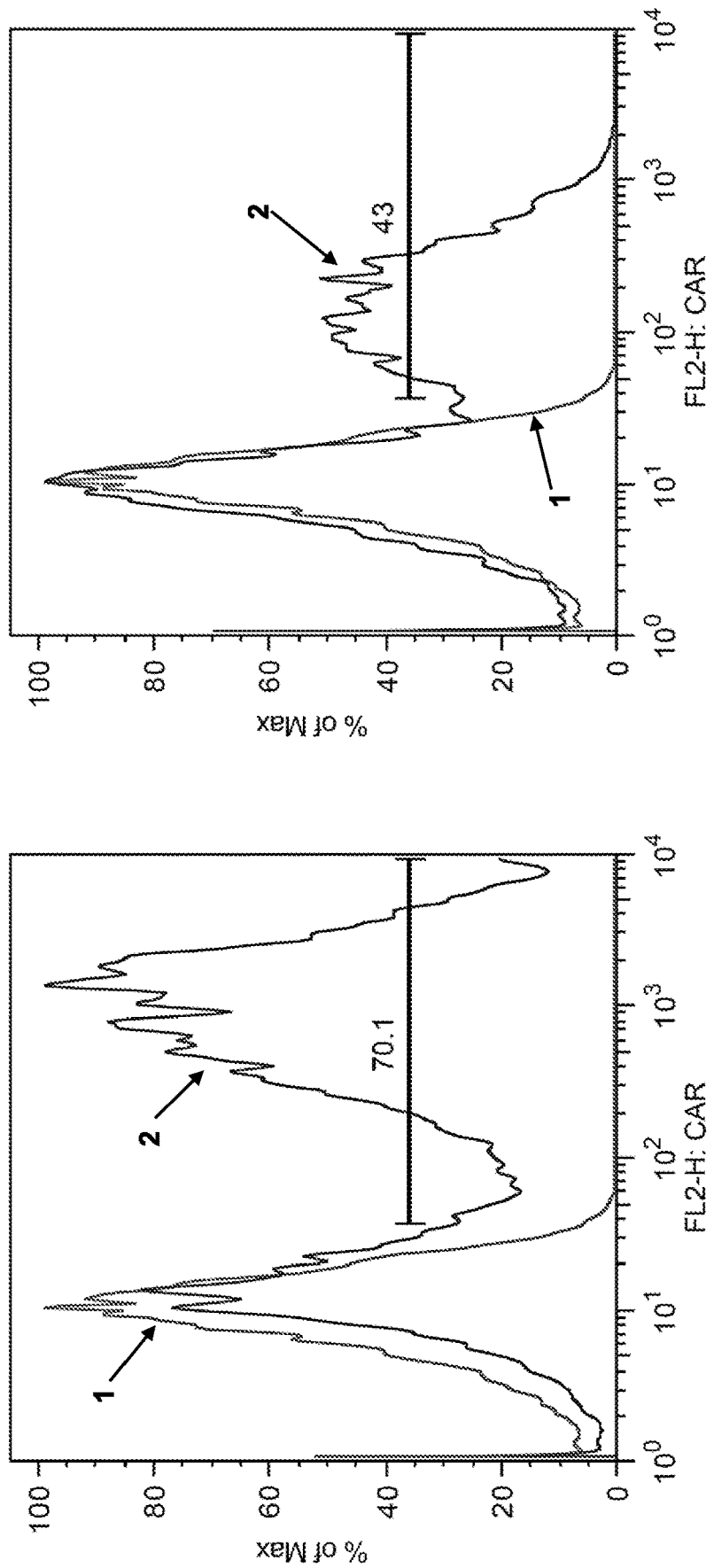

FIG. 5 is a pair of flow cytometry plots showing CAR expression in transduced T cells. Shown are expression of the FGFR4 CARs 29.2L (left) and 57.1L (right).

Figure 6:
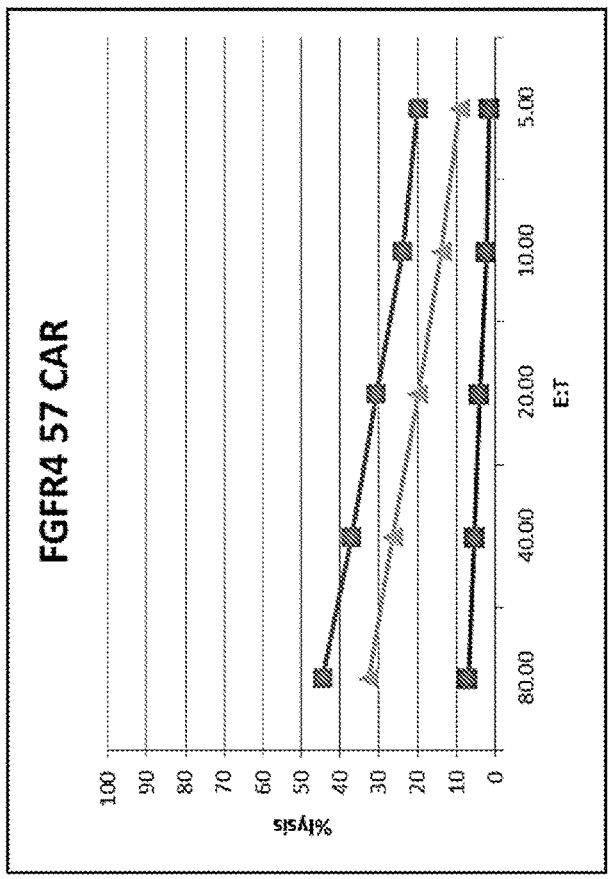
Figure 6:
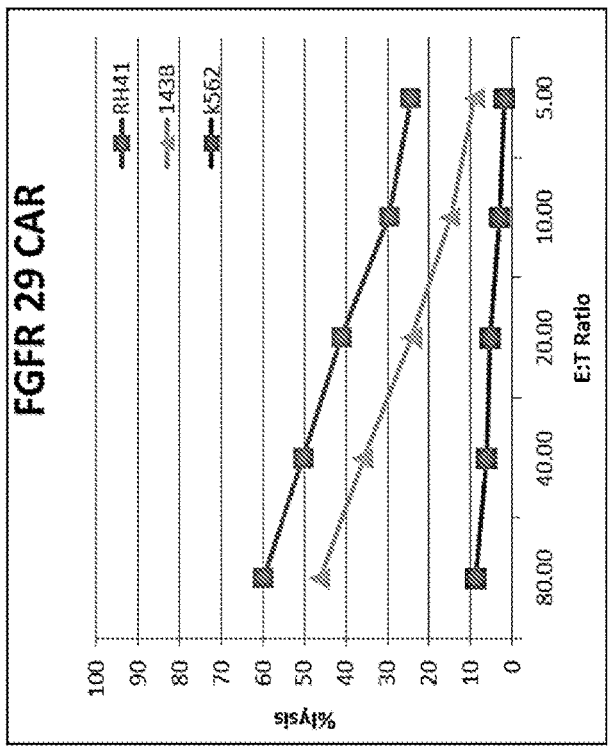
Figure 6:
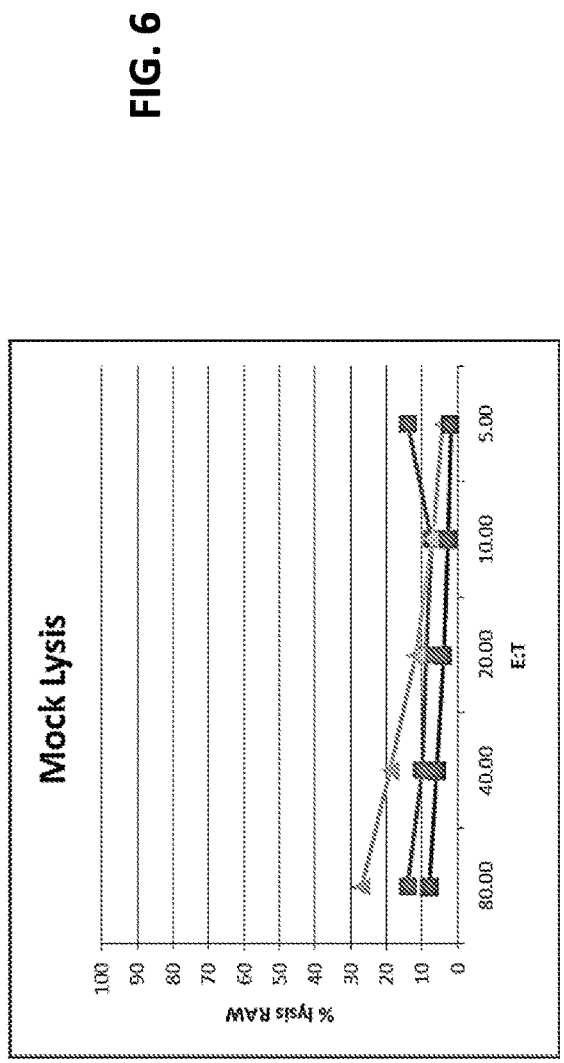

FIG. 6 is a series of graphs showing the results of cytotoxicity assays using T cells expressing the FGFR4 CARs 29.2L (left) and 57.1L. Percent lysis of rhabdomyosarcoma cells (RH41), osteosarcoma cells (143B) and myelogenous leukemia cells (K562) is shown.

Figure 7:
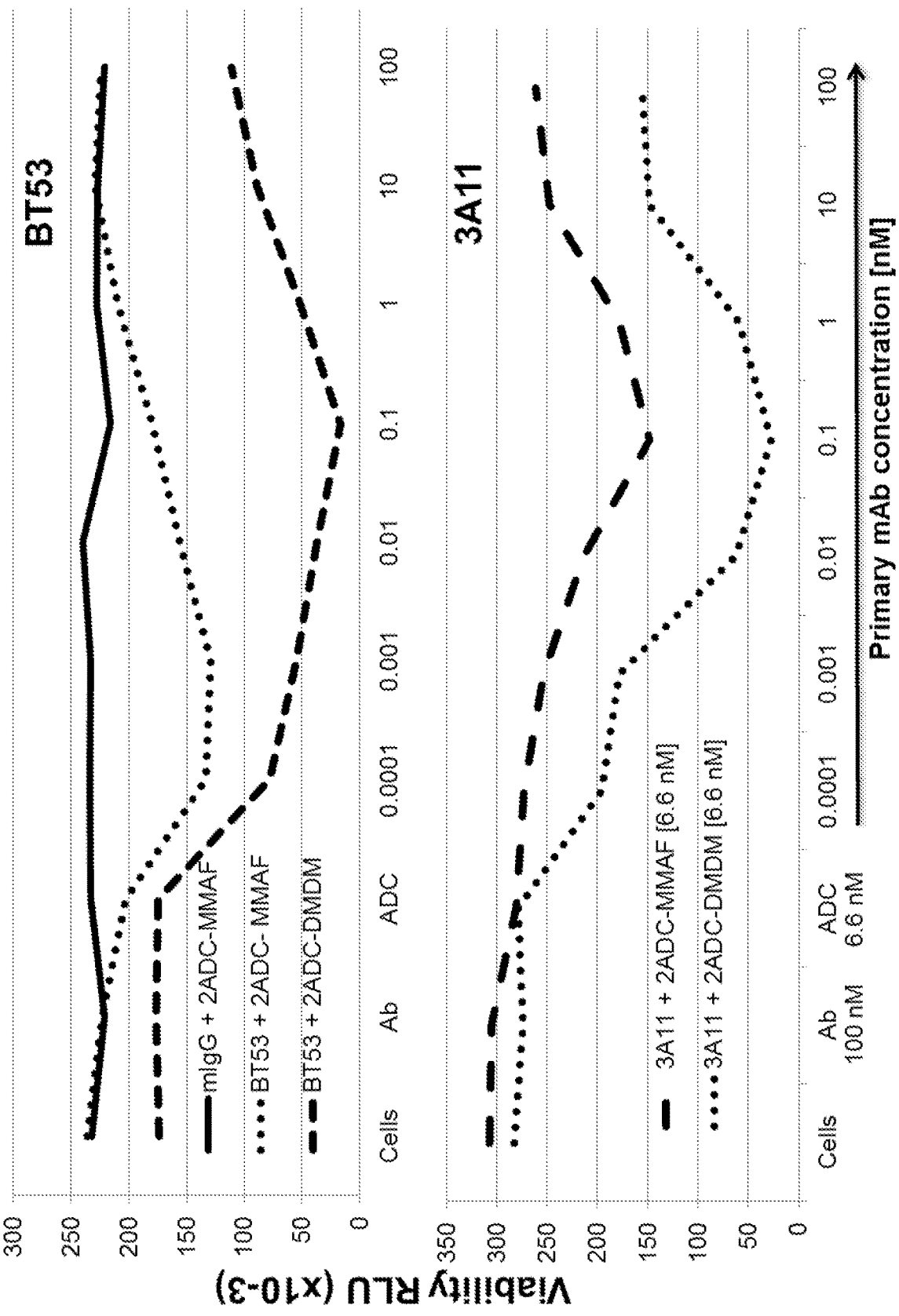

FIG. 7 is a pair of graphs showing cytotoxicity mediated by anti-FGFR4 monoclonal antibodies BT53 and 3A11 conjugated to secondary antibody-drug conjugates in the RH30 cell line.

Figure 8:
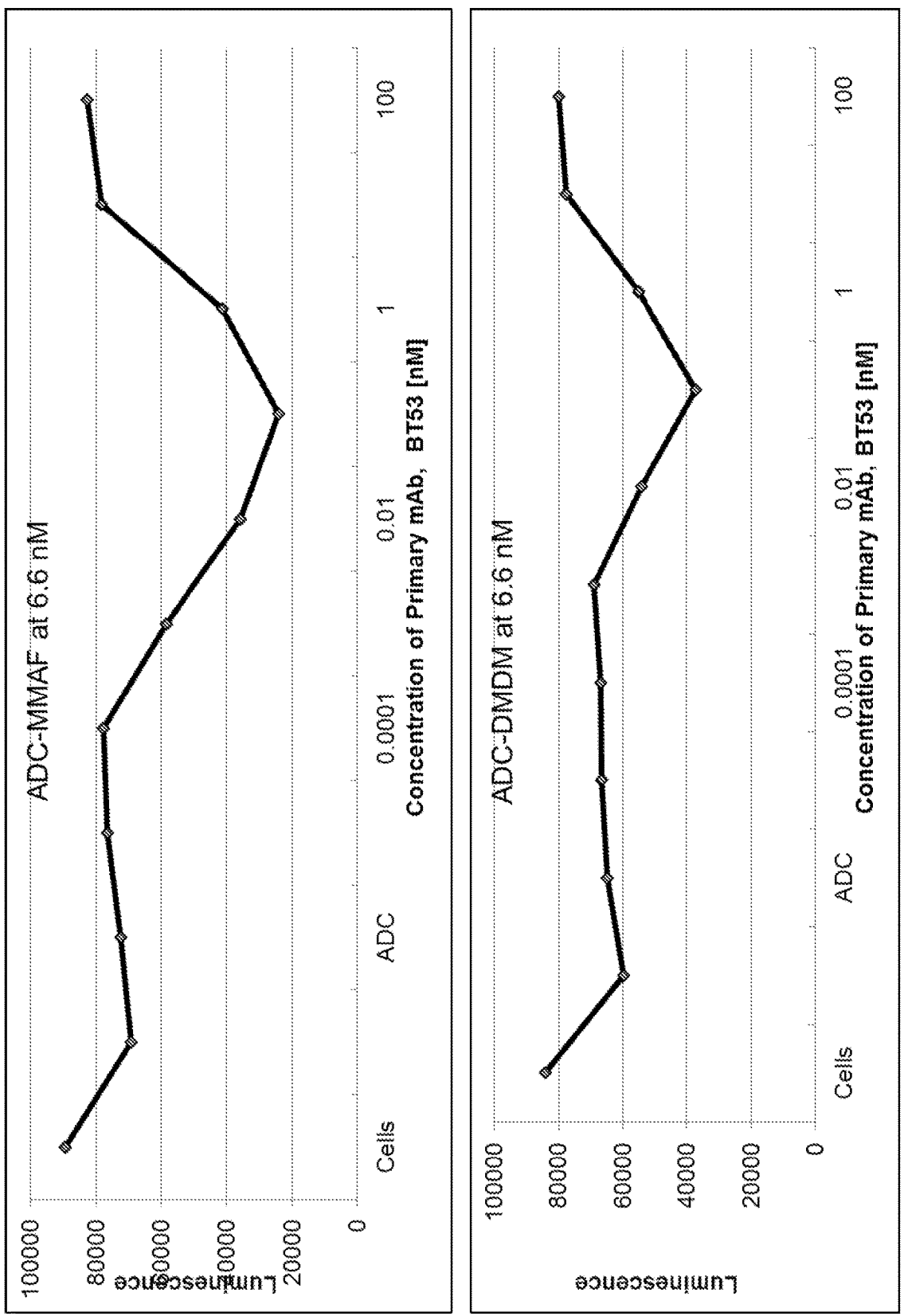

FIG. 8 is a pair of graphs showing cytotoxicity mediated by anti-FGFR4 monoclonal antibody BT53 conjugated to secondary antibody-drug conjugates (ADC-MMAF—top; ADC-DMDM—bottom) in RMS-559 cells.

Figure 9:
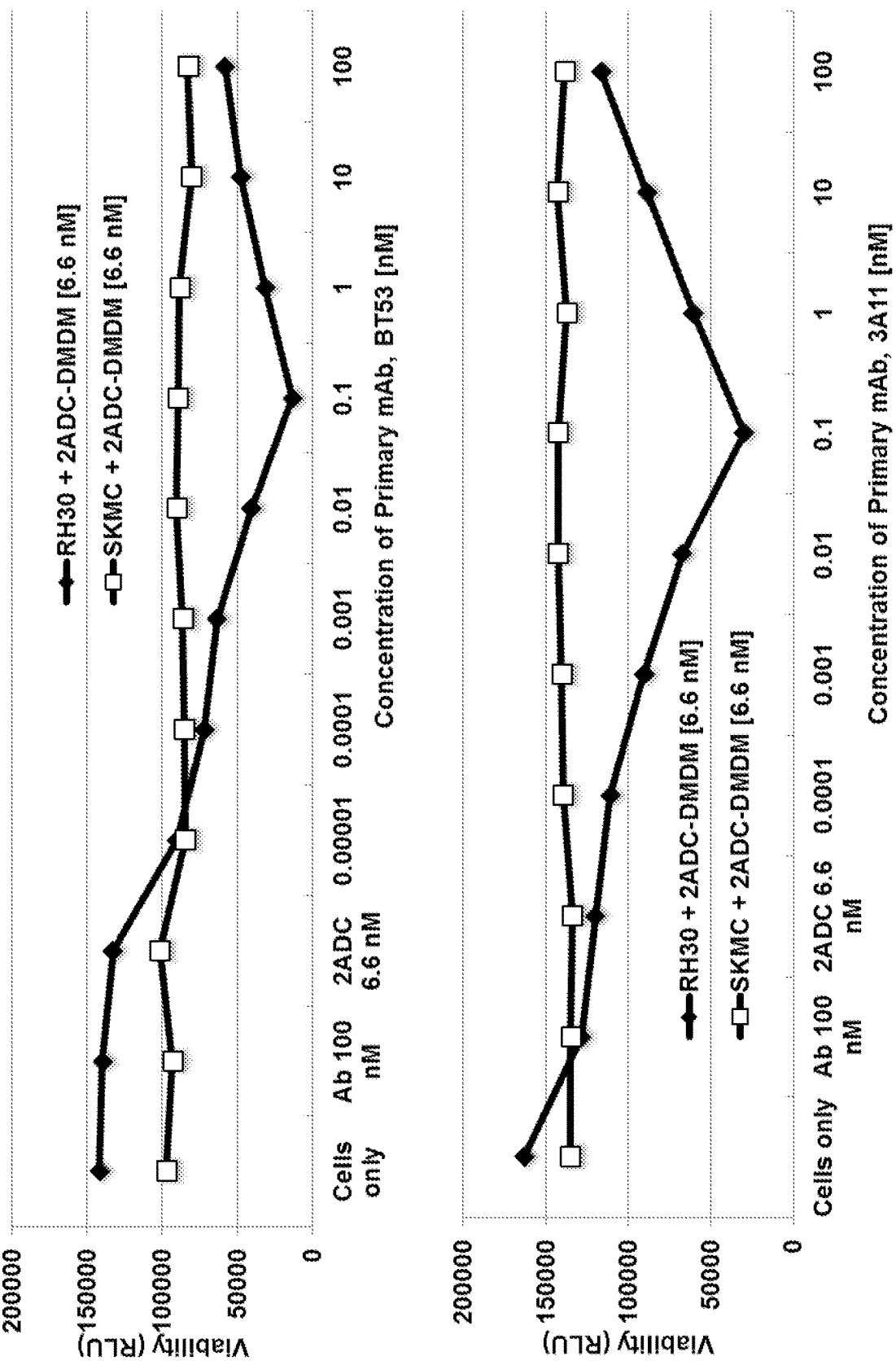

FIG. 9 is a pair of graphs showing specific cytotoxicity of anti-FGFR4 monoclonal antibodies BT53 (top) and 3A11 (bottom) conjugated to secondary antibody-drug conjugates. The FGFR4-specific secondary antibody-drug conjugates induced killing of FGFR4-positive rhabdomyosarcoma cells (RH30), but not FGFR4-negative human skeletal muscle cells (SKMC) cells.

Figure 10A:
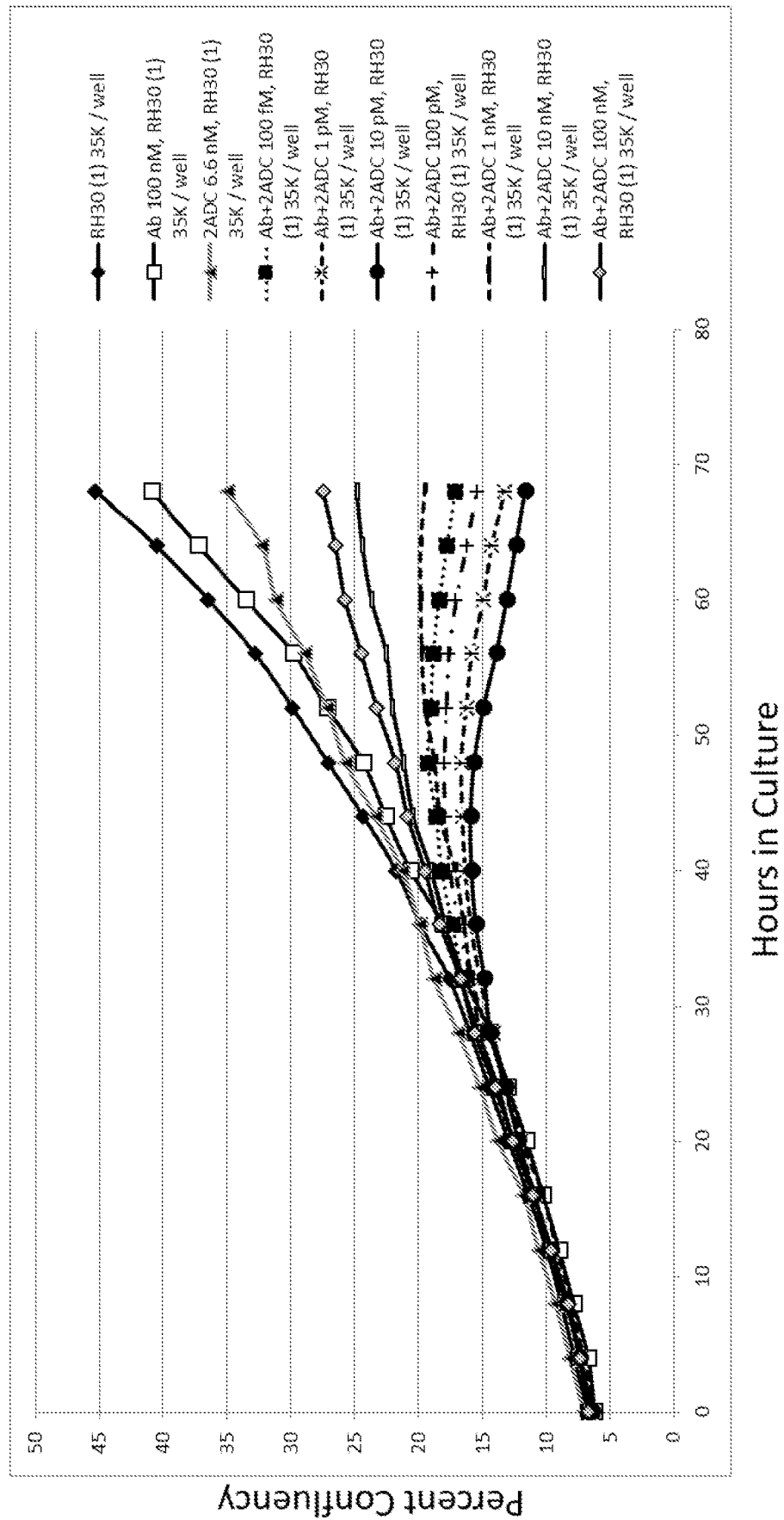
Figure 10B:
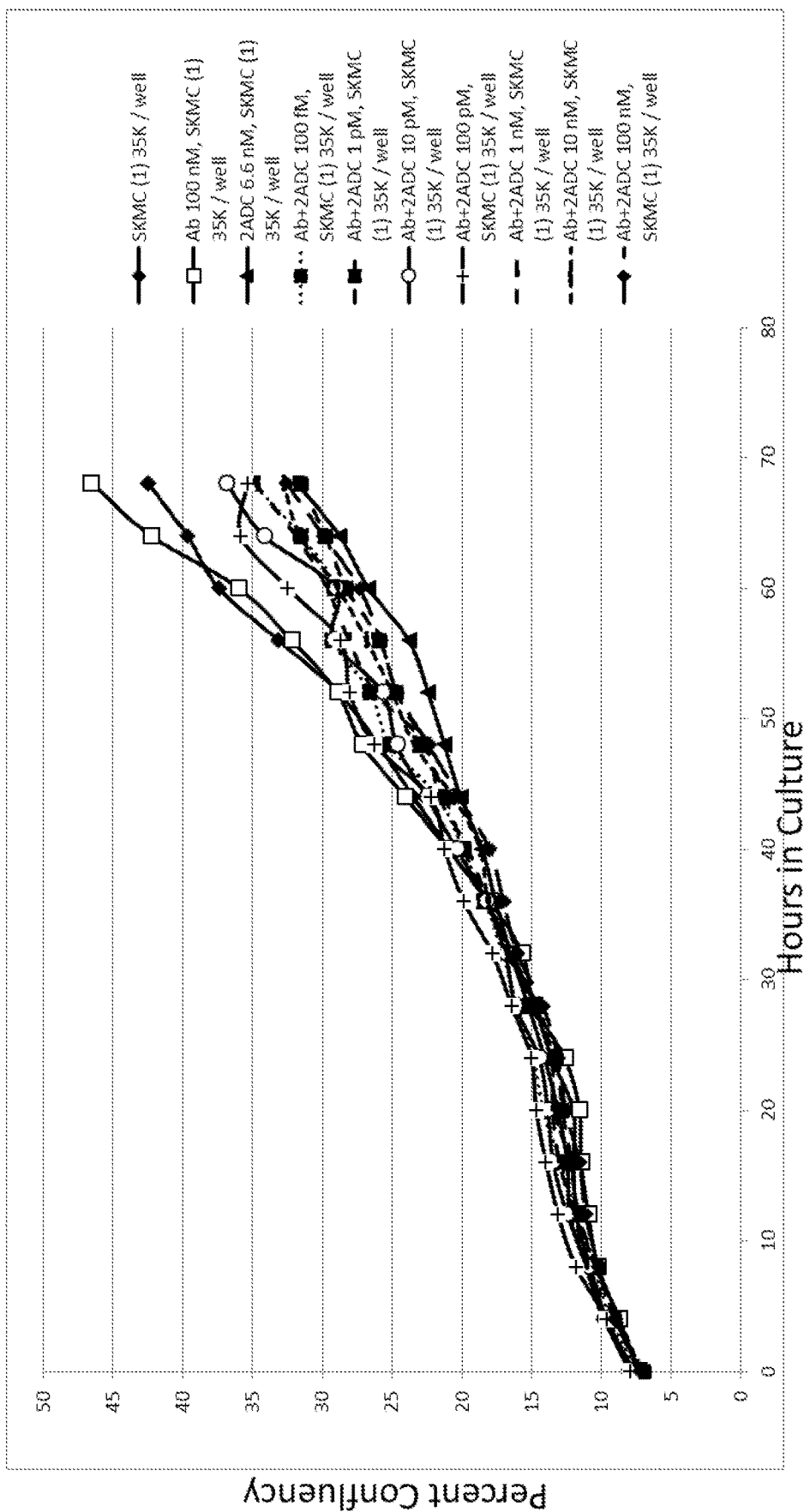

FIGS. 10A-10B are graphs showing growth of FGFR-positive RH30 cells (FIG. 10A) and FGFR4-negative SKMC cells (FIG. 10B) in the presence of the BT53 monoclonal antibody and BT53 secondary ADC.

Figure 11B:
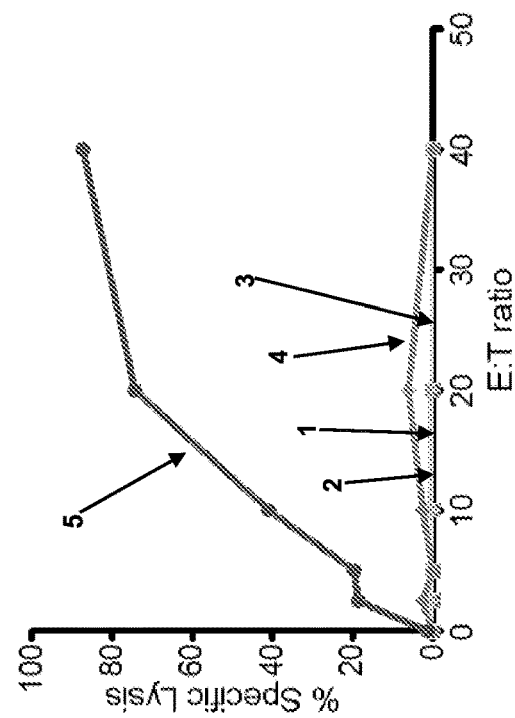
Figure 11A:
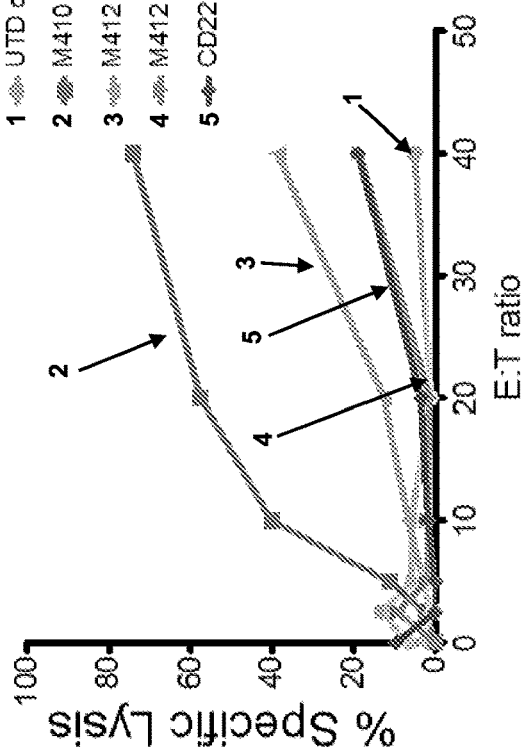

FIGS. 11A-11B are graphs showing cytotoxicity of T cells expressing FGFR4 CARs M410 long, M412 long and M412 short. A CD22 CAR was used as a control. Target RH30 (FGRR4+/CD22-) and Raji (FGFR4-/CD22+) cells were transduced with luciferase and the CELLTITER-GLO™ assay was used to measure the number of viable cells. Percent specific lysis induced by each CAR is shown. FGFR4-specific CARs induced lysis of FGFR4-positive RH30 cells, but not FGFR4-negative Raji cells.

Figure 12:
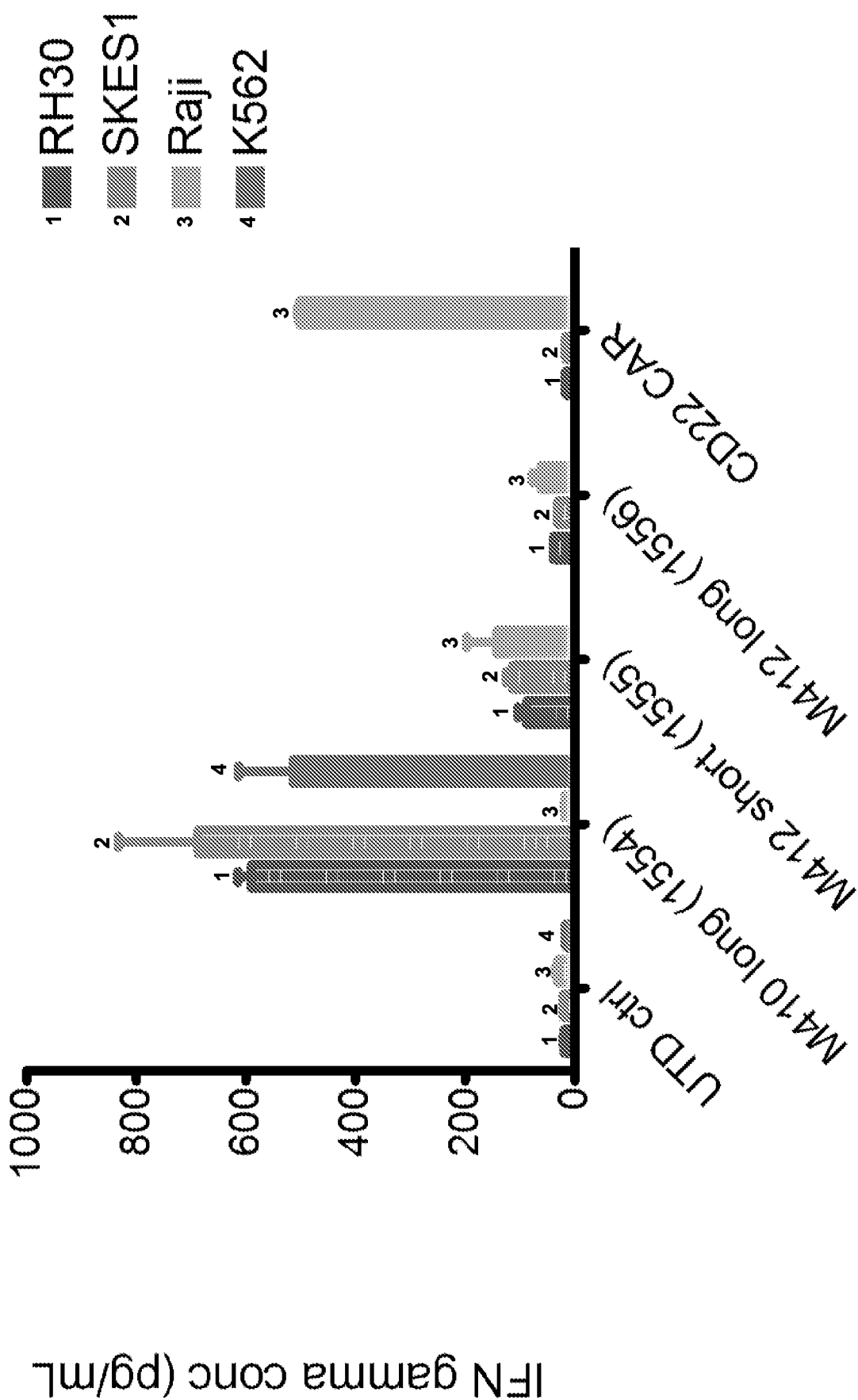

FIG. 12 is a graph showing interferon (IFN)-γ release induced by T cells expressing the FGFR4-specific M410 long, M412 short and M412 long CARs. IFN-γ released by RH30 (FGFR4+), SKES1 (FGFR4+), Raji (FGFR4-) and K562 (FGFR4-) cells is shown.

SEQUENCE LISTING

The amino acid sequences listed in the accompanying sequence listing are shown using standard three letter code for amino acids, as defined in 37 C.F.R. 1.822. The Sequence Listing is submitted as an ASCII text file, created on Sep. 8, 2016, 104 KB, which is incorporated by reference herein. In the accompanying sequence listing:

SEQ ID NO: 1 is the amino acid sequence of the $V_H$ of the BT53 mouse anti-FGFR4 mAb.

SEQ ID NO: 2 is the amino acid sequence of the $V_L$ of the BT53 mouse anti-FGFR4 mAb.

SEQ ID NO: 3 is the amino acid sequence of the $V_H$ of the 3A11 mouse anti-FGFR4 mAb.

SEQ ID NO: 4 is the amino acid sequence of the $V_L$ of the 3A11 mouse anti-FGFR4 mAb.

SEQ ID NO: 5 is the amino acid sequence of the $V_H$ of the 1G5 mouse anti-FGFR4 mAb.

SEQ ID NO: 6 is the amino acid sequence of the $V_L$ of the 1G5 mouse anti-FGFR4 mAb.

SEQ ID NO: 7 is the amino acid sequence of the $V_H$ of the 29.2 rabbit anti-FGFR4 mAb.

SEQ ID NO: 8 is the amino acid sequence of the $V_L$ of the 29.2 rabbit anti-FGFR4 mAb.

SEQ ID NO: 9 is the amino acid sequence of the $V_H$ of the 57.1 rabbit anti-FGFR4 mAb.

SEQ ID NO: 10 is the amino acid sequence of the $V_L$ of the 57.1 rabbit anti-FGFR4 mAb.

SEQ ID NO: 11 is the amino acid sequence of the $V_H$ of the M408 human anti-FGFR4 scFv.

SEQ ID NO: 12 is the amino acid sequence of the $V_L$ of the M408 human anti-FGFR4 scFv.

SEQ ID NO: 13 is the amino acid sequence of the $V_H$ of the M409 human anti-FGFR4 scFv.

SEQ ID NO: 14 is the amino acid sequence of the $V_L$ of the M409 human anti-FGFR4 scFv.

SEQ ID NO: 15 is the amino acid sequence of the $V_H$ of the M410 human anti-FGFR4 scFv.

SEQ ID NO: 16 is the amino acid sequence of the $V_L$ of the M410 human anti-FGFR4 scFv.

SEQ ID NO: 17 is the amino acid sequence of the $V_H$ of the M412 human anti-FGFR4 scFv.

SEQ ID NO: 18 is the amino acid sequence of the $V_L$ of the M412 human anti-FGFR4 scFv.

SEQ ID NO: 19 is the amino acid sequence of the $V_H$ of the M414 human anti-FGFR4 scFv.

SEQ ID NO: 20 is the amino acid sequence of the $V_L$ of the M414 human anti-FGFR4 scFv.

SEQ ID NO: 21 is the amino acid sequence of the $V_H$ of the M415 human anti-FGFR4 scFv.

SEQ ID NO: 22 is the amino acid sequence of the $V_L$ of the M415 human anti-FGFR4 scFv.

SEQ ID NO: 23 is the amino acid sequence of the $V_H$ of the M417 human anti-FGFR4 scFv.

SEQ ID NO: 24 is the amino acid sequence of the $V_L$ of the M417 human anti-FGFR4 scFv.

SEQ ID NO: 25 is the amino acid sequence of the $V_H$ of the M418 human anti-FGFR4 scFv.

SEQ ID NO: 26 is the amino acid sequence of the $V_L$ of the M418 human anti-FGFR4 scFv.

SEQ ID NO: 27 is the amino acid sequence of the $V_H$ of the M422 human anti-FGFR4 scFv.

SEQ ID NO: 28 is the amino acid sequence of the $V_L$ of the M422 human anti-FGFR4 scFv.

SEQ ID NO: 29 is the amino acid sequence of the $V_H$ of the M424 human anti-FGFR4 scFv.

SEQ ID NO: 30 is the amino acid sequence of the $V_L$ of the M424 human anti-FGFR4 scFv.

SEQ ID NO: 31 is the amino acid sequence of a peptide linker for antibody-based CARs.

SEQ ID NO: 32 is the amino acid sequence of a peptide linker featured in scFv sequences.

SEQ ID NO: 33 is the amino acid sequence of an alternative peptide linker featured in scFv sequences.

SEQ ID NO: 34 is the amino acid sequence of an exemplary signal peptide.

SEQ ID NO: 35 is a short linker domain for Ig binding domains to transmembrane sequences (short spacer).

SEQ ID NO: 36 is a linker domain composed of 2 Ig C domains (CH2CH3) used to link Ig binding domains to transmembrane sequences (long spacer).

SEQ ID NO: 37 is the amino acid sequence of a scFv including the $V_H$ and the $V_L$ of the BT53 mouse anti-FGFR4 mAb.

SEQ ID NO: 38 is the amino acid sequence of a scFv including the $V_H$ and the $V_L$ of the 3A11 mouse anti-FGFR4 mAb.

SEQ ID NO: 39 is the amino acid sequence of a scFv including the $V_H$ and the $V_L$ of the 1G5 mouse anti-FGFR4 mAb.

SEQ ID NO: 40 is the amino acid sequence of a scFv including the humanized $V_H$ and the $V_L$ of the BT53 mouse anti-FGFR4 mAb.

SEQ ID NO: 41 is the amino acid sequence of a scFv including the humanized $V_H$ and the $V_L$ of the 3A11 mouse anti-FGFR4 mAb.

SEQ ID NO: 42 is the amino acid sequence of a scFv including the humanized $V_H$ and the $V_L$ of the 1G5 mouse anti-FGFR4 mAb.

SEQ ID NO: 43 is the amino acid sequence of a scFv including the $V_H$ and $V_L$ of the 29.2 rabbit anti-FGFR4 mAb.

SEQ ID NO: 44 is the amino acid sequence of a scFv including the $V_H$ and $V_L$ of the 57.1 rabbit anti-FGFR4 mAb.

SEQ ID NO: 45 is the amino acid sequence of a scFv including the humanized $V_H$ and $V_L$ of the 29.2 rabbit anti-FGFR4 mAb.

SEQ ID NO: 46 is the amino acid sequence of a scFv including the humanized $V_H$ and $V_L$ of the 57.1 rabbit anti-FGFR4 mAb.

SEQ ID NO: 47 is the amino acid sequence of the M408 human anti-FGFR4 scFv.

SEQ ID NO: 48 is the amino acid sequence of the M409 human anti-FGFR4 scFv.

SEQ ID NO: 49 is the amino acid sequence of the M410 human anti-FGFR4 scFv.

SEQ ID NO: 50 is the amino acid sequence of the M412 human anti-FGFR4 scFv.

SEQ ID NO: 51 is the amino acid sequence of the M414 human anti-FGFR4 scFv.

SEQ ID NO: 52 is the amino acid sequence of the M415 human anti-FGFR4 scFv.

SEQ ID NO: 53 is the amino acid sequence of the M417 human anti-FGFR4 scFv.

SEQ ID NO: 54 is the amino acid sequence of the M418 human anti-FGFR4 scFv.

SEQ ID NO: 55 is the amino acid sequence of the M422 human anti-FGFR4 scFv.

SEQ ID NO: 56 is the amino acid sequence of the M424 human anti-FGFR4 scFv.

SEQ ID NO: 57 is the amino acid sequence of an exemplary CD28 transmembrane domain.

SEQ ID NO: 58 is the amino acid sequence of an exemplary CD28 signaling domain.

SEQ ID NO: 59 is the amino acid sequence of exemplary CD28 transmembrane and signaling domains.

SEQ ID NO: 60 is the amino acid sequence of an exemplary CD8 transmembrane domain.

SEQ ID NO: 61 is the amino acid sequence of an exemplary CD8 extended transmembrane domain.

SEQ ID NO: 62 is the amino acid sequence of an exemplary CD137 signaling domain.

SEQ ID NO: 63 is the amino acid sequence of an exemplary CD137 signaling domain.

SEQ ID NO: 64 is the amino acid sequence of an exemplary CD3 zeta signaling domain.

SEQ ID NO: 65 is the amino acid sequence of the transmembrane and intracellular domains of an exemplary second generation CAR including a CD28 transmembrane domain and a CD3 zeta signaling domain ("28z").

SEQ ID NO: 66 is the amino acid sequence of the transmembrane and intracellular domains of an exemplary second generation CAR including a CD8 transmembrane domain, CD137 (4-1BB) signaling domain, and a CD3 zeta signaling domain ("BBz").

SEQ ID NO: 67 is the amino acid sequence of the transmembrane and intracellular domains of an exemplary third generation CAR including a CD8 transmembrane domain, a CD28 signaling domain, a CD137 (4-1BB) signaling domain, and a CD3 zeta signaling domain ("28BBz").

SEQ ID NO: 68 is the amino acid sequence of the 29.2L CAR.

SEQ ID NO: 69 is the amino acid sequence of the 29.2 CAR.

SEQ ID NO: 70 is the amino acid sequence of the 57.1L CAR.

SEQ ID NO: 71 is the amino acid sequence of the 57.1 CAR.

DETAILED DESCRIPTION

I. Abbreviations

ADC antibody-drug conjugate
ADCC antibody-dependent cell-mediated cytotoxicity
ARMS alveolar rhabdomyosarcoma
CAR chimeric antigen receptor
CDC complement-dependent cytotoxicity
CDR complementarity determining region
CTL cytotoxic T lymphocyte
DMDM duocarmycin DM
ECD extracellular domain
ELISA enzyme-linked immunosorbent assay
ERMS embryonal rhabdomyosarcoma
Fc constant fragment
FGFR4 fibroblast growth factor receptor 4
IHC immunohistochemistry ITAM immunoreceptor tyrosine-based activation motif
mAb monoclonal antibody
MMAF monomethyl auristatin F
PBD pyrrolobenzodiazepine
PBMC peripheral blood mononuclear cell
PE *Pseudomonas* exotoxin
RMS rhabdomyosarcoma
scFv single chain variable fragment
TMA tissue microarray
VH variable heavy
VL variable light II. Terms and Methods Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Anti-microtubule agent: A drug that interferes with microtubules. Anti-microtubule agents block cell growth by stopping mitosis.

Anti-mitotic agent: A drug or compound that blocks mitosis.

Antibody: A polypeptide ligand comprising at least a light chain and/or heavy chain immunoglobulin variable region which recognizes and binds (such as specifically recognizes and specifically binds) an epitope of an antigen, such as FGFR4, or a fragment thereof. Immunoglobulin molecules are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody.

Antibodies include intact immunoglobulins and the variants and portions (fragments) of antibodies well known in the art, such as single-domain antibodies (e.g. $V_H$ domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as bispecific antibodies). See also, *Pierce Catalog and Handbook*, 1994-1995 (Pierce Chemical Co., Rockford, Ill.); Kuby, J., *Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as "domains").

In combination, the heavy and the light chain variable regions specifically bind the antigen. Light and heavy chain variable regions contain a "framework" region interrupted by three hypervariable regions, also called "complementarity-determining regions" or "CDRs." The amino acid sequence boundaries of a given CDR can be readily determined using any of a number of well-known schemes, including those described by Kabat et al. (*Sequences of Proteins of Immunological Interest*, U.S. Department of Health and Human Services, 1991; the "Kabat" numbering scheme), Chothia et al. (see Chothia and Lesk, *J Mol Biol* 196:901-917, 1987; Chothia et al., *Nature* 342:877, 1989; and Al-Lazikani et al., (JMB 273,927-948, 1997; the "Chothia" numbering scheme), and the ImMunoGeneTics (IMGT) database (see, Lefranc, *Nucleic Acids Res* 29:207-9, 2001; the "IMGT" numbering scheme). The Kabat and IMGT databases are maintained online. The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are often identified by the chain in which the particular CDR is located. Thus, a $V_H$ CDR3 (or HCDR3) is located in the variable domain of the heavy chain of the antibody in which it is found, whereas a $V_L$ CDR1 (or LCDR1) is the CDR1 from the variable domain of the light chain of the antibody in which it is found. An antibody that binds FGFR4, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "$V_H$" refer to the variable region of an immunoglobulin heavy chain, including that of an Fv, scFv, dsFv or Fab. References to "$V_L$" or "$V_L$" refer to the variable region of an immunoglobulin light chain, including that of an Fv, scFv, dsFv or Fab.

A "monoclonal antibody" is an antibody produced by a single clone of B-lymphocytes or by a cell into which the light and/or heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "chimeric antibody" has framework residues from one species, such as human, and CDRs (which generally confer antigen binding) from another species, such as a murine antibody that specifically binds FGFR4.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rabbit, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other monoclonal antibodies can have additional conservative amino acid substitutions which have substantially no effect on antigen binding or other immunoglobulin functions. Humanized immunoglobulins can be constructed by means of genetic engineering (see for example, U.S. Pat. No. 5,585,089).

Antibody-drug conjugate (ADC): A molecule that includes an antibody (or antigen-binding fragment of an antibody) conjugated to a drug, such as a cytotoxic agent. ADCs can be used to specifically target a drug to cancer cells through specific binding of the antibody to a tumor antigen expressed on the cell surface. Exemplary drugs for use with ADCs include anti-microtubule agents (such as maytansinoids, auristatin E and auristatin F) and interstrand cross-linking agents (e.g., pyrrolobenzodiazepines; PDBs).

Anti-microtubule agent: A type of drug that blocks cell growth by stopping mitosis. Anti-microtubule agents, also referred to as "anti-mitotic agents," are used to treat cancer.

Binding affinity: Affinity of an antibody for an antigen. In one embodiment, affinity is calculated by a modification of the Scatchard method described by Frankel et al. (*Mol. Immunol.*, 16:101-106, 1979). In another embodiment, binding affinity is measured by an antigen/antibody dissociation rate. In another embodiment, binding affinity is measured by a competition radioimmunoassay. In another embodiment, binding affinity is measured by ELISA. An antibody that "specifically binds" an antigen (such as FGFR4) is an antibody that binds the antigen with high affinity and does not significantly bind other unrelated antigens.

Breast cancer: A type of cancer that forms in the tissues of the breast, typically in the ducts and lobules. In some embodiments, a patient with breast cancer is node-positive, meaning the breast cancer has spread to the lymph nodes.

Chemotherapeutic agent: Any chemical agent with therapeutic usefulness in the treatment of diseases characterized by abnormal cell growth. Such diseases include tumors, neoplasms, and cancer as well as diseases characterized by hyperplastic growth, such as psoriasis. In one embodiment, a chemotherapeutic agent is an agent of use in treating a FGFR4-positive cancer, such as rhabdomyosarcoma, lung cancer, liver cancer, breast cancer, pancreatic cancer and prostate cancer. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, *Clinical Oncology* $2^{nd}$ ed., ©2000 Churchill Livingstone, Inc; Baltzer, L., Berkery, R. (eds.): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993). Combination chemotherapy is the administration of more than one agent to treat cancer. One example is the administration of an antibody (or immunoconjugate or ADC) that binds FGFR4 used in combination with a radioactive or chemical compound.

Chimeric antigen receptor (CAR): A chimeric molecule that includes an antigen-binding portion (such as a monoclonal antibody or fragment thereof) and a signaling domain, such as a signaling domain from a T cell receptor (e.g. CD3ζ). Typically, CARs are comprised of a binding moiety (e.g. a scFv), a transmembrane domain and an endodomain. The endodomain typically includes a signaling chain having an immunoreceptor tyrosine-based activation motif (ITAM), such as CD3ζ or FcεRIγ. In some instances, the endodomain further includes the intracellular portion of at least one additional co-stimulatory domain, such as CD28 and/or CD137.

Conservative variant: "Conservative" amino acid substitutions are those substitutions that do not substantially affect or decrease the affinity of a protein, such as an antibody to FGFR4. For example, a monoclonal antibody that specifically binds FGFR4 can include at most about 1, at most about 2, at most about 5, at most about 10, or at most about 15 conservative substitutions and specifically bind a FGFR4 polypeptide. The term "conservative variant" also includes the use of a substituted amino acid in place of an unsubstituted parent amino acid, provided that the antibody specifically binds FGFR4. Non-conservative substitutions are those that reduce an activity or binding to FGFR4.

Complementarity determining region (CDR): Amino acid sequences which together define the binding affinity and specificity of the natural Fv region of a native Ig binding site. The light and heavy chains of an Ig each have three CDRs, designated LCDR1, LCDR2, LCDR3 and HCDR1, HCDR2 and HCDR3, respectively.

Contacting: Placement in direct physical association; includes both in solid and liquid form.

Cytotoxic agent: Any drug or compound that kills cells.

Degenerate variant: In the context of the present disclosure, a "degenerate variant" refers to a polynucleotide encoding a FGFR4 polypeptide or an antibody that binds FGFR4 that includes a sequence that is degenerate as a result of the genetic code. There are 20 natural amino acids, most of which are specified by more than one codon. Therefore, all degenerate nucleotide sequences are included as long as the amino acid sequence of the FGFR4 polypeptide or antibody that binds FGFR4 encoded by the nucleotide sequence is unchanged.

Diagnostic: Identifying the presence or nature of a pathologic condition, such as, but not limited to, cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as cancer or metastasis.

Drug: Any compound used to treat, ameliorate or prevent a disease or condition in a subject. In some embodiments herein, the drug is an anti-cancer agent, for example a cytotoxic agent, such as an anti-mitotic or anti-microtubule agent.

Duocarmycin: A cytotoxic small molecule that induces cell death by binding to the minor groove of DNA and alkylating the adenine.

Effector molecule: The portion of an antibody conjugate (or immunoconjugate) that is intended to have a desired effect on a cell to which the conjugate is targeted. Effector molecules are also known as effector moieties (EMs), therapeutic agents, diagnostic agents, or similar terms. Therapeutic agents (or drugs) include such compounds as small molecules, nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the effector molecule can be contained within an encapsulation system, such as a liposome or micelle, which is conjugated to the antibody. Encapsulation shields the effector molecule from direct exposure to the circulatory system. Means of preparing liposomes attached to antibodies are well known to those of skill in the art (see, for example, U.S. Pat. No. 4,957,735; and Connor et al., Pharm Ther 28:341-365, 1985). Diagnostic agents or moieties include radioisotopes and other detectable labels (e.g., fluorophores, chemiluminescent agents, and enzymes). Radioactive isotopes include $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$.

Epitope: An antigenic determinant. These are particular chemical groups or peptide sequences on a molecule that are antigenic, i.e. that elicit a specific immune response. An antibody specifically binds a particular antigenic epitope on a polypeptide, such as FGFR4.

Fibroblast growth factor receptor (FGFR): A family of tyrosine kinase receptors activated by fibroblast growth factors (FGF), comprising extracellular immunoglobulin-like domains, a transmembrane domain, and an intracellular tyrosine kinase domain. The family includes at least four members: FGFR1, FGFR2, FGFR3, and FGFR4.

Framework region: Amino acid sequences interposed between CDRs. Framework regions include variable light and variable heavy framework regions. The framework regions serve to hold the CDRs in an appropriate orientation for antigen binding.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of antigen-specific antibodies.

Immunoliposome: A liposome with antibodies or antibody fragments conjugated to its surface Immunoliposomes can carry cytotoxic agents or other drugs to antibody-targeted cells, such as tumor cells.

Interstrand crosslinking agent: A type of cytotoxic drug capable of binding covalently between two strands of DNA, thereby preventing DNA replication and/or transcription.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$, $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide within an antibody binding fragment (such as an Fv fragment) which serves to indirectly bond the variable heavy chain to the variable light chain. "Linker" can also refer to a peptide serving to link a targeting moiety, such as an antibody, to an effector molecule, such as a cytotoxin or a detectable label.

The terms "conjugating," "joining," "bonding" or "linking" refer to making two polypeptides into one contiguous polypeptide molecule, or to covalently attaching a radionuclide, drug or other molecule to a polypeptide, such as an antibody or antibody fragment. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Liver cancer: A type of cancer than forms in the tissues of the liver. Types of liver cancers include, for example, hepatocellular carcinoma (HCC), cholangiocarcinoma (also known as bile duct cancer), angiosarcoma and hepatoblastoma.

Lung cancer: Cancer that forms in tissues of the lung, usually in the cells lining air passages. The two main types are small cell lung cancer and non-small cell lung cancer. These types are diagnosed based on how the cells look under a microscope.

Mammal: This term includes both human and non-human mammals. Similarly, the term "subject" includes both human and veterinary subjects.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pancreatic cancer: A disease in which malignant (cancer) cells are found in the tissues of the pancreas. Also called exocrine cancer.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. Remington's Pharmaceutical Sciences, by E. W. Martin, Mack Publishing Co., Easton, Pa., 15th Edition, 1975, describes compositions and formulations suitable for pharmaceutical delivery of the antibodies and conjugates disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Prostate Cancer: A malignant tumor, generally of glandular origin, of the prostate. Prostate cancers include adenocarcinomas and small cell carcinomas. Many prostate cancers express prostate specific antigen (PSA).

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Pyrrolobenzodiazepine (PBD): A class of sequence-selective DNA minor-groove binding crosslinking agents originally discovered in *Streptomyces* species. PDBs are significantly more potent than systemic chemotherapeutic drugs. The mechanism of action of PBDs is associated with their ability to form an adduct in the minor groove of DNA, thereby interfering with DNA processing. In the context of the present disclosure, PBDs include naturally produced and isolated PBDs, chemically synthesized naturally occurring PBDs, and chemically synthesized non-naturally occurring PBDs. PBDs also include monomeric, dimeric and hybrid PBDs (for a review see Gerratana, *Med Res Rev* 32(2):254-293, 2012).

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Rhabdomyosarcoma (RMS): A soft tissue malignant tumor of skeletal muscle origin. The most common primary sites for rhabdomyosarcoma are the head and neck (e.g., parameningeal, orbit, pharyngeal, etc.), the genitourinary tract, and the extremities. Other less common primary sites include the trunk, chest wall, the abdomen (including the retroperitoneum and biliary tract), and the perineal/anal region. There are at least two types of RMS; the most common forms are alveolar RMS (ARMS) and embryonal histological RMS (ERMS). Approximately 20% of children with rhabdomyosarcoma have the ARMS subtype. An increased frequency of this subtype is noted in adolescents and in patients with primary sites involving the extremities, trunk, and perineum/perianal region. ARMS is associated with chromosomal translocations encoding a fusion gene involving FKHR on chromosome 13 and members of the PAX family. The embryonal subtype is the most frequently observed subtype in children, accounting for approximately 60-70% of rhabdomyosarcomas of childhood. Tumors with embryonal histology typically arise in the head and neck region or in the genitourinary tract, although they may occur at any primary site. ERMS is characterized by a younger age at diagnosis, loss of heterozygosity, and altered genomic imprinting.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a tumor biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci.*

U.S.A. 85:2444, 1988; Higgins and Sharp, Gene 73:237, 1988; Higgins and Sharp, CABIOS 5:151, 1989; Corpet et al., Nucleic Acids Research 16:10881, 1988; and Pearson and Lipman, Proc. Natl. Acad. Sci. U.S.A. 85:2444, 1988. Altschul et al., Nature Genet. 6:119, 1994, presents a detailed consideration of sequence alignment methods and homology calculations.

The NCBI Basic Local Alignment Search Tool (BLAST) (Altschul et al., J. Mol. Biol. 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds FGFR4 or a fragment thereof are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Small molecule: A molecule, typically with a molecular weight less than about 1000 Daltons, or in some embodiments, less than about 500 Daltons, wherein the molecule is capable of modulating, to some measurable extent, an activity of a target molecule.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: An agent that directly or indirectly inhibits the growth of and/or kills cells. Toxins include, for example, Pseudomonas exotoxin (PE, such as PE35, PE37, PE38 and PE40), diphtheria toxin (DT), botulinum toxin, abrin, ricin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Monoclonal Antibodies Specific for FGFR4

Rhabdomyosarcoma (RMS) is the most common soft tissue sarcoma of childhood. Two major subtypes, embryonal RMS (ERMS) and alveolar RMS (ARMS), harbor distinct cytogenetic and molecular abnormalities, some of which are associated with poor prognosis. The FGFR4 gene is amplified, overexpressed, and mutationally activated in human RMS, and as such is a tumor-specific target. Previous studies of FGFR4 indicate that this gene plays a role in tumorigenesis and is crucial for the survival, proliferation, metastasis and drug-resistance of RMS. High expression of FGFR4 has been associated with an aggressive phenotype and poor survival. Conversely, genetic or pharmacologic inhibition of FGFR4 signaling has been found to inhibit tumor growth in vitro and in vivo.

Disclosed herein are monoclonal antibodies, or antigen-binding fragments thereof, that specifically bind fibroblast growth factor receptor 4 (FGFR4). The antibodies were selected from mice and rabbits immunized with the extracellular domain of human FGFR4 (hFGFR4-ECD), and from a human scFv library. Chimeric antigen receptors, antibody-drug conjugates, immunoconjugates, bispecific antibodies, immunoliposomes and compositions comprising the FGFR4-specific antibodies are also disclosed herein. The monoclonal antibodies and antibody compositions can be used to diagnose or treat a FGFR4-positive cancer, such as rhabdomyosarcoma, lung cancer, liver cancer, breast cancer, pancreatic cancer or prostate cancer.

Three mouse monoclonal antibodies (BT53, 3A11 and 1G5), two rabbit monoclonal antibodies (29.2 and 57.1) and 10 human scFv (M408, M409, M410, M412, M414, M415, M417, M418, M422 and M424) that specifically bind FGFR4 were identified. The CDR sequences of the antibodies disclosed herein were determined using IMGT. However, one of skill in the art could readily determine the CDR boundaries using alternative numbering schemes, including the Kabat or Chothia numbering schemes.

Mouse Monoclonal Antibody Sequences

The VH and VL domain sequences of mouse monoclonal antibodies BT53, 3A11 and 1G5 and provided below. The CDR sequences, as determined by IMGT, are shown in bold.

SEQ ID NO: 1 is the amino acid sequence of the $V_H$ of the BT53 mouse anti-FGFR4 mAb:

QVQLQQSGAELVRPGASVTLSCKASGYTFTDYEMHWVKKIPVYGLEWIGA

IDPETYGTAYNQKFKGKATLTADKSSSTAYMEVRSLTSEDSAVYYCTRGG

YYGSDFDYWGQGTTLTVSS

SEQ ID NO: 2 is the amino acid sequence of the $V_L$ of the BT53 mouse anti-FGFR4 mAb:

NIVMTQSPKSMSMSVGERVTLTCKASENVVTYVSWYQQKPEQSPKLLIY

GASNRYTGVPDRFTGSGSATDFTLTISSVQAEDLADYHCGQGYSDPYTFG

GGTKLEIK

SEQ ID NO: 3 is the amino acid sequence of the $V_H$ of the 3A11 mouse anti-FGFR4 mAb:

QVQLEQSGAELVRPGASVTLSCKASGYTFTDYEMHWVKQTPVHGLEWIGA

IDPETGGTAYNQKFKGKAILTADKSSSTAYMELRSLTSEDSAVYYCTRGN

YYGSDYDYWGQGTTLTVSS

SEQ ID NO: 4 is the amino acid sequence of the $V_L$ of the 3A11 mouse anti-FGFR4 mAb:

DVVMTQTPLTLSVTIGQPASISCKSSQSLLDSDGETYLNWLLKRPGQSPK

RLIYLVSKLDSGVPDRFTGSGSGTDFTLKISRVEAEDLGVYYCWQGTHFP

QTFGGGTKLEIK

SEQ ID NO: 5 is the amino acid sequence of the $V_H$ of the 1G5 mouse anti-FGFR4 mAb:

QVQLQQSGAELVRPGASVTLSCKASGYTFTDYEMHWVKKIPVYGLEWIGA

IDPETYGTAYNQKFKGKATLTADKSSSTAYMEVRSLTSEDSAVYYCTRGG

YYGSDFDYWGQ

SEQ ID NO: 6 is the amino acid sequence of the $V_L$ of the 1G5 mouse anti-FGFR4 mAb:

DIQMNQSPSSLSASLGDTITITCHASQNINVWLSWYQQKPGNIPKLLIY

KASNLHTGVPSRFSGSGSGTGFTLTISSLQPEDIATYYCQQGQSYPWTFG

GGTKLEIK

Rabbit Monoclonal Antibody Sequences

The VH and VL domain sequences of rabbit monoclonal antibodies 29.2 and 57.1 are provided below. The CDR sequences, as determined by IMGT, are shown in bold.

SEQ ID NO: 7 is the amino acid sequence of the $V_H$ of the 29.2 rabbit anti-FGFR4 mAb:

QSVKESEGRLVTPGTPLTLTCTVSGFSLSSNSVGWVRQAPGKGLEWIGI

ISSSGNRYYASWAKGRFTISKTSTTVDLKITSPTTEDTATYFCGGDPVSW

YGDIWGPGTLVTVSS

SEQ ID NO: 8 is the amino acid sequence of the $V_L$ of the 29.2 rabbit anti-FGFR4 mAb:

LLVTSLLLCELPHPAFLLIPDTELVLTQTPSSVSAAVGGTVTINCQSSPS

LYKNNYLSWYQQKPGQPPKLLIYSASTLASGVPSRFKGSGSGTEYTLTIS

GVQCDDAATYYCLGGYSLSSDSPRAFGGGTEVVVK

SEQ ID NO: 9 is the amino acid sequence of the $V_H$ of the 57.1 rabbit anti-FGFR4 mAb:

QSVKESEGRLVTPGTPLTLTCTVSGFSLSTYAMSWVRQAPEKGLEWIGII

YATAETYYATWARGRFTISKTSTTVDLKITSPATEDTATYFCARLNGDGS

GTYAYDIWGPGTLVTVSS

SEQ ID NO: 10 is the amino acid sequence of the $V_L$ of the 57.1 rabbit anti-FGFR4 mAb:

LLVTSLLLCELPHPAFLLIPDTELVMTQTPSPVSAAVGGTVTINCQASQS

ISSSYLSWYQQKPGQPPKLLIYKASTRPSGVSSRFKGSGSGTQFTLTISG

VQCADAATYYCLYGYYIDSGADNSFGGGTEVVVK

Human scFv Sequences

Provided below are the amino acid sequences of the $V_H$ and $V_L$ domains of human scFv M408, M409, M410, M412, M414, M415, M417, M418, M422 and M424. The CDR sequences, as determined by IMGT, are shown in bold.

SEQ ID NO: 11 is the amino acid sequence of the $V_H$ of the M408 human anti-FGFR4 scFv:

EVQLVQSGVEGKKPEAPVKVSCKASGYTFTNYYMHWVQQAPGKGLEWMGL

VDPEDGETIYAEKFQGRVTITADTSTDTAYMELSSLRSEDTAVYYCARDP

VLLWDGMDVWGQGTT

SEQ ID NO: 12 is the amino acid sequence of the $V_L$ of the M408 human anti-FGFR4 scFv.

DIQMTQSPSSLSASVGDRVTITCRASQTISRYLNWYQQKPGKAPKLLIYA

ASSLQSGVSSRFSGSGSGTEFTLTISSLQPEDFATYFCQQTYSPPITFGQ

GTRLEIKR

SEQ ID NO: 13 is the amino acid sequence of the $V_H$ of the M409 human anti-FGFR4 scFv.

AAQAAQVQLQQSGPGLVKPSQTLSLTCAISGDSVSSNSAAWNWIRQSPSR

GLEWLGRTYYRSKWYNDYAVSVKSRITINPDASKNQFSLQLNSVTPEDTA

VYYCSGSYSTFDIWGQGTM

SEQ ID NO: 14 is the amino acid sequence of the V$_L$ of the M409 human anti-FGFR4 scFv.

NFMLTQPHSVSGSPGKTVTLSCTCSGGNIADAYVQWYQQRPGSAPRIVIY
EDKQRPSGVPDRFSGSIDSSSNSASLTISGLRTEDEADYYCQSYDTNNFW
VFGGGTKLTVLG

SEQ ID NO: 15 is the amino acid sequence of the V$_H$ of the M410 human anti-FGFR4 scFv.

QVQLQQSGAEVKKPGSSVKVSCKASGGTFSSYAISWVRQAPGQGLEWMGG
IIPIFGTANYAQKFQGRVTITADESTSTAYMELSSLRSEDTAVYYCASTI
PYYGDYVEDYYGMDVWGQGTT

SEQ ID NO: 16 is the amino acid sequence of the V$_L$ of the M410 human anti-FGFR4 scFv.

NFMLTQPHSVSESPGRTVSISCTRGSGSIADDYVQWYQQRPGGSPTIVIY
EDNQRPSGVPDRFSGSIDTSSNSASLTISGLTTEDEAVYYCQSYDYRDHW
VFGGGTQLTVLG

SEQ ID NO: 17 is the amino acid sequence of the V$_H$ of the M412 human anti-FGFR4 scFv.

QAAQVQLVESGGGLVQPGGSLRLSCAASGFTFSSYAMSWVRQAPGKGLEW
VSVIYSGGSTYYADSVKGRFTMSRDNSKNTLYLQMNSLRAEDTAVYYCAR
VGLQSGAFDIWGQGTT

SEQ ID NO: 18 is the amino acid sequence of the V$_L$ of the M412 human anti-FGFR4 scFv.

DIQMTQSPSSLSASVGDRVTITCQASQDIYTYLNWYQQKPGKAPMLVIHD
TSNLETGAPSRFSGGGSGTDFSFTISSLQPEDFATYYCQQYDALPFTFGQ
GTKLEIKR

SEQ ID NO: 19 is the amino acid sequence of the V$_H$ of the M414 human anti-FGFR4 scFv.

EVQLVQFGAEVKKPGSSVKVSCKASGGTFSSYAISWVQQAPGKGLEWMGL
VDPEDGETIYAEKFQGRVTMTRDTSTSTVYMELSSLRSEDTAVYYCARDP
GGEGLGAIDGFDIWGQGTT

SEQ ID NO: 20 is the amino acid sequence of the V$_L$ of the M414 human anti-FGFR4 scFv.

DIQMTQSPSSLSASVGDRVTIACRASQTISRYLNWYQQKPGKAPKLLIYA
ASSLQSGVSSRFSGSGSGTEFTLTISSLQPEDFATYFCQQTYSPPITFGQ
GTRLEIKR

SEQ ID NO: 21 is the amino acid sequence of the V$_H$ of the M415 human anti-FGFR4 scFv.

QVQLVESGGGVVQPGGSLRLSCAASGFTFSSYAMHWVRQAPGKGLEWVAV
ISYDGSNKYYADSVKGRFTISRDNSKNTLYLQMNSLRAEDTAVYYCARAW
PEYSSSADAFDIWGQGTM

SEQ ID NO: 22 is the amino acid sequence of the V$_L$ of the M415 human anti-FGFR4 scFv.

DIQLTQSPSSLSASVGDRVTITCQASQDIDNYLNWFQQKPGKPPKLLISD
ASSLETGVPSRFSGSGSGTDFTFTISSLQPEDIATYYCQQYDNFPITFGQ
GTKLEIKRGQAGQGPDKT

SEQ ID NO: 23 is the amino acid sequence of the V$_H$ of the M417 human anti-FGFR4 scFv.

EVQLVESGGALVQPGGSLRLSCAASGFTFTNYGIIWVRQAPGKGPEWVSG
VSGNAVHTYYADSVKGRFTISRDNSKNMVYLQMNSLRSDDTAVYYCARGW
DLDYWGQGTL

SEQ ID NO: 24 is the amino acid sequence of the V$_L$ of the M417 human anti-FGFR4 scFv.

EIVLTQSPSSLSASVGDRVTITCQASQDISNYLNWYQQKPGKAPKLLIYD
ASNLETGVPSRFIGGGSGTDFTLTISSLQPEDFATYYCQQHDSLPLSFGG
GTKLEIKR

SEQ ID NO: 25 is the amino acid sequence of the V$_H$ of the M418 human anti-FGFR4 scFv.

QLQLQESGPGLVKPSETLSLTCVVFDYSISSGYYWGWIRQPPGKGLEWIG
SINYSGNTYYNPSLKSRVTISVDTSKNQFSLNLRSVTAADTAVYYCARSV
DTAPGFDYWGQGTL

SEQ ID NO: 26 is the amino acid sequence of the V$_L$ of the M418 human anti-FGFR4 scFv.

DIQMTQSPSFLSASVGDRVTITCRASQGISSYLAWYQQKPGKAPKLLIYD
ASNLETGVPSRFSGSGSGTDFTFTISSLQPEDIATYYCQQYDNLPLTFGG
GTKLDIKR

SEQ ID NO: 27 is the amino acid sequence of the V$_H$ of the M422 human anti-FGFR4 scFv.

EVQLVQSGAEVKKPGATVKISCKVSGYTFTDYYMHWVQQAPGKGLEWMGL
VDPEDGETIYAEKFQGRVTITADTSTDTAYMELSSLRSEDTAVYYCATER
AVAGPGAFDIWGQGTM

SEQ ID NO: 28 is the amino acid sequence of the V$_L$ of the M422 human anti-FGFR4 scFv.

EIVLTQSPSSLSASVGDRVTIACRASQTISRYLNWYQQKPGKAPKLLIYA
ASSLQSGVSSRFSGSGSGTEFTLTISSLQPEDFATYFCQQTYSPPITFGQ
GTRLEIKR

SEQ ID NO: 29 is the amino acid sequence of the V$_H$ of the M424 human anti-FGFR4 scFv.

QVQLVETGGGVVQPGTSLRLSCAGSGFTFSESGMHWVRQAPGKGLEWMAL
ILNDGISNFYADSVKGRFTISRDNSKNTLYLQMNSLRAEDTAVYYCASSL
GGNGAFDIWGQGTM

SEQ ID NO: 30 is the amino acid sequence of the $V_L$ of the M424 human anti-FGFR4 scFv.

DIQLTQSPSSLSASVGDRVTITCQASQDISNYLNWYQQKPGKAPKLLIY**D
ASNLEIGVPSRFSGSGSGTDFTFTISSLQPEDIATYYCQQHDNLPLSF**GG
GTKLDIKR

TABLE 1

| | IMGT CDR Sequences of FGFR4 Specific Antibodies | | | | |
|---|---|---|---|---|---|
| BT53 | SEQ ID NO: 1 | A.A. Sequence | | SEQ ID NO: 2 | A.A. Sequence |
| HCDR1 | 26-33 | GYTFTDYE | LCDR1 | 27-32 | ENVVTY |
| HCDR2 | 51-58 | IDPETYGT | LCDR2 | 50-52 | GAS |
| HCDR3 | 96-109 | CTRGGYYGSDFDYW | LCDR3 | 88-98 | CGQGYSDPYTF |
| 3A11 | SEQ ID NO: 3 | A.A. Sequence | | SEQ ID NO: 4 | A.A. Sequence |
| HCDR1 | 26-33 | GYTFTDYE | LCDR1 | 27-33 | QSLLDSD |
| HCDR2 | 51-58 | IDPETGGT | LCDR2 | 55-57 | LVS |
| HCDR3 | 96-109 | CTRGNYYGSDYDYW | LCDR3 | 93-103 | CWQGTHFPQTF |
| IG5 | SEQ ID NO: 5 | A.A. Sequence | | SEQ ID NO: 6 | A.A. Sequence |
| HCDR1 | 26-33 | GYTFTDYE | LCDR1 | 27-32 | QNINVW |
| HCDR2 | 52-59 | IDPETYGT | LCDR2 | 50-52 | KAS |
| HCDR3 | 98-111 | CTRGGYYGSDFDYW | LCDR3 | 88-98 | CQQGQSYPWTF |
| 29.2 | SEQ ID NO: 7 | A.A. Sequence | | SEQ ID NO: 8 | A.A. Sequence |
| HCDR1 | 25-32 | GFSLSSNS | LCDR1 | 49-56 | PSLYKNNY |
| HCDR2 | 50-56 | ISSSGNR | LCDR2 | 74-76 | SAS |
| HCDR3 | 92-104 | CGGDPVSWYGDIW | LCDR3 | 112-126 | CLGGYSLSSDSPRAF |
| 57.1 | SEQ ID NO: 9 | A.A. Sequence | | SEQ ID NO: 10 | A.A. Sequence |
| HCDR1 | 25-32 | GFSLSTYA | LCDR1 | 49-55 | QSISSSY |
| HCDR2 | 50-56 | IYATAET | LCDR2 | 73-75 | KAS |
| HCDR3 | 92-108 | CARLNGDGSGTYAYDIW | LCDR3 | 111-125 | CLYGYYIDSGADNSF |
| M408 | SEQ ID NO: 11 | A.A. Sequence | | SEQ ID NO: 12 | A.A. Sequence |
| HCDR1 | 26-33 | GYTFTNYY | LCDR1 | 27-32 | QTISRY |
| HCDR2 | 51-58 | VDPEDGET | LCDR2 | 50-52 | AAS |
| HCDR3 | 96-110 | CARDPVLLWDGMDVW | LCDR3 | 88-97 | CQQTYSPPITF |
| M409 | SEQ ID NO: 13 | A.A. Sequence | | SEQ ID NO: 14 | A.A. Sequence |
| HCDR1 | 31-40 | GDSVSSNSAA | LCDR1 | 26-33 | GGNIADAY |
| HCDR2 | 58-66 | TYYRSKWYN | LCDR2 | 51-53 | EDK |
| HCDR3 | 104-114 | CSGSYSTFDIW | LCDR3 | 91-102 | CQSYDTNNFWVF |

TABLE 1-continued

IMGT CDR Sequences of FGFR4 Specific Antibodies

| M410 | | SEQ ID NO: 15 A.A. Sequence | | | SEQ ID NO: 16 A.A. Sequence |
|---|---|---|---|---|---|
| HCDR1 | 26-33 | GGTFSSYA | LCDR1 | 26-33 | SGSIADDY |
| HCDR2 | 51-58 | IIPIFGTA | LCDR2 | 51-53 | EDN |
| HCDR3 | 96-116 | CASTIPYYGDYVEDYYGMDVW | LCDR3 | 91-102 | CQSYDYRDHWVF |

| M412 | | SEQ ID NO: 17 A.A. Sequence | | | SEQ ID NO: 18 A.A. Sequence |
|---|---|---|---|---|---|
| HCDR1 | 29-36 | GFTFSSYA | LCDR1 | 27-33 | QDIYTYL |
| HCDR2 | 54-60 | IYSGGST | LCDR2 | 50-53 | DTS |
| HCDR3 | 98-111 | CARVGLQSGAFDIW | LCDR3 | 89-99 | CQQYDALPFTF |

| M414 | | SEQ ID NO: 19 A.A. Sequence | | | SEQ ID NO: 20 A.A. Sequence |
|---|---|---|---|---|---|
| HCDR1 | 26-33 | GGTFSSYA | LCDR1 | 37-32 | QTISRY |
| HCDR2 | 51-58 | VDPEDGET | LCDR2 | 51-53 | AAS |
| HCDR3 | 96-114 | CARDPGGEGLGAIDGFDIW | LCDR3 | 89-99 | CQQTYSPPITF |

| M415 | | SEQ ID NO: 21 A.A. Sequence | | | SEQ ID NO: 22 A.A. Sequence |
|---|---|---|---|---|---|
| HCDR1 | 26-33 | GFTFSSYA | LCDR1 | 27-32 | QDIDNY |
| HCDR2 | 51-58 | ISYDGSNK | LCDR2 | 50-52 | DAS |
| HCDR3 | 96-113 | CARAWPEYSSSADAFDIW | LCDR3 | 88-98 | CQQYDNFPITF |

| M417 | | SEQ ID NO: 23 A.A. Sequence | | | SEQ ID NO: 24 A.A. Sequence |
|---|---|---|---|---|---|
| HCDR1 | 26-33 | GFTFTNYG | LCDR1 | 27-32 | QDISNY |
| HCDR2 | 51-58 | VSGNAVHT | LCDR2 | 50-52 | DAS |
| HCDR3 | 97-106 | CARGWDLDYW | LCDR3 | 88-98 | CQQHDSLPLSF |

| M418 | | SEQ ID NO: 25 A.A. Sequence | | | SEQ ID NO: 26 A.A. Sequence |
|---|---|---|---|---|---|
| HCDR1 | 26-34 | DYSISSGYY | LCDR1 | 27-32 | QGISSY |
| HCDR2 | 52-58 | INYSGNT | LCDR2 | 50-52 | DAS |
| HCDR3 | 96-109 | CARSVDTAPGFDYW | LCDR3 | 88-98 | CQQYDNLPLTF |

| M422 | | SEQ ID NO: 27 A.A. Sequence | | | SEQ ID NO: 28 A.A. Sequence |
|---|---|---|---|---|---|
| HCDR1 | 27-34 | GYTFTDYY | LCDR1 | 27-32 | QTISRY |
| HCDR2 | 52-59 | VDPEDGET | LCDR2 | 50-52 | AAS |
| HCDR3 | 96-111 | CATERAVAGPGAFDIW | LCDR3 | 88-98 | CQQTYSPPITF |

| M424 | | SEQ ID NO: 27 A.A. Sequence | | | SEQ ID NO: 28 A.A. Sequence |
|---|---|---|---|---|---|
| HCDR1 | 26-33 | GFTFSESG | LCDR1 | 27-32 | QDISNY |
| HCDR2 | 51-58 | ILNDGISN | LCDR2 | 50-52 | DAS |
| HCDR3 | 96-109 | CASSLGGNGAFDIW | LCDR3 | 88-98 | CQQHDNLPLSF |

Peptide Linker and Signal Peptide Sequences

SEQ ID NO: 31 is the amino acid sequence of a peptide linker for antibody-based CARs:

GGGGSGGGGSGGGGS

SEQ ID NO: 32 is the amino acid sequence of a peptide linker featured in scFv sequences:

VTVSSGGGGSGGGASSGGGS

SEQ ID NO: 33 is the amino acid sequence of an alternative peptide linker featured in scFv sequences: VTVSSGGGGSGGGASGGGGS SEQ ID NO: 34 is the amino acid sequence of an exemplary signal peptide:

LLVTSLLLCELPHPAFLLIPDT

SEQ ID NO: 35 is a short linker domain for Ig binding domains to transmembrane sequences (short spacer): KTTPPSVYGRVKDPKAAAIE SEQ ID NO: 36 is a linker domain composed of 2 Ig C domains (CH2CH3) used to link Ig binding domains to transmembrane sequences (long spacer):

EPKSCDKTHTCPPCPAPELLGGPSVFLFPPKPKDTLMISRTPEVTCVVVD

VSHEDPEVKFNWYVDGVEVHNAKTKPREEQYNSTYRVVSVLTVLHQDWLN

GKEYKCKVSNKALPAPIEKTISKAKGQPREPQVYTLPPSRDELTKNQVSL

TCLVKGFYPSDIAVEWESNGQPENNYKTTPPVLDSDGSFFLYSKLTVDKS

RWQQGNVFSCSVMHEALHNHYTQKSLSLSPGKKDPKAAAIE scFv Sequences

Provided below are the amino acid sequences of exemplary scFv. CDR sequences, as determined by IMGT, are shown in bold; linker sequences are shown in italics.

SEQ ID NO: 37 is the amino acid sequence of a scFv including the V$_H$ and the V$_L$ of the BT53 mouse anti-FGFR4 mAb:

QVQLQQSGAELVRPGASVTLSCKASGYTFTDYEMHWVKKIPVYGLEWIGA

IDPETYGTAYNQKFKGKATLTADKSSSTAYMEVRSLTSEDSAVYYCTRGG

YYGSDFDYWGQTTLTVSS*GGGGSGGGGSGGGGS*NIVMTQSPKSMSMSVG

ERVTLTCKASENVVTYVSWYQQKPEQSPKLLIYGASNRYTGVPDRFTGSG

SATDFTLTISSVQAEDLADYHCGQGYSDPYTFGGGTKLEIK

SEQ ID NO: 38 is the amino acid sequence of a scFv including the V$_H$ and the V$_L$ of the 3A11 mouse anti-FGFR4 mAb:

QVQLEQSGAELVRPGASVTLSCKASGYTFTDYEMHWVKQTPVHGLEWIGA

IDPETGGTAYNQKFKGKAILTADKSSSTAYMELRSLTSEDSAVYYCTRGN

YYGSDYDYWGQTTLTVSS*GGGGSGGGGSGGGGS*DVVMTQTPLTLSVTIG

QPASISCKSSQSLLDSDGETYLNWLLKRPGQSPKRLIYLVSKLDSGVPDR

FTGSGSGTDFTLKISRVEAEDLGVYYCWQGTHFPQTFGGGTKLEIK

SEQ ID NO: 39 is the amino acid sequence of a scFv including the V$_H$ and the V$_L$ of the 1G5 mouse anti-FGFR4 mAb:

QVQLQQSGAELVRPGASVTLSCKASGYTFTDYEMHWVKKIPVYGLEWIGA

IDPETYGTAYNQKFKGKATLTADKSSSTAYMEVRSLTSEDSAVYYCTRGG

YYGSDFDYWGQ*GGGGSGGGGSGGGGS*DIQMNQSPSSLSASLGDTITITCH

ASQNINVWLSWYQQKPGNIPKLLIYKASNLHTGVPSRFSGSGSTGFTLT

ISSLQPEDIATYYCQQGQSYPWTFGGGTKLEIK

SEQ ID NO: 40 is the amino acid sequence of a scFv including the humanized V$_H$ and the V$_L$ of the BT53 mouse anti-FGFR4 mAb:

QVQLQQSGAEVKKPGSSVKVSCKASGYTFTDYEISWVRQAPGQGLEWMGG

IDPETYGTNYAQKFQGRVTITADESTSTAYMELSSLRSEDTAVYYCTRGG

YYGSDFDYWWGQGTMVTVSS*GGGGSGGGGSGGGGS*EIVLTQSPATLSLSP

GERATLSCRASENVVTYAWYQQKPGQAPRLLIYGASRATGIPARFSGSGS

GTDFTLTISSLEPEDFAVYYCGQGYSDPYTFFGQGTKLEIKR

SEQ ID NO: 41 is the amino acid sequence of a scFv including the humanized V$_H$ and the V$_L$ of the 3A11 mouse anti-FGFR4 mAb:

QVQLQQSGAEVKKPGSSVKVSCKASGYTFTDYEISWVRQAPGQGLEWMGG

IDPETGGTNYAQKFQGRVTITADESTSTAYMELSSLRSEDTAVYYCTRGN

YYGSDYDYWWGQGTMVTV*SSGGGGSGGGGSGGGGS*EIVLTQSPATLSLSP

GERATLSCRASQSLLDSDAWYQQKPGQAPRLLIYLVSRATGIPARFSGSG

SGTDFTLTISSLEPEDFAVYYCWQGTHFPQTFFGQGTKLEIKR

SEQ ID NO: 42 is the amino acid sequence of a scFv including the humanized V$_H$ and the V$_L$ of the 1G5 mouse anti-FGFR4 mAb:

QVQLQQSGAEVKKPGSSVKVSCKASGYTFTDYEISWVRQAPGQGLEWMGG

IDPETYGTNYAQKFQGRVTITADESTSTAYMELSSLRSEDTAVYYCTRGG

YYGSDFDYWWGQGTMVTVSS*GGGGSGGGGSGGGGS*EIVLTQSPATLSLSP

GERATLSCRASQNINVWAWYQQKPGQAPRLLIYKASRATGIPARFSGSGS

GTDFTLTISSLEPEDFAVYYCQQGQSYPWTFFGQGTKLEIKR

SEQ ID NO: 43 is the amino acid sequence of a scFv including the V$_H$ and V$_L$ of the 29.2 rabbit anti-FGFR4 mAb:

QSVKESEGRLVTPGTPLTLTCTVSGFSLSSNSVGWVRQAPGKGLEWIGII

SSSGNRYYASWAKGRFTISKTSTTVDLKITSPTTEDTATYFCGGDPVSWY

GDIWGPGTLVTVSS*GGGGSGGGGSGGGGS*LLVTSLLLCELPHPAFLLIPD

TELVLTQTPSSVSAAVGGTVTINCQSSPSLYKNNYLSWYQQKPGQPPKLL

IYSASTLASGVPSRFKGSGSGTEYTLTISGVQCDDAATYYCLGGYSLSSD

SPRAFGGGTEVVVK

SEQ ID NO: 44 is the amino acid sequence of a scFv including the V$_H$ and V$_L$ of the 57.1 rabbit anti-FGFR4 mAb:

QSVKESEGRLVTPGTPLTLTCTVSGFSLSTYAMSWVRQAPEKGLEWIGII
YATAETYYATWARGRFTISKTSTTVDLKITSPATEDTATYFCARLNGDGS
GTYAYDIWGPGTLVTVSSGGGGSGGGGSGGGGSLLVTSLLLCELPHPAFL
LIPDTELVMTQTPSPVSAAVGGTVTINCQASQSISSSYLSWYQQKPGQPP
KLLIYKASTRPSGVSSRFKGSGSGTQFTLTISGVQCADAATYYCLYGYYI
DSGADNSFGGGTEVVVK

SEQ ID NO: 45 is the amino acid sequence of a scFv including the humanized V$_H$ and V$_L$ of the 29.2 rabbit anti-FGFR4 mAb:

QVQLQQSGAEVKKPGSSVKVSCKASGFSLSSNSISWVRQAPGQGLEWMGG
ISSSGNRNYAQKFQGRVTITADESTSTAYMELSSLRSEDTAVYYCGGDPV
SWYGDIWWGQGTMVTVSSGGGGSGGGGSGGGGSEIVLTQSPATLSLSPGE
RATLSCRASPSLYKNNYAWYQQKPGQAPRLLIYSASRATGIPARFSGSGS
GTDFTLTISSLEPEDFAVYYCLGGYSLSSDSPRAFFGQGTKLEIKR

SEQ ID NO: 46 is the amino acid sequence of a scFv including the humanized V$_H$ and V$_L$ of the 57.1 rabbit anti-FGFR4 mAb:

QVQLQQSGAEVKKPGSSVKVSCKASGFSLSTYAISWVRQAPGQGLEWMGG
IYATAETNYAQKFQGRVTITADESTSTAYMELSSLRSEDTAVYYCARLNG
DGSGTYAYDIWWGQGTMVTVSSGGGGSGGGGSGGGGSEIVLTQSPATLSL
SPGERATLSCRASQSISSSYAWYQQKPGQAPRLLIYKASRATGIPARFSG
SGSGTDFTLTISSLEPEDFAVYYCLYGYYIDSGADNSFGQGTKLEIKR

SEQ ID NO: 47 is the amino acid sequence of the M408 human anti-FGFR4 scFv:

EVQLVQSGVEGKKPEAPVKVSCKASGYTFTNYYMHWVQQAPGKGLEWMGL
VDPEDGETIYAEKFQGRVTITADTSTDTAYMELSSLRSEDTAVYYCARDP
VLLWDGMDVWGQGTTVTVSSGGGGSGGGASSGGGSDIQMTQSPSSLSASV
GDRVTITCRASQTISRYLNWYQQKPGKAPKLLIYAASSLQSGVSSRFSGS
GSGTEFTLTISSLQPEDFATYFCQQTYSPPITFGQGTRLEIKR

SEQ ID NO: 48 is the amino acid sequence of the M409 human anti-FGFR4 scFv:

AAQAAQVQLQQSGPGLVKPSQTLSLTCAISGDSVSSNSAAWNWIRQSPSR
GLEWLGRTYYRSKWYNDYAVSVKSRITINPDASKNQFSLQLNSVTPEDTA
VYYCSGSYSTFDIWGQGTMVTVSSGGGGSGGGASSGGGSNFMLTQPHSVS
GSPGKTVTLSCTCSGGNIADAYVQWYQQRPGSAPRIVIYEDKQRPSGVPD
RFSGSIDSSSNSASLTISGLRTEDEADYYCQSYDTNNFWVFGGGTKLTVL
G

SEQ ID NO: 49 is the amino acid sequence of the M410 human anti-FGFR4 scFv:

QVQLQQSGAEVKKPGSSVKVSCKASGGTFSSYAISWVRQAPGQGLEWMGG
IIPIFGTANYAQKFQGRVTITADESTSTAYMELSSLRSEDTAVYYCASTI
PYYGDYVEDYYGMDVWGQGTTVTVSSGGGGSGGGASSGGGSNFMLTQPHS
VSESPGRTVSISCTRGSGSIADDYVQWYQQRPGGSPTIVIYEDNQRPSGV
PDRFSGSIDTSSNSASLTISGLTTEDEAVYYCQSYDYRDHWVFGGGTQLT
VLG

SEQ ID NO: 50 is the amino acid sequence of the M412 human anti-FGFR4 scFv:

QAAQVQLVESGGGLVQPGGSLRLSCAASGFTFSSYAMSWVRQAPGKGLEW
VSVIYSGGSTYYADSVKGRFTMSRDNSKNTLYLQMNSLRAEDTAVYYCAR
VGLQSGAFDIWGQGTTVTVSSGGGGSGGGASGGGGSDIQMTQSPSSLSAS
VGDRVTITCQASQDIYTYLNWYQQKPGKAPMLVIHDTSNLETGAPSRFSG
GGSGTDFSFTISSLQPEDFATYYCQQYDALPFTFGQGTKLEIKR

SEQ ID NO: 51 is the amino acid sequence of the M414 human anti-FGFR4 scFv:

EVQLVQFGAEVKKPGSSVKVSCKASGGTFSSYAISWVQQAPGKGLEWMGL
VDPEDGETIYAEKFQGRVTMTRDTSTSTVYMELSSLRSEDTAVYYCARDP
GGEGLGAIDGFDIWGQGTTVTVSSGGGGSGGGASGGGGSDIQMTQSPSSL
SASVGDRVTIACRASQTISRYLNWYQQKPGKAPKLLIYAASSLQSGVSSR
FSGSGSGTEFTLTISSLQPEDFATYFCQQTYSPPITFGQGTRLEIKR

SEQ ID NO: 52 is the amino acid sequence of the M415 human anti-FGFR4 scFv:

QVQLVESGGGVVQPGGSLRLSCAASGFTFSSYAMHWVRQAPGKGLEWVAV
ISYDGSNKYYADSVKGRFTISRDNSKNTLYLQMNSLRAEDTAVYYCARAW
PEYSSSADAFDIWGQGTMVTVSSGGGGSGGGASGGGGSDIQLTQSPSSLS
ASVGDRVTITCQASQDIDNYLNWFQQKPGIKPPKLLISDASSLETGVPSR
FSGSGSGTDFTFTISSLQPEDIATYYCQQYDNFPITFGQGTKLEIKRGQA
GQGPDKT

SEQ ID NO: 53 is the amino acid sequence of the M417 human anti-FGFR4 scFv:

EVQLVESGGALVQPGGSLRLSCAASGFTFTNYGIIWVRQAPGKGPEWVSG
VSGNAVHTYYADSVKGRFTISRDNSKNMVYLQMNSLRSDDTAVYYCARGW
DLDYWGQGTLVTVSSGGGGSGGGASGGGGSEIVLTQSPSSLSASVGDRVT
ITCQASQDISNYLNWYQQKPGKAPKLLIYDASNLETGVPSRFIGGGSGTD
FTLTISSLQPEDFATYYCQQHDSLPLSFGGGTKLEIKR

SEQ ID NO: 54 is the amino acid sequence of the M418 human anti-FGFR4 scFv:

QLQLQESGPGLVKPSETLSLTCVVFDYSISSGYYWGWIRQPPGKGLEWIG

SINYSGNTYYNPSLKSRVTISVDTSKNQFSLNLRSVTAADTAVYYCARSV

DTAPGFDYWGQGTLVTVSSGGGGSGGGASSGGGSDIQMTQSPSFLSASVG

DRVTITCRASQGISSYLAWYQQKPGKAPKLLIYDASNLETGVPSRFSGSG

SGTDFTFTISSLQPEDIATYYCQQYDNLPLTFGGGTKLDIKR

SEQ ID NO: 55 is the amino acid sequence of the M422 human anti-FGFR4 scFv:

EVQLVQSGAEVKKPGATVKISCKVSGYTFTDYYMHWVQQAPGKGLEWMGL

VDPEDGETIYAEKFQGRVTITADTSTDTAYMELSSLRSEDTAVYYCATER

AVAGPGAFDIWGQGTMVTVSSGGGGSGGGASGGGGSEIVLTQSPSSLSAS

VGDRVTIACRASQTISRYLNWYQQKPGKAPKLLIYAASSLQSGVSSRFSG

SGSGTEFTLTISSLQPEDFATYFCQQTYSPPITFGQGTRLEIKR

SEQ ID NO: 56 is the amino acid sequence of the M424 human anti-FGFR4 scFv:

QVQLVETGGGVVQPGTSLRLSCAGSGFTFSESGMHWVRQAPGKGLEWMAL

ILNDGISNFYADSVKGRFTISRDNSKNTLYLQMNSLRAEDTAVYYCASSL

GGNGAFDIWGQGTMVTVSSGGGGSGGGASSGGGSDIQLTQSPSSLSASVG

DRVTITCQASQDISNYLNWYQQKPGKAPKLLIYDASNLEIGVPSRFSGSG

SGTDFTFTISSLQPEDIATYYCQQHDNLPLSFGGGTKLDIKR

Signaling Domains

Amino acid sequences of exemplary signaling domains that can be used for chimeric antigen receptors (CARs) are provided below.

SEQ ID NO: 57 is the amino acid sequence of an exemplary CD28 transmembrane domain:

IEVMYPPPYLDNEKSNGTIIHVKGKHLCPSPLFPGPSKPFWVLVVVGGVL

ACYSLLVTVAFIIFWVR

SEQ ID NO: 58 is the amino acid sequence of an exemplary CD28 signaling domain:

SKRSRLLHSDYMNMTPRRPGPTRKHYQPYAPPRDFAAYRS

SEQ ID NO: 59 is the amino acid sequence of exemplary CD28 transmembrane and signaling domains:

IEVMYPPPYLDNEKSNGTIIHVKGKHLCPSPLFPGPSKPFWVLVVVGGVL

ACYSLLVTVAFIIFWVRSKRSRLLHSDYMNMTPRRPGPTRKHYQPYAPPR

DFAAYRS

SEQ ID NO: 60 is the amino acid sequence of an exemplary CD8 transmembrane domain:

TTTPAPRPPTPAPTIASQPLSLRPEACRPAAGGAVHTRGLDFACDIYIWA

PLAGTCGVLLLSLVITLYC

SEQ ID NO: 61 is the amino acid sequence of an exemplary CD8 extended transmembrane domain:

FVPVFLPAKPTTTPAPRPPTPAPTIASQPLSLRPEACRPAAGGAVHTRGL

DFACDIYIWAPLAGTCGVLLLSLVITLYCNHRNR

SEQ ID NO: 62 is the amino acid sequence of an exemplary CD137 signaling domain:

KRGRKKLLYIFKQPFMRPVQTTQEEDGCSCRFPEEEEGGCEL

SEQ ID NO: 63 is the amino acid sequence of an exemplary CD137 signaling domain:

RFSVVKRGRKKLLYIFKQPFMRPVQTTQEEDGCSCRFPEEEEGGCEL

SEQ ID NO: 64 is the amino acid sequence of an exemplary CD3 zeta signaling domain:

RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

SEQ ID NO: 65 is the amino acid sequence of the transmembrane and intracellular domains of an exemplary second generation CAR including a CD28 transmembrane domain and a CD3 zeta signaling domain ("28z"):

AAAIEVMYPPPYLDNEKSNGTIIHVKGKHLCPSPLFPGPSKPFWVLVVVG

GVLACYSLLVTVAFIIFWVRSKRSRLLHSDYMNMTPRRPGPTRKHYQPYA

PPRDFAAYRSRVKFSRSADAPAYQQGQNQLYNELNLGRREEYDVLDKRRG

RDPEMGGKPRRKNPQEGLYNELQKDKMAEAYSEIGMKGERRRGKGHDGLY

QGLSTATKDTYDALHMQALPPR

SEQ ID NO: 66 is the amino acid sequence of the transmembrane and intracellular domains of an exemplary 2$^{nd}$ generation CAR including a CD8 transmembrane domain, CD137 (4-1BB) signaling domain, and a CD3 zeta signaling domain ("BBz"):

AAATTTPAPRPPTPAPTIASQPLSLRPEACRPAAGGAVHTRGLDFACDIY

IWAPLAGTCGVLLLSLVITLYCKRGRKKLLYIFKQPFMRPVQTTQEEDGC

SCRFPEEEEGGCELRVKFSRSADAPAYKQGQNQLYNELNLGRREEYDVLD

KRRGRDPEMGGKPRRKNPQEGLYNELQKDKMAEAYSEIGMKGERRRGKGH

DGLYQGLSTATKDTYDALHMQALPPR

SEQ ID NO: 67 is the amino acid sequence of the transmembrane and intracellular domains of an exemplary 3$^{rd}$ generation CAR including a CD8 transmembrane domain, a CD28 signaling domain, a CD137 (4-1BB) signaling domain, and a CD3 zeta signaling domain ("28BBz"):

AAAFVPVFLPAKPTTTPAPRPPTPAPTIASQPLSLRPEACRPAAGGAVHT

RGLDFACDIYIWAPLAGTCGVLLLSLVITLYCNHRNRSKRSRLLHSDYMN

-continued
MTPRRPGPTRKHYQPYAPPRDFAAYRSRFSVVKRGRKKLLYIFKQPFMRP

VQTTQEEDGCSCRFPEEEEGGCELRVKFSRSADAPAYQQGQNQLYNELNL

GRREEYDVLDKRRGRDPEMGGKPRRKNPQEGLYNELQKDKMAEAYSEIGM

KGERRRGKGHDGLYQGLSTATKDTYDALHMQALPPR

Exemplary CARs

Listed below are exemplary FGFR4-specific CARs that can be used for adoptive immunotherapy. All the CAR molecules include an N-terminal signal peptide (SP; SEQ ID NO: 34), a scFv sequence, a transmembrane (TM) sequence and a CD3 zeta signaling sequence. CARs that refer to "SH" do not have a CH2CH3 spacer domain.

The extracellular domain of the following exemplary CARs is a "short" extracellular domain, which is a CAR without a CH2CH3 spacer:

| BT53 | SP - murine BT53 scFv |
| 3A11 | SP - murine 3A11 scFv |
| 1G5 | SP - murine 1G5 scFv |
| 29.2 | SP - rabbit 29.2 scFv |
| 57.1 | SP - rabbit 57.1 scFv |
| hBT53 | SP - humanized BT53 scFv |
| h3A11 | SP - humanized 3A11 scFv |
| h1G5 | SP - humanized 1G5 scFv |
| h29.2 | SP - humanized 29.2 scFv |
| h57.1 | SP - humanized 57.1 scFv |
| M408 | SP - M408 scFv |
| M409 | SP - M409 scFv |
| M410 | SP - M410 scFv |
| M412 | SP - M412 scFv |
| M414 | SP - M414 scFv |
| M415 | SP - M415 scFv |
| M417 | SP - M417 scFv |
| M418 | SP - M418 scFv |
| M422 | SP - M422 scFv |
| M424 | SP - M424 scFv |

The extracellular domain of the following exemplary CARs is a "long" CAR extracellular domain with a CH2CH3 spacer (SEQ ID: NO 36, CH2CH3):

| BT53L | SP - murine BT53 scFv-CH2CH3 |
| 3A11L | SP - murine 3A11 scFv-CH2CH3 |
| 1G5L | SP - murine 1G5 scFv-CH2CH3 |
| 29.2L | SP - rabbit 29.2 scFv-CH2CH3 |
| 57.1L | SP - rabbit 57.1 scFv-CH2CH3 |
| hBT53L | SP - humanized BT53 scFv-CH2CH3 |
| hSA11L | SP - humanized 3A11 scFv-CH2CH3 |
| h1G5L | SP - humanized 1G5 scFv-CH2CH3 |
| h29.2L | SP - humanized 29.2 scFv-CH2CH3 |
| h57.1L | SP - humanized 57.1 scFv-CH2CH3 |
| M408L | SP- M408 scFv-CH2CH3 |
| M409L | SP - M409 scFv-CH2CH3 |
| M410L | SP - M410 scFv-CH2CH3 |
| M412L | SP - M412 scFv-CH2CH3 |
| M414L | SP - M414 scFv-CH2CH3 |
| M415L | SP - M415 scFv-CH2CH3 |
| M417L | SP - M417 scFv-CH2CH3 |
| M418L | SP - M418 scFv-CH2CH3 |
| M422L | SP - M422 scFv-CH2CH3 |
| M424L | SP - M424 scFv-CH2CH3 |

For the CAR transmembrane domain and intracellular domains, the following nomenclature is used:

| 28z | CD28 transmembrane - CD28 signaling - CD3 zeta signaling |
| BBz | CD8 transmembrane - 4-1BB/CD137 signaling - CD3 zeta signaling |
| 28BBz | CD8 transmembrane - CD28 signaling - 4-1BB/CD137 signaling - CD3 zeta signaling |

In some embodiments in which the CAR extracellular domains are not linked to a CD8 transmembrane domain (i.e. 28z), a short linker (SEQ ID NO: 35) follows the scFv prior to joining the transmembrane sequence.

Exemplary CAR Sequences

The amino acid sequences of four exemplary CARs are provided below. Shown in italics are scFv peptide linkers; the long (CH2CH3) and short linkers for linking Ig domains to transmembrane domains are shown in bold.

29.2L (SEQ ID NO: 68):
LLVTSLLLCELPHPAFLLIPDTELVLTQTPSSVSAAVGGTVTINCQSSPS

LYKNNYLSWYQQKPGQPPKLLIYSASTLASGVPSRFKGSGSGTEYTLTIS

GVQCDDAATYYCLGGYSLSSDSPRAFGGGTEVVVK*GGGGSGGGGSGGGGS*

*QSVKESEGRLVTPGTPLTLTCTVSGFSLSSNSVGWVRQAPGKGLEWIGII*

*SSSGNRYYASWAKGRFTISKTSTTVDLKITSPTTEDTATYFCGGDPVSWY*

GDIWGPGTLVTVSSEPKSCDKTHTCPPCPAPELLGGPSVFLFPPKPKDTL

MISRTPEVTCVVVDVSHEDPEVKFNWYVDGVEVHNAKTKPREEQYNSTYR

VVSVLTVLHQDWLNGKEYKCKVSNKALPAPIEKTISKAKGQPREPQVYTL

PPSRDELTKNQVSLTCLVKGFYPSDIAVEWESNGQPENNYKTTPPVLDSD

GSFFLYSKLTVDKSRWQQGNVFSCSVMHEALHNHYTQKSLSLSPGKKDPK

29.2 (SEQ ID NO: 69):
LLVTSLLLCELPHPAFLLIPDTELVLTQTPSSVSAAVGGTVTINCQSSPS

LYKNNYLSWYQQKPGQPPKLLIYSASTLASGVPSRFKGSGSGTEYTLTIS

GVQCDDAATYYCLGGYSLSSDSPRAFGGGTEVVVK*GGGGSGGGGSGGGGS*

*QSVKESEGRLVTPGTPLTLTCTVSGFSLSSNSVGWVRQAPGKGLEWIGII*

*SSSGNRYYASWAKGRFTISKTSTTVDLKITSPTTEDTATYFCGGDPVSWY*

GDIWGPGTLVTVSSKTTPPSVYGRVKDPK

57.1L (SEQ ID NO: 70):
LLVTSLLLCELPHPAFLLIPDTELVMTQTPSPVSAAVGGTVTINCQASQS

ISSSYLSWYQQKPGQPPKLLIYKASTRPSGVSSRFKGSGSGTQFTLTISG

VQCADAATYYCLYGYYIDSGADNSFGGGTEVVVK*GGGGSGGGGSGGGGSQ*

*SVKESEGRLVTPGTPLTLTCTVSGFSLSTYAMSWVRQAPEKGLEWIGIIY*

*ATAETYYATWARGRFTISKTSTTVDLKITSPATEDTATYFCARLNGDGSG*

TYAYDIWGPGTLVTVSSEPKSCDKTHTCPPCPAPELLGGPSVFLFPPKPK

DTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQV

YTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPGKK

DPK

57.1 (SEQ ID NO: 71):
LLVTSLLLCELPHPAFLLIPDTELVMTQTPSPVSAAVGGTVTINCQASQS

ISSSYLSWYQQKPGQPPKLLIYKASTRPSGVSSRFKGSGSGTQFTLTISG

-continued

```
VQCADAATYYCLYGYYIDSGADNSFGGGTEVVVKGGGGSGGGGSGGGGSQ

SVKESEGRLVTPGTPLTLTCTVSGFSLSTYAMSWVRQAPEKGLEWIGIIY

ATAETYYATWARGRFTISKTSTTVDLKITSPATEDTATYFCARLNGDGSG

TYAYDIWGPGTLVTVSSKTTPPSVYGRVKDPK
```

Provided herein are isolated monoclonal antibodies that bind FGFR4, or antigen-binding fragments thereof, comprising a variable heavy (VH) domain and a variable light (VL) domain. In some embodiments, the monoclonal antibodies or antigen-binding fragments comprise at least a portion of one of the amino acid sequences set forth herein as SEQ ID NOs: 1-30, such as one or more (such as all three) CDR sequences from one of SEQ ID NOs: 1-30. In some examples, the CDR locations are determined IMGT, Kabat or Chothia.

In some embodiments, the VH domain of the antibody comprises the CDR sequences of SEQ ID NO: 1 and the VL domain of the antibody comprises the CDR sequences of SEQ ID NO: 2; the VH domain of the antibody comprises the CDR sequences of SEQ ID NO: 3 and the VL domain of the antibody comprises the CDR sequences of SEQ ID NO: 4; the VH domain of the antibody comprises the CDR sequences of SEQ ID NO: 5 and the VL domain of the antibody comprises the CDR sequences of SEQ ID NO: 6; the VH domain of the antibody comprises the CDR sequences of SEQ ID NO: 7 and the VL domain of the antibody comprises the CDR sequences of SEQ ID NO: 8; the VH domain of the antibody comprises the CDR sequences of SEQ ID NO: 9 and the VL domain of the antibody comprises the CDR sequences of SEQ ID NO: 10; the VH domain of the antibody comprises the CDR sequences of SEQ ID NO: 11 and the VL domain of the antibody comprises the CDR sequences of SEQ ID NO: 12; the VH domain of the antibody comprises the CDR sequences of SEQ ID NO: 13 and the VL domain of the antibody comprises the CDR sequences of SEQ ID NO: 14; the VH domain of the antibody comprises the CDR sequences of SEQ ID NO: 15 and the VL domain of the antibody comprises the CDR sequences of SEQ ID NO: 16; the VH domain of the antibody comprises the CDR sequences of SEQ ID NO: 17 and the VL domain of the antibody comprises the CDR sequences of SEQ ID NO: 18; the VH domain of the antibody comprises the CDR sequences of SEQ ID NO: 19 and the VL domain of the antibody comprises the CDR sequences of SEQ ID NO: 20; the VH domain of the antibody comprises the CDR sequences of SEQ ID NO: 21 and the VL domain of the antibody comprises the CDR sequences of SEQ ID NO: 22; the VH domain of the antibody comprises the CDR sequences of SEQ ID NO: 23 and the VL domain of the antibody comprises the CDR sequences of SEQ ID NO: 24; the VH domain of the antibody comprises the CDR sequences of SEQ ID NO: 25 and the VL domain of the antibody comprises the CDR sequences of SEQ ID NO: 26; the VH domain of the antibody comprises the CDR sequences of SEQ ID NO: 27 and the VL domain of the antibody comprises the CDR sequences of SEQ ID NO: 28; or the VH domain of the antibody comprises the CDR sequences of SEQ ID NO: 29 and the VL domain of the antibody comprises the CDR sequences of SEQ ID NO: 30. In some examples, the CDR sequences are determined using the IMGT, Kabat or Chothia numbering scheme.

In some embodiments, the VH domain of the antibody comprises residues 26-33, 51-58 and 96-109 of SEQ ID NO: 1 and the VL domain of the antibody comprises residues 27-32, 50-52 and 88-98 of SEQ ID NO: 2; the VH domain of the antibody comprises residues 26-33, 51-58 and 96-109 of SEQ ID NO: 3 and the VL domain of the antibody comprises residues 27-33, 55-57 and 93-103 of SEQ ID NO: 4; the VH domain of the antibody comprises residues 26-33, 52-59 and 98-111 of SEQ ID NO: 5 and the VL domain of the antibody comprises residues 27-32, 50-52 and 88-98 of SEQ ID NO: 6; the VH domain of the antibody comprises residues 25-32, 50-56 and 92-104 of SEQ ID NO: 7 and the VL domain of the antibody comprises residues 49-56, 74-76 and 112-126 of SEQ ID NO: 8; the VH domain of the antibody comprises residues 25-32, 50-56 and 92-108 of SEQ ID NO: 9 and the VL domain of the antibody comprises residues 49-55, 73-75 and 111-125 of SEQ ID NO: 10; the VH domain of the antibody comprises residues 26-33, 51-58 and 96-110 of SEQ ID NO: 11 and the VL domain of the antibody comprises residues 27-32, 50-52 and 88-97 of SEQ ID NO: 12; the VH domain of the antibody comprises residues 31-40, 58-66 and 104-114 of SEQ ID NO: 13 and the VL domain of the antibody comprises residues 26-33, 51-53 and 91-102 of SEQ ID NO: 14; the VH domain of the antibody comprises residues 26-33, 51-58 and 96-116 of SEQ ID NO: 15 and the VL domain of the antibody comprises residues 26-33, 51-53 and 91-102 of SEQ ID NO: 16; the VH domain of the antibody comprises residues 29-36, 54-60 and 98-111 of SEQ ID NO: 17 and the VL domain of the antibody comprises residues 27-33, 50-53 and 89-99 of SEQ ID NO: 18; the VH domain of the antibody comprises residues 26-33, 51-58 and 96-114 of SEQ ID NO: 19 and the VL domain of the antibody comprises residues 37-32, 51-53 and 89-99 of SEQ ID NO: 20; the VH domain of the antibody comprises residues 26-33, 51-58 and 96-113 of SEQ ID NO: 21 and the VL domain of the antibody comprises residues 27-32, 50-52 and 88-98 of SEQ ID NO: 22; the VH domain of the antibody comprises residues 26-33, 51-58 and 97-106 of SEQ ID NO: 23 and the VL domain of the antibody comprises residues 27-32, 50-52 and 88-98 of SEQ ID NO: 24; the VH domain of the antibody comprises residues 26-34, 52-58 and 96-109 of SEQ ID NO: 25 and the VL domain of the antibody comprises residues 27-32, 50-52 and 88-98 of SEQ ID NO: 26; the VH domain of the antibody comprises residues 27-34, 52-59 and 96-111 of SEQ ID NO: 27 and the VL domain of the antibody comprises residues 27-32, 50-52 and 88-98 of SEQ ID NO: 28; or the VH domain of the antibody comprises residues 26-33, 51-58 and 96-109 of SEQ ID NO: 29 and the VL domain of the antibody comprises residues 27-32, 50-52 and 88-98 of SEQ ID NO: 30.

In some embodiments, the amino acid sequence of the VH domain is at least 80%, at least 85%, at least 90%, at least 95%, at least 96%, at least 97%, at least 98% or at least 99% identical to SEQ ID NO: 1 and the amino acid sequence of the VL domain is at least 80%, at least 85%, at least 90%, at least 95%, at least 96%, at least 97%, at least 98% or at least 99% identical to SEQ ID NO: 2; the amino acid sequence of the VH domain is at least 80%, at least 85%, at least 90%, at least 95%, at least 96%, at least 97%, at least 98% or at least 99% identical to SEQ ID NO: 3 and the amino acid sequence of the VL domain is at least 80%, at least 85%, at least 90%, at least 95%, at least 96%, at least 97%, at least 98% or at least 99% identical to SEQ ID NO: 4; the amino acid sequence of the VH domain is at least 80%, at least 85%, at least 90%, at least 95%, at least 96%, at least 97%, at least 98% or at least 99% identical to SEQ ID NO: 5 and the amino acid sequence of the VL domain is at least 80%, at least 85%, at least 90%, at least 95%, at least 96%, at least 97%, at least 98% or at least 99% identical to SEQ ID NO: 6; the amino acid sequence of the VH domain is at least 80%, at least 85%, at least 90%, at least 95%, at least 96%, at least 97%, at least 98% or at least 99% identical to SEQ ID NO: 7 and the amino acid sequence of the VL domain is at least 80%, at least 85%, at least 90%, at least 95%, at least 96%, at least 97%, at least 98% or at least 99% identical to SEQ ID NO: 8; the amino acid sequence of the VH domain is at least 80%, at least 85%, at least 90%, at least 95%, at least 96%, at least 97%, at least 98% or at least 99% identical to SEQ ID NO: 9 and the amino acid sequence of the VL domain is at least 80%, at least 85%, at least 90%, at least 95%, at least 96%, at least 97%, at least 98% or at least 99% identical to SEQ ID NO: 10; the amino acid sequence of the VH domain is at least 80%, at least 85%, at least 90%, at least 95%, at least 96%, at least 97%, at least 98% or at least 99% identical to SEQ ID NO: 11 and the amino acid sequence of the VL domain is at least 80%, at least 85%, at least 90%, at least 95%, at least 96%, at least 97%, at least 98% or at least 99% identical to SEQ ID NO: 12; the amino acid sequence of the VH domain is at least 80%, at least 85%, at least 90%, at least 95%, at least 96%, at least 97%, at least 98% or at least 99% identical to SEQ ID NO: 13 and the amino acid sequence of the VL domain is at least 80%, at least 85%, at least 90%, at least 95%, at least 96%, at least 97%, at least 98% or at least 99% identical to SEQ ID NO: 14; the amino acid sequence of the VH domain is at least 80%, at least 85%, at least 90%, at least 95%, at least 96%, at least 97%, at least 98% or at least 99% identical to SEQ ID NO: 15 and the amino acid sequence of the VL domain is at least 80%, at least 85%, at least 90%, at least 95%, at least 96%, at least 97%, at least 98% or at least 99% identical to SEQ ID NO: 16; the amino acid sequence of the VH domain is at least 80%, at least 85%, at least 90%, at least 95%, at least 96%, at least 97%, at least 98% or at least 99% identical to SEQ ID NO: 17 and the amino acid sequence of the VL domain is at least 80%, at least 85%, at least 90%, at least 95%, at least 96%, at least 97%, at least 98% or at least 99% identical to SEQ ID NO: 18; the amino acid sequence of the VH domain is at least 80%, at least 85%, at least 90%, at least 95%, at least 96%, at least 97%, at least 98% or at least 99% identical to SEQ ID NO: 19 and the amino acid sequence of the VL domain is at least 80%, at least 85%, at least 90%, at least 95%, at least 96%, at least 97%, at least 98% or at least 99% identical to SEQ ID NO: 20; the amino acid sequence of the VH domain is at least 80%, at least 85%, at least 90%, at least 95%, at least 96%, at least 97%, at least 98% or at least 99% identical to SEQ ID NO: 21 and the amino acid sequence of the VL domain is at least 80%, at least 85%, at least 90%, at least 95%, at least 96%, at least 97%, at least 98% or at least 99% identical to SEQ ID NO: 22; the amino acid sequence of the VH domain is at least 80%, at least 85%, at least 90%, at least 95%, at least 96%, at least 97%, at least 98% or at least 99% identical to SEQ ID NO: 23 and the amino acid sequence of the VL domain is at least 80%, at least 85%, at least 90%, at least 95%, at least 96%, at least 97%, at least 98% or at least 99% identical to SEQ ID NO: 24; the amino acid sequence of the VH domain is at least 80%, at least 85%, at least 90%, at least 95%, at least 96%, at least 97%, at least 98% or at least 99% identical to SEQ ID NO: 25 and the amino acid sequence of the VL domain is at least 80%, at least 85%, at least 90%, at least 95%, at least 96%, at least 97%, at least 98% or at least 99% identical to SEQ ID NO: 26; the amino acid sequence of the VH domain is at least 80%, at least 85%, at least 90%, at least 95%, at least 96%, at least 97%, at least 98% or at least 99% identical to SEQ ID NO: 27 and the amino acid sequence of the VL domain is at least 80%, at least 85%, at least 90%, at least 95%, at least 96%, at least 97%, at least 98% or at least 99% identical to SEQ ID NO: 28; or the amino acid sequence of the VH domain is at least 80%, at least 85%, at least 90%, at least 95%, at least 96%, at least 97%, at least 98% or at least 99% identical to SEQ ID NO: 29 and the amino acid sequence of the VL domain is at least 80%, at least 85%, at least 90%, at least 95%, at least 96%, at least 97%, at least 98% or at least 99% identical to SEQ ID NO: 30.

In some embodiments, the amino acid sequence of the VH domain comprises SEQ ID NO: 1 and the amino acid sequence of the VL domain comprises SEQ ID NO: 2; the amino acid sequence of the VH domain comprises SEQ ID NO: 3 and the amino acid sequence of the VL domain comprises SEQ ID NO: 4; the amino acid sequence of the VH domain comprises SEQ ID NO: 5 and the amino acid sequence of the VL domain comprises SEQ ID NO: 6; the amino acid sequence of the VH domain comprises SEQ ID NO: 7 and the amino acid sequence of the VL domain comprises SEQ ID NO: 8; the amino acid sequence of the VH domain comprises SEQ ID NO: 9 and the amino acid sequence of the VL domain comprises SEQ ID NO: 10; the amino acid sequence of the VH domain comprises SEQ ID NO: 11 and the amino acid sequence of the VL domain comprises SEQ ID NO: 12; the amino acid sequence of the VH domain comprises SEQ ID NO: 13 and the amino acid sequence of the VL domain comprises SEQ ID NO: 14; the amino acid sequence of the VH domain comprises SEQ ID NO: 15 and the amino acid sequence of the VL domain comprises SEQ ID NO: 16; the amino acid sequence of the VH domain comprises SEQ ID NO: 17 and the amino acid sequence of the VL domain comprises SEQ ID NO: 18; the amino acid sequence of the VH domain comprises SEQ ID NO: 19 and the amino acid sequence of the VL domain comprises SEQ ID NO: 20; the amino acid sequence of the VH domain comprises SEQ ID NO: 21 and the amino acid sequence of the VL domain comprises SEQ ID NO: 22; the amino acid sequence of the VH domain comprises SEQ ID NO: 23 and the amino acid sequence of the VL domain comprises SEQ ID NO: 24; the amino acid sequence of the VH domain comprises SEQ ID NO: 25 and the amino acid sequence of the VL domain comprises SEQ ID NO: 26; the amino acid sequence of the VH domain comprises SEQ ID NO: 27 and the amino acid sequence of the VL domain comprises SEQ ID NO: 28; or the amino acid sequence of the VH domain comprises SEQ ID NO: 29 and the amino acid sequence of the VL domain comprises SEQ ID NO: 30.

In some examples, antigen-binding fragment that binds FGFR4 is an Fab fragment, an Fab' fragment, an F(ab)'$_2$ fragment, a single chain variable fragment (scFv) or a disulfide stabilized variable fragment (dsFv).

In particular non-limiting examples, the fragment is a scFv comprising an amino acid sequence at least 80%, at least 85%, at least 90%, at least 95%, at least 96%, at least 97%, at least 98% or at least 99% identical to SEQ ID NO: 37, SEQ ID NO: 38, SEQ ID NO: 39, SEQ ID NO: 43 or SEQ ID NO: 44. In non-limiting examples, the fragment is a scFv comprising the amino acid sequence of SEQ ID NO: 37, SEQ ID NO: 38, SEQ ID NO: 39, SEQ ID NO: 43 or SEQ ID NO: 44.

In particular non-limiting examples, the fragment is a humanized scFv comprising an amino acid sequence at least 80%, at least 85%, at least 90%, at least 95%, at least 96%, at least 97%, at least 98% or at least 99% identical to SEQ ID NO: 40, SEQ ID NO: 41, SEQ ID NO: 42, SEQ ID NO:

45 or SEQ ID NO: 46. In specific examples, the fragment is a humanized scFv comprising the amino acid sequence of SEQ ID NO: 40, SEQ ID NO: 41, SEQ ID NO: 42, SEQ ID NO: 45 or SEQ ID NO: 46.

In some examples, the monoclonal antibody is an IgG. In other examples, the monoclonal antibody is an IgA, IgD, IgE or IgM.

In some embodiments, the antibody or antigen-binding fragment is a fully human antibody or antigen-binding fragment. In other embodiments, the antibody or antigen-binding fragment is a chimeric, synthetic, humanized or human antibody.

Further provided herein are antibody-drug conjugates (ADCs) that include a drug conjugated to a FGFR4 monoclonal antibody or antigen-binding fragment disclosed herein. In some embodiments, the drug is a small molecule. In some embodiments, the drug is an anti-microtubule agent, an anti-mitotic agent and/or a cytotoxic agent. In particular examples, the drug is monomethyl auristatin F (MMAF) or duocarmycin. ADCs are further discussed herein in section V below.

Also provided herein are chimeric antigen receptors (CARs) that include a monoclonal antibody or antigen-binding fragment disclosed herein, a transmembrane domain and a signaling domain. In some examples, the CARs further include a signal peptide and/or one or more linker peptides.

In some embodiments, the transmembrane domain of the CAR comprises a CD28 or a CD8 transmembrane domain. In some examples, the amino acid sequence of the CD28 transmembrane domain is at least 80%, at least 85%, at least 90%, at least 95%, at least 96%, at least 97%, at least 98% or at least 99% identical to the amino acid sequence of SEQ ID NO: 57; or the amino acid sequence of the CD8 transmembrane domain is at least 80%, at least 85%, at least 90%, at least 95%, at least 96%, at least 97%, at least 98% or at least 99% identical to the amino acid sequence of SEQ ID NO: 60 or SEQ ID NO: 61. In specific non-limiting examples, the CD28 transmembrane domain comprises or consists of the amino acid sequence of SEQ ID NO: 57; or the CD8 transmembrane domain comprises or consists of the amino acid sequence of SEQ ID NO: 60 or SEQ ID NO: 61.

In some embodiments, the signaling domain of the CAR comprises a CD28, CD137 or CD3ζ signaling domain. In some examples, the amino acid sequence of the CD28 signaling domain is at least 80%, at least 85%, at least 90%, at least 95%, at least 96%, at least 97%, at least 98% or at least 99% identical to the amino acid sequence of SEQ ID NO: 58; the amino acid sequence of the CD137 signaling domain is at least 80%, at least 85%, at least 90%, at least 95%, at least 96%, at least 97%, at least 98% or at least 99% identical to the amino acid sequence of SEQ ID NO: 62 or SEQ ID NO: 63; or the amino acid sequence of the CD3ζ signaling domain is at least 80%, at least 85%, at least 90%, at least 95%, at least 96%, at least 97%, at least 98% or at least 99% identical to the amino acid sequence of SEQ ID NO: 64. In specific non-limiting embodiments, the CD28 signaling domain comprises or consists of the amino acid sequence of SEQ ID NO: 58; the CD137 signaling domain comprises or consists of the amino acid sequence of SEQ ID NO: 62 or SEQ ID NO: 63; or the CD3ζ signaling domain comprises or consists of the amino acid sequence of SEQ ID NO: 64.

In some examples, the amino acid sequence of the transmembrane and signaling domains of the CAR is at least 80%, at least 85%, at least 90%, at least 95%, at least 96%, at least 97%, at least 98% or at least 99% identical to the amino acid sequence of SEQ ID NO: 59, SEQ ID NO: 65, SEQ ID NO: 66 or SEQ ID NO: 67. In particular examples, the transmembrane and signaling domains of the CAR comprise or consist of the amino acid sequence of SEQ ID NO: 59, SEQ ID NO: 65, SEQ ID NO: 66 or SEQ ID NO: 67.

In some examples, the amino acid sequence of the CAR is at least 80%, at least 85%, at least 90%, at least 95%, at least 96%, at least 97%, at least 98% or at least 99% identical to SEQ ID NO: 68, SEQ ID NO: 69, SEQ ID NO: 70 or SEQ ID NO: 71. In particular examples, the amino acid sequence of the CAR comprises SEQ ID NO: 68, SEQ ID NO: 69, SEQ ID NO: 70 or SEQ ID NO: 71.

Also provided are isolated cells expressing a CAR disclosed herein. In some embodiments, the cell is a cytotoxic T lymphocyte (CTL). CARs are described further in section VI below.

Immunoconjugates that include a FGFR4-specific monoclonal antibody or antigen-binding fragment disclosed herein and an effector molecule are also provided by the present disclosure. In some embodiments, the effector molecule is a toxin, such as *Pseudomonas* exotoxin or a variant thereof. In other embodiments, the effector molecule is a detectable label, such as a fluorescent, radioactive or enzymatic label Immunoconjugates are discussed in greater detail in section VIII below.

Bispecific antibodies that include a FGFR4-specific monoclonal antibody or antigen-binding fragment disclosed herein and a second monoclonal antibody or antigen-binding fragment thereof are further provided. In some embodiments, the second monoclonal antibody or antigen-binding fragment thereof specifically binds a component of the T cell receptor, such as CD3, or specifically binds a natural killer (NK) cell activating receptor, such as CD16. In some examples, the FGFR4-specific antigen-binding fragment and the second antigen-binding fragment are scFv molecules. Bispecific antibodies are discussed in greater detail in section VII below.

Also provided herein are immunoliposomes that include a liposome conjugated to a FGFR4-specific monoclonal antibody or antigen-binding fragment disclosed herein. In some embodiments, the liposome comprises a cytotoxic agent, such as an anti-cancer agent. Immunoliposomes are further described in section IX.

Further provided herein are compositions that include a disclosed FGFR4-specific monoclonal antibody or antigen-binding fragment thereof, ADC, CAR, isolated cell, immunoconjugate, bispecific antibody or immunoliposome and a pharmaceutically acceptable carrier. Compositions and methods of their use are discussed further in section X below.

Also provided herein are isolated nucleic acid molecules encoding the FGFR4-specific monoclonal antibodies or antigen-binding fragments, CARs, immunoconjugates and bispecific antibodies disclosed herein. In some embodiments, the nucleic acid molecules are operably linked to a promoter. Further provided are vectors that include the nucleic acid molecules disclosed herein. Isolated host cells transformed with the disclosed nucleic acid molecules and vectors are further provided by the present disclosure.

Methods of inhibiting tumor growth or metastasis of a FGFR4-positive cancer are provided herein. In some embodiments, the method includes selecting a subject with a FGFR4-positive cancer and administering to the subject a therapeutically effective amount of a FGFR4-specific monoclonal antibody, antigen-binding fragment, ADC, CAR, isolated cell, immunoconjugate, bispecific antibody, immunoliposome or composition disclosed herein. Also provided are methods of treating a FGFR4-positive cancer in a subject by selecting a subject with a FGFR4-positive cancer and administering to the subject a therapeutically effective amount of a monoclonal antibody, antigen-binding fragment, ADC, CAR, isolated cell, immunoconjugate, bispecific antibody, immunoliposome or composition disclosed herein. In some examples, the FGFR4-positive cancer is a rhabdomyosarcoma (RMS), lung cancer, liver cancer, breast cancer, pancreatic cancer or prostate cancer. In particular examples, the RMS is alveolar RMS (ARMS) or embryonal RMS (ERMS).

Further provided herein are methods of detecting expression of FGFR4 in a sample. In some embodiments, the method includes contacting the sample with the monoclonal antibody or antigen-binding fragment disclosed herein; and detecting binding of the antibody or antigen-binding fragment to the sample. In some examples, the monoclonal antibody or antigen-binding fragment is directly labeled. In other examples, the method further includes contacting the monoclonal antibody or antigen-binding fragment with a second antibody (for example, an anti-IgG antibody), and detecting the binding of the second antibody to the monoclonal antibody or antigen-binding fragment. In specific examples, the sample is obtained from a subject suspected of having a FGFR4-positive cancer. The sample can be any suitable biological samples, such as a cell or tissue sample. In some instances, the sample is a tumor biopsy.

IV. Monoclonal Antibodies and Antigen-Binding Fragments Thereof

The monoclonal antibodies disclosed herein can be of any isotype. The monoclonal antibody can be, for example, an IgM or an IgG antibody, such as $IgG_1$ or an $IgG_2$. The class of an antibody that specifically binds FGFR4 can be switched with another (for example, IgG can be switched to IgM), according to well-known procedures. Class switching can also be used to convert one IgG subclass to another, such as from $IgG_1$ to $IgG_2$.

Antibody fragments are also encompassed by the present disclosure, such as single-domain antibodies (e.g., VH domain antibodies), Fab, $F(ab')_2$, and Fv. These antibody fragments retain the ability to selectively bind with the antigen. These antigen-binding fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the variable region of the light chain and the variable region of the heavy chain expressed as two chains;

(5) Single chain antibody (such as scFv), a genetically engineered molecule containing the variable region of the light chain, the variable region of the heavy chain, linked by a suitable polypeptide linker as a genetically fused single chain molecule;

(6) A dimer of a single chain antibody ($scFV_2$), defined as a dimer of a scFv (also known as a "miniantibody"); and (7) VH single-domain antibody, an antibody fragment consisting of the heavy chain variable domain.

Methods of making these fragments are known in the art (see for example, Harlow and Lane, *Antibodies: A Laboratory Manual*, Cold Spring Harbor Laboratory, New York, 1988).

In some cases, antibody fragments can be prepared by proteolytic hydrolysis of the antibody or by expression in a host cell (such as *E. coli*) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. Nos. 4,036,945, 4,331,647).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and/or the $V_L$ regions to increase yield. Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

V. Antibody-Drug Conjugates (ADCs)

ADCs are compounds comprised of a tumor antigen-specific antibody and a drug, typically a cytotoxic agent, such as an anti-microtubule agent or cross-linking agent. Because ADCs are capable of specifically targeting cancer cells, the drug can be much more potent than agents used for standard chemotherapy. The most common cytotoxic drugs currently used with ADCs have an $IC_{50}$ that is 100- to 1000-fold more potent than conventional chemotherapeutic agents. Common cytotoxic drugs include anti-microtubule agents, such as maytansinoids and auristatins (such as auristatin E and auristatin F). Other cytotoxins for use with ADCs include pyrrolobenzodiazepines (PDBs), which covalently bind the minor groove of DNA to form interstrand crosslinks. In many instances, ADCs comprise a 1:2 to 1:4 ratio of antibody to drug (Bander, *Clinical Advances in Hematology & Oncology* 10(8; suppl 10):3-7, 2012).

The antibody and drug can be linked by a cleavable or non-cleavable linker. However, in some instances, it is desirable to have a linker that is stable in the circulation to prevent systemic release of the cytotoxic drug that could result in significant off-target toxicity. Non-cleavable linkers prevent release of the cytotoxic agent before the ADC is internalized by the target cell. Once in the lysosome, digestion of the antibody by lysosomal proteases results in the release of the cytotoxic agent (Bander, *Clinical Advances in Hematology & Oncology* 10(8; suppl 10):3-7, 2012).

One method for site-specific and stable conjugation of a drug to a monoclonal antibody is via glycan engineering. Monoclonal antibodies have one conserved N-linked oligosaccharide chain at the Asn297 residue in the CH2 domain of each heavy chain (Qasba et al., *Biotechnol Prog* 24:520-526, 2008). Using a mutant β1,4-galactosyltransferase enzyme (Y289L-Gal-T1; U.S. Patent Application Publication Nos. 2007/0258986 and 2006/0084162, herein incorporated by reference), 2-keto-galactose is transferred to free GlcNAc residues on the antibody heavy chain to provide a chemical handle for conjugation.

The oligosaccharide chain attached to monoclonal antibodies can be classified into three groups based on the terminal galactose residues—fully galactosylated (two galactose residues; IgG-G2), one galactose residue (IgG-G1) or completely degalactosylated (IgG-G0). Treatment of a monoclonal antibody with β1,4-galactosidase converts the antibody to the IgG-G0 glycoform. The mutant β1,4-galactosyltransferase enzyme is capable of transferring 2-keto-galactose or 2-azido-galactose from their respective UDP derivatives to the GlcNAc residues on the IgG-G1 and IgG-G0 glycoforms. The chemical handle on the transferred sugar enables conjugation of a variety of molecules to the monoclonal antibody via the glycan residues (Qasba et al., *Biotechnol Prog* 24:520-526, 2008).

Provided herein are ADCs that include a drug (such as a cytotoxic agent) conjugated to a monoclonal antibody that binds (such as specifically binds) FGFR4. In some embodiments, the drug is a small molecule. In some examples, the drug is a cross-linking agent, an anti-microtubule agent and/or anti-mitotic agent, or any cytotoxic agent suitable for mediating killing of tumor cells. Exemplary cytotoxic agents include, but are not limited to, a PDB, an auristatin, a maytansinoid, dolastatin, calicheamicin, nemorubicin and its derivatives, PNU-159682, anthracycline, *vinca* alkaloid, taxane, trichothecene, CC1065, camptothecin, elinafide, a combretastain, a dolastatin, a duocarmycin, an enediyne, a geldanamycin, an indolino-benzodiazepine dimer, a puromycin, a tubulysin, a hemiasterlin, a spliceostatin, or a pladienolide, as well as stereoisomers, isosteres, analogs, and derivatives thereof that have cytotoxic activity.

In some embodiments, the ADC comprises a pyrrolobenzodiazepine (PBD). The natural product anthramycin (a PBD) was first reported in 1965 (Leimgruber et al., *J Am Chem Soc*, 87:5793-5795, 1965; Leimgruber et al., *J Am Chem Soc*, 87:5791-5793, 1965). Since then, a number of PBDs, both naturally-occurring and synthetic analogues, have been reported (Gerratana, *Med Res Rev* 32(2):254-293, 2012; and U.S. Pat. Nos. 6,884,799; 7,049,311; 7,067,511; 7,265,105; 7,511,032; 7,528,126; and 7,557,099). As one example, PDB dimers recognize and bind to specific DNA sequences, and have been shown to be useful as cytotoxic agents. PBD dimers have been conjugated to antibodies and the resulting ADC shown to have anti-cancer properties (see, for example, US2010/0203007). Exemplary linkage sites on the PBD dimer include the five-membered pyrrolo ring, the tether between the PBD units, and the N10-C11 imine group (see WO2009/016516; US2009/304710; US2010/047257; US2009/036431; US 2011/0256157; and WO 2011/130598).

In some embodiments, the ADC comprises an antibody conjugated to one or more maytansinoid molecules. Maytansinoids are derivatives of maytansine, and are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

In some embodiments, the ADC includes an antibody conjugated to a dolastatin or auristatin, or an analog or derivative thereof (see U.S. Pat. Nos. 5,635,483; 5,780,588; 5,767,237; and 6,124,431). Auristatins are derivatives of the marine mollusk compound dolastatin-10. Dolastatins and auristatins have been shown to interfere with microtubule dynamics, GTP hydrolysis, and nuclear and cellular division (Woyke et al., *Antimicrob Agents and Chemother* 45(12): 3580-3584, 2001) and have anticancer (U.S. Pat. No. 5,663,149) and antifungal activity (Pettit et al., *Antimicrob Agents Chemother* 42:2961-2965, 1998). Exemplary dolastatins and auristatins include, but are not limited to, dolastatin 10, auristatin E, auristatin F, auristatin EB (AEB), auristatin EFP (AEFP), MMAD (Monomethyl Auristatin D or monomethyl dolastatin 10), MMAF (Monomethyl Auristatin F or N-methylvaline-valine-dolaisoleuine-dolaproine-phenylalanine), MMAE (Monomethyl Auristatin E or N-methylvaline-valine-dolaisoleuine-dolaproine-norephedrine), 5-benzoylvaleric acid-AE ester (AEVB), and other auristatins (see, for example, U.S. Publication No. 2013/0129753).

In some embodiments, the ADC comprises an antibody conjugated to one or more calicheamicin molecules. The calicheamicin family of antibiotics, and analogues thereof, are capable of producing double-stranded DNA breaks at sub-picomolar concentrations (Hinman et al., *Cancer Res* 53:3336-3342, 1993; Lode et al., *Cancer Res* 58:2925-2928, 1998). Exemplary methods for preparing ADCs with a calicheamicin drug moiety are described in U.S. Pat. Nos. 5,712,374; 5,714,586; 5,739,116; and 5,767,285.

In some embodiments, the ADC comprises an anthracycline. Anthracyclines are antibiotic compounds that exhibit cytotoxic activity. It is believed that anthracyclines can operate to kill cells by a number of different mechanisms, including intercalation of the drug molecules into the DNA of the cell thereby inhibiting DNA-dependent nucleic acid synthesis; inducing production of free radicals which then react with cellular macromolecules to cause damage to the cells; and/or interactions of the drug molecules with the cell membrane. Non-limiting exemplary anthracyclines include doxorubicin, epirubicin, idarubicin, daunomycin, daunorubicin, doxorubicin, epirubicin, nemorubicin, valrubicin and mitoxantrone, and derivatives thereof. For example, PNU-159682 is a potent metabolite (or derivative) of nemorubicin (Quintieri et al., *Clin Cancer Res* 11(4):1608-1617, 2005). Nemorubicin is a semisynthetic analog of doxorubicin with a 2-methoxymorpholino group on the glycoside amino of doxorubicin (Grandi et al., *Cancer Treat Rev* 17:133, 1990; Ripamonti et al., *Br J Cancer* 65:703-707, 1992).

In some embodiments, the ADC can further include a linker. In some examples, the linker is a bifunctional or multifunctional moiety that can be used to link one or more drug moieties to an antibody to form an ADC. In some embodiments, ADCs are prepared using a linker having reactive functionalities for covalently attaching to the drug and to the antibody. For example, a cysteine thiol of an antibody can form a bond with a reactive functional group of a linker or a drug-linker intermediate to make an ADC.

In some examples, a linker has a functionality that is capable of reacting with a free cysteine present on an antibody to form a covalent bond. Exemplary linkers with such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates.

In some examples, a linker has a functionality that is capable of reacting with an electrophilic group present on an antibody. Examples of such electrophilic groups include, but are not limited to, aldehyde and ketone carbonyl groups. In some cases, a heteroatom of the reactive functionality of the linker can react with an electrophilic group on an antibody and form a covalent bond to an antibody unit. Non-limiting examples include hydrazide, oxime, amino, hydrazine, thiosemicarbazone, hydrazine carboxylate and arylhydrazide.

In some examples, the linker is a cleavable linker, which facilitates release of the drug. Examples of cleavable linkers include acid-labile linkers (for example, comprising hydrazone), protease-sensitive linkers (for example, peptidase-sensitive), photolabile linkers, and disulfide-containing linkers (Chari et al., *Cancer Res* 52:127-131, 1992; U.S. Pat. No. 5,208,020).

The ADCs disclosed herein can be used for the treatment of a FGFR4-positive cancer alone or in combination with another therapeutic agent and/or in combination with any standard therapy for the treatment of cancer (such as surgical resection of the tumor, chemotherapy or radiation therapy).

VI. Chimeric Antigen Receptors (CARs)

The disclosed monoclonal antibodies can also be used to produce CARs (also known as chimeric T cell receptors, artificial T cell receptors or chimeric immunoreceptors) and/or cytotoxic T lymphocytes (CTLs) engineered to express CARs. Generally, CARs include a binding moiety, an extracellular hinge and spacer element, a transmembrane region and an endodomain that performs signaling functions (Cartellieri et al., *J Biomed Biotechnol* 2010:956304, 2010). In many instances, the binding moiety is an antigen binding fragment of a monoclonal antibody, such as a scFv. Several different endodomains have been used to generate CARs. For example, the endodomain can consist of a signaling chain having an ITAM, such as CD3ζ or FcεRIγ. In some instances, the endodomain further includes the intracellular portion of at least one additional co-stimulatory domain, such as CD28 and/or CD137.

CTLs expressing CARs can be used to target a specific cell type, such as a tumor cell. Thus, the monoclonal antibodies disclosed herein can be used to engineer CTLs that express a CAR containing an antigen-binding fragment of a FGFR4-specific antibody, thereby targeting the engineered CTLs to FGFR4-expressing tumor cells. Engineered T cells have previously been used for adoptive therapy for some types of cancer (see, for example, Park et al., *Mol Ther* 15(4):825-833, 2007). The use of T cells expressing CARs is more universal than standard CTL-based immunotherapy because CTLs expressing CARs are HLA unrestricted and can therefore be used for any patient having a tumor that expresses the target antigen.

Accordingly, provided herein are CARs that include a FGFR4-specific monoclonal antibody, or antigen-binding fragment thereof, such as a scFv. Also provided are isolated nucleic acid molecules and vectors encoding the CARs, and host cells, such as CTLs, expressing the CARs. CTLs expressing CARs comprised of a FGFR4-specific monoclonal antibody (or antibody binding fragment) can be used for the treatment of cancers that express FGFR4, such as rhabdomyosarcoma, lung cancer, liver cancer, breast cancer, pancreatic cancer and prostate cancer.

VII. Bispecific Antibodies

Bispecific antibodies are recombinant proteins comprised of antigen-binding fragments of two different monoclonal antibodies. Thus, bispecific antibodies bind two different antigens. Bispecific antibodies can be used for cancer immunotherapy by simultaneously targeting, for example, both CTLs (such as a CTL receptor component such as CD3) or effector natural killer (NK) cells, and a tumor antigen. The FGFR4-specific monoclonal antibodies disclosed herein can be used to generate bispecific antibodies that target both FGFR4 and CTLs, or targeting both FGFR4 and NK cells, thereby providing a means to treat FGFR4-expressing cancers.

Bi-specific T-cell engagers (BiTEs) are a type of bispecific monoclonal antibody that are fusions of a first single-chain variable fragment (scFv) that targets a tumor antigen and a second scFv that binds T cells, such as bind CD3 on T cells.

Bi-specific killer cell engagers (BiKEs) are a type of bispecific monoclonal antibody that are fusions of a first scFv that targets a tumor antigen and a second scFv that binds a NK cell activating receptor, such as CD16.

Provided herein are bispecific monoclonal antibodies comprising a FGFR4-specific monoclonal antibody, or antigen-binding fragment thereof. In some embodiments, the bispecific monoclonal antibody further comprises a monoclonal antibody, or antigen-binding fragment thereof, that specifically binds a component of the T cell receptor, such as CD3. In other embodiments, the bispecific monoclonal antibody further comprises a monoclonal antibody, or antigen-binding fragment thereof, that specifically binds a NK cell activating receptor, such as CD16, Ly49, or CD94. In some examples, the antigen-binding fragments are scFv. Also provided are isolated nucleic acid molecules and vectors encoding the bispecific antibodies, and host cells comprising the nucleic acid molecules or vectors. Bispecific antibodies comprising a FGFR4-specific antibody, or antigen-binding fragment thereof, can be used for the treatment of cancers that express FGFR4, such as rhabdomyosarcoma, lung cancer, liver cancer, breast cancer, pancreatic cancer and prostate cancer. Thus, provided herein are methods of treating a subject with cancer by selecting a subject with a cancer that expresses FGFR4, and administering to the subject a therapeutically effective amount of the FGFR4-targeting bispecific antibody.

VIII. Immunoconjugates

The disclosed monoclonal antibodies specific for FGFR4 can be conjugated to a therapeutic agent or effector molecule Immunoconjugates include, but are not limited to, molecules in which there is a covalent linkage of a therapeutic agent to an antibody. A therapeutic agent is an agent with a particular biological activity directed against a particular target molecule or a cell bearing a target molecule. One of skill in the art will appreciate that therapeutic agents can include various drugs such as vinblastine, daunomycin and the like, cytotoxins such as native or modified *Pseudomonas* exotoxin or diphtheria toxin, encapsulating agents (such as liposomes) that contain pharmacological compositions, radioactive agents such as $^{125}$I, $^{32}$P, $^{3}$H and $^{35}$S and other labels, target moieties and ligands.

The choice of a particular therapeutic agent depends on the particular target molecule or cell, and the desired biological effect. Thus, for example, the therapeutic agent can be a cytotoxin that is used to bring about the death of a particular target cell (such as a tumor cell). Conversely, where it is desired to invoke a non-lethal biological response, the therapeutic agent can be conjugated to a non-lethal pharmacological agent or a liposome containing a non-lethal pharmacological agent.

With the therapeutic agents and antibodies described herein, one of skill can readily construct a variety of clones containing functionally equivalent nucleic acids, such as nucleic acids which differ in sequence but which encode the same effector moiety or antibody sequence. Thus, the present disclosure provides nucleic acids encoding antibodies and conjugates and fusion proteins thereof.

Effector molecules can be linked to an antibody of interest using any number of means known to those of skill in the art. Both covalent and noncovalent attachment means may be used. The procedure for attaching an effector molecule to an antibody varies according to the chemical structure of the effector. Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody is derivatized to expose or attach additional reactive functional groups. The derivatization may involve attachment of any of a number of known linker molecules. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody and the effector molecule are polypeptides, the linkers may be joined to the constituent amino acids through their side groups (such as through a disulfide linkage to cysteine) or to the alpha carbon amino and carboxyl groups of the terminal amino acids.

In some circumstances, it is desirable to free the effector molecule from the antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site.

In view of the large number of methods that have been reported for attaching a variety of radiodiagnostic compounds, radiotherapeutic compounds, labels (such as enzymes or fluorescent molecules), drugs, toxins, and other agents to antibodies one skilled in the art will be able to determine a suitable method for attaching a given agent to an antibody or other polypeptide.

The antibodies or antibody fragments disclosed herein can be derivatized or linked to another molecule (such as another peptide or protein). In general, the antibodies or portion thereof is derivatized such that the binding to the target antigen is not affected adversely by the derivatization or labeling. For example, the antibody can be functionally linked (by chemical coupling, genetic fusion, noncovalent association or otherwise) to one or more other molecular entities, such as another antibody (for example, a bispecific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, such as to create bispecific antibodies). Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available.

The antibody can be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP) and yellow fluorescent protein (YFP). An antibody or antigen binding fragment can also be conjugated with enzymes that are useful for detection, such as horseradish peroxidase, (3-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

An antibody may be labeled with a magnetic agent, such as gadolinium. Antibodies can also be labeled with lanthanides (such as europium and dysprosium), and manganese. Paramagnetic particles such as superparamagnetic iron oxide are also of use as labels. An antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

An antibody can also be labeled with a radiolabeled amino acid. The radiolabel may be used for both diagnostic and therapeutic purposes. For instance, the radiolabel may be used to detect FGFR4 by x-ray, emission spectra, or other diagnostic techniques. Examples of labels for polypeptides include, but are not limited to, the following radioisotopes or radionucleotides: $^{3}$H, $^{14}$C, $^{15}$N, $^{35}$S, $^{90}$Y, $^{99}$Tc, $^{111}$In, $^{125}$I, $^{131}$I.

An antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

Toxins can be employed with the monoclonal antibodies described herein to produce immunotoxins. Exemplary toxins include ricin, abrin, diphtheria toxin and subunits thereof, as well as botulinum toxins A through F. These toxins are readily available from commercial sources (for example, Sigma Chemical Company, St. Louis, Mo.). Contemplated toxins also include variants of the toxins described herein (see, for example, see, U.S. Pat. Nos. 5,079,163 and 4,689,401). In one embodiment, the toxin is Pseudomonas exotoxin (PE) (U.S. Pat. No. 5,602,095). As used herein "Pseudomonas exotoxin" refers to a full-length native (naturally occurring) PE or a PE that has been modified. Such modifications can include, but are not limited to, elimination of domain Ia, various amino acid deletions in domains Ib, II and III, single amino acid substitutions and the addition of one or more sequences at the carboxyl terminus (for example, see Siegall et al., *J. Biol. Chem.* 264:14256-14261, 1989).

PE employed with the monoclonal antibodies described herein can include the native sequence, cytotoxic fragments of the native sequence, and conservatively modified variants of native PE and its cytotoxic fragments. Cytotoxic fragments of PE include those which are cytotoxic with or without subsequent proteolytic or other processing in the target cell. Cytotoxic fragments of PE include PE40, PE38, and PE35. For additional description of PE and variants thereof, see for example, U.S. Pat. Nos. 4,892,827; 5,512,658; 5,602,095; 5,608,039; 5,821,238; 5,854,044; PCT Publication Nos. WO 99/51643 and WO 2014/052064; Pai et al., *Proc. Natl. Acad. Sci. USA* 88:3358-3362, 1991; Kondo et al., *J. Biol. Chem.* 263:9470-9475, 1988; Pastan et al., *Biochim. Biophys. Acta* 1333:C1-C6, 1997.

Also contemplated herein are protease-resistant PE variants and PE variants with reduced immunogenicity, such as, but not limited to PE-LR, PE-6X, PE-8X, PE-LR/6X and PE-LR/8X (see, for example, Weldon et al., *Blood* 113(16): 3792-3800, 2009; Onda et al., *Proc Natl Acad Sci USA* 105(32):11311-11316, 2008; and PCT Publication Nos. WO 2007/016150, WO 2009/032954 and WO 2011/032022, which are herein incorporated by reference).

In some examples, the PE is a variant that is resistant to lysosomal degradation, such as PE-LR (Weldon et al., *Blood* 113(16):3792-3800, 2009; PCT Publication No. WO 2009/032954). In other examples, the PE is a variant designated PE-LR/6X (PCT Publication No. WO 2011/032022). In other examples, the PE variant is PE with reducing immunogenicity. In yet other examples, the PE is a variant designated PE-LR/8M (PCT Publication No. WO 2011/032022).

Modification of PE may occur in any previously described variant, including cytotoxic fragments of PE (for example, PE38, PE-LR and PE-LR/8M). Modified PEs may include any substitution(s), for one or more amino acid residues within one or more T-cell epitopes and/or B cell epitopes of PE.

The antibodies described herein can also be used to target any number of different diagnostic or therapeutic compounds to cells expressing FGFR4 on their surface. Thus, an antibody of the present disclosure can be attached directly or via a linker to a drug that is to be delivered directly to cells expressing cell-surface FGFR4. This can be done for therapeutic, diagnostic or research purposes. Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides.

Alternatively, the molecule linked to an anti-FGFR4 antibody can be an encapsulation system, such as a liposome or micelle that contains a therapeutic composition such as a drug, a nucleic acid (for example, an antisense nucleic acid), or another therapeutic moiety that is preferably shielded from direct exposure to the circulatory system. Means of preparing liposomes attached to antibodies are well known to those of skill in the art (see, for example, U.S. Pat. No. 4,957,735; Connor et al., *Pharm. Ther.* 28:341-365, 1985).

Antibodies described herein can also be covalently or non-covalently linked to a detectable label. Detectable labels suitable for such use include any composition detectable by spectroscopic, photochemical, biochemical, immunochemical, electrical, optical or chemical means. Useful labels include magnetic beads, fluorescent dyes (for example, fluorescein isothiocyanate, Texas red, rhodamine, green fluorescent protein, and the like), radiolabels (for example, 3H, $^{125}$I, $^{35}$S, $^{14}$C, or $^{32}$P), enzymes (such as horseradish peroxidase, alkaline phosphatase and others commonly used in an ELISA), and colorimetric labels such as colloidal gold or colored glass or plastic (such as polystyrene, polypropylene, latex, and the like) beads.

Means of detecting such labels are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

IX. Immunoliposomes

Immunoliposomes are antibody-conjugated liposomes that can be used to deliver cytotoxic agents or other anti-cancer agents directly to tumor cells via binding of the antibody to a tumor specific antigen expressed on the surface of tumor cells.

The liposomal component of an immunoliposome is typically a lipid vesicle of one or more concentric phospholipid bilayers. In some cases, the phospholipids are composed of a hydrophilic head group and two hydrophobic chains to enable encapsulation of both hydrophobic and hydrophilic drugs. Conventional liposomes are rapidly removed from the circulation via macrophages of the reticuloendothelial system (RES). To generate long-circulating liposomes, the composition, size and charge of the liposome can be modulated. The surface of the liposome may also be modified, such as with a glycolipid or sialic acid. For example, the inclusion of polyethylene glycol (PEG) significantly increases circulation half-life. Liposomes for use as drug delivery agents, including for preparation of immunoliposomes, have been described in the art (see, for example, Paszko and Senge, *Curr Med Chem* 19(31)5239-5277, 2012; Immordino et al., *Int J Nanomedicine* 1(3):297-315, 2006; U.S. Patent Application Publication Nos. 2011/0268655; 2010/00329981).

Antibodies or antibody fragments can be conjugated to a suitable liposome according to standard methods known in the art. For example, conjugation can be either covalent or noncovalent. In some embodiments, the antibody or antibody fragment is attached to a sterically stabilized, long circulation liposome via a PEG chain. Coupling of antibodies or antibody fragments to a liposome can also involve thioester bonds, for example by reaction of thiols and maleimide groups. Cross-linking agents can be used to create sulfhydryl groups for attachment of antibodies or antibody fragments (Paszko and Senge, *Curr Med Chem* 19(31)5239-5277, 2012).

X. Compositions and Methods of Use

Compositions are provided that include one or more of the disclosed antibodies that bind (for example specifically bind) FGFR4 in a carrier. Compositions comprising ADCs, CARs (and CTLs comprising CARs), bispecific antibodies, immunoliposomes and immunoconjugates are also provided. The compositions can be prepared in unit dosage forms for administration to a subject. The amount and timing of administration are at the discretion of the treating clinician to achieve the desired outcome. The antibody, ADC, CAR, CTL, bispecific antibody, immunoliposome or immunoconjugate can be formulated for systemic or local (such as intra-tumor) administration. In one example, the antibody is formulated for parenteral administration, such as intravenous administration.

The compositions for administration can include a solution of the antibody, ADC, CAR, CTL, bispecific antibody, immunoliposome or immunoconjugate in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody (or ADC, CAR, bispecific antibody or immunoconjugate) per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science*, 19th ed., Mack Publishing Company, Easton, Pa. (1995).

Antibodies (or other therapeutic molecules) may be provided in lyophilized form and rehydrated with sterile water before administration, although they are also provided in sterile solutions of known concentration. The antibody solution is then added to an infusion bag containing 0.9% sodium chloride, USP, and in some cases administered at a dosage of from 0.5 to 15 mg/kg of body weight. Considerable experience is available in the art in the administration of antibody drugs, which have been marketed in the U.S. since the approval of RITUXAN™ in 1997. Antibodies, ADCs, CARs, bispecific antibodies, immunoliposomes or immunoconjugates can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995). Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992).

Polymers can be used for ion-controlled release of the antibody-based compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. Nos. 5,055,303; 5,188,837; 4,235, 871; 4,501,728; 4,837,028; 4,957,735; 5,019,369; 5,055, 303; 5,514,670; 5,413,797; 5,268,164; 5,004,697; 4,902, 505; 5,506,206; 5,271,961; 5,254,342 and 5,534,496).

A. Therapeutic Methods

The antibodies, compositions, CARs (and CTLs expressing CARs), ADCs, bispecific antibodies, immunoliposomes and immunoconjugates disclosed herein can be administered to slow or inhibit the growth of tumor cells or inhibit the metastasis of tumor cells, such as rhabdomyosarcoma, lung cancer, liver cancer, breast cancer, pancreatic cancer and prostate cancer cells. In these applications, a therapeutically effective amount of a composition is administered to a subject in an amount sufficient to inhibit growth, replication or metastasis of cancer cells, or to inhibit a sign or a symptom of the cancer. Suitable subjects may include those diagnosed with a cancer that expresses FGFR4, such as, but not limited to, rhabdomyosarcoma, lung cancer, liver cancer, breast cancer, pancreatic cancer and prostate cancer.

Provided herein is a method of treating a subject having a FGFR4-positive cancer by selecting a subject with a FGFR4-positive cancer and administering to the subject a therapeutically effective amount of an antibody, ADC, CAR (e.g. a CTL expressing a CAR), bispecific antibody, immunoconjugate, immunoliposome or composition disclosed herein. Also provided herein is a method of inhibiting tumor growth or metastasis of a FGFR4-positive cancer in a subject by selecting a subject with a FGFR4-positive cancer and administering to the subject a therapeutically effective amount of an antibody, ADC, CAR (e.g. a CTL expressing a CAR), bispecific antibody, immunoconjugate, immunoliposome or composition disclosed herein. In some embodiments, the FGFR4-positive cancer is rhabdomyosarcoma, lung cancer, liver cancer, breast cancer, pancreatic cancer or prostate cancer.

A therapeutically effective amount of a FGFR4-specific antibody, ADC, CAR (e.g. a CTL expressing a CAR), bispecific antibody, immunoconjugate, immunoliposome or composition will depend upon the severity of the disease and the general state of the patient's health. A therapeutically effective amount of the antibody-based composition is that which provides either subjective relief of a symptom(s) or an objectively identifiable improvement as noted by the clinician or other qualified observer.

Administration of the antibodies, ADCs, CARs, immunoconjugates, bispecific antibodies, immunoliposomes and compositions disclosed herein can also be accompanied by administration of other anti-cancer agents or therapeutic treatments (such as surgical resection of a tumor). Any suitable anti-cancer agent can be administered in combination with the antibodies, compositions and immunoconjugates disclosed herein. Exemplary anti-cancer agents include, but are not limited to, chemotherapeutic agents, such as, for example, mitotic inhibitors, alkylating agents, antimetabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and other antibodies that specifically target cancer cells.

Non-limiting examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Non-limiting examples of antimetabolites include folic acid analogs (such as methotrexate), pyrimidine analogs (such as 5-FU or cytarabine), and purine analogs, such as mercaptopurine or thioguanine.

Non-limiting examples of natural products include *vinca* alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitomycin C), and enzymes (such as L-asparaginase).

Non-limiting examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Non-limiting examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone). Examples of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

Non-limiting examples of immunomodulators that can be used include AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, and TNF (tumor necrosis factor; Genentech).

Another common treatment for some types of cancer is surgical treatment, for example surgical resection of the cancer or a portion of it. Another example of a treatment is radiotherapy, for example administration of radioactive material or energy (such as external beam therapy) to the tumor site to help eradicate the tumor or shrink it prior to surgical resection.

B. Methods for Diagnosis and Detection

Methods are provided herein for detecting expression of FGFR4 in vitro or in vivo. In some cases, FGFR4 expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has a FGFR4-positive cancer by contacting a sample from the subject with a monoclonal antibody disclosed herein; and detecting binding of the antibody to the sample. An increase in binding of the antibody to the sample as compared to binding of the antibody to a control sample identifies the subject as having a FGFR4-positive cancer.

In another embodiment, provided is a method of confirming a diagnosis of a FGFR4-positive cancer in a subject by contacting a sample from a subject diagnosed with a FGFR4-positive cancer with a monoclonal antibody disclosed herein; and detecting binding of the antibody to the sample. An increase in binding of the antibody to the sample as compared to binding of the antibody to a control sample confirms the diagnosis of a FGFR4-positive cancer in the subject.

In some examples of the disclosed methods, the monoclonal antibody is directly labeled.

In some examples, the methods further include contacting a second antibody that specifically binds the monoclonal antibody with the sample; and detecting the binding of the second antibody. An increase in binding of the second antibody to the sample as compared to binding of the second antibody to a control sample detects a FGFR4-positive cancer in the subject or confirms the diagnosis of a FGFR4-positive cancer in the subject.

In some cases, the cancer is rhabdomyosarcoma, lung cancer, liver cancer, breast cancer, pancreatic cancer or prostate cancer, or any other type of cancer that expresses FGFR4.

In some examples, the control sample is a sample from a subject without cancer. In particular examples, the sample is a blood or tissue sample.

In some cases, the antibody that binds (for example specifically binds) FGFR4 is directly labeled with a detectable label. In another embodiment, the antibody that binds (for example, specifically binds) FGFR4 (the first antibody) is unlabeled and a second antibody or other molecule that can bind the antibody that specifically binds FGFR4 is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody or secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}$I, $^{131}$I, $^{35}$S or $^{3}$H.

In an alternative embodiment, FGFR4 can be assayed in a biological sample by a competition immunoassay utilizing FGFR4 standards labeled with a detectable substance and an unlabeled antibody that specifically binds FGFR4. In this assay, the biological sample, the labeled FGFR4 standards and the antibody that specifically bind FGFR4 are combined and the amount of labeled FGFR4 standard bound to the unlabeled antibody is determined. The amount of FGFR4 in the biological sample is inversely proportional to the amount of labeled FGFR4 standard bound to the antibody that specifically binds FGFR4.

The immunoassays and method disclosed herein can be used for a number of purposes. In one embodiment, the antibody that specifically binds FGFR4 may be used to detect the production of FGFR4 in cells in cell culture. In another embodiment, the antibody can be used to detect the amount of FGFR4 in a biological sample, such as a tissue sample, or a blood or serum sample. In some examples, the FGFR4 is cell-surface FGFR4. In other examples, the FGFR4 is soluble FGFR4 (e.g. FGFR4 in a cell culture supernatant or soluble FGFR4 in a body fluid sample, such as a blood or serum sample).

In one embodiment, a kit is provided for detecting FGFR4 in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble FGFR4 protein or fragment. Kits for detecting a polypeptide will typically comprise a monoclonal antibody that specifically binds FGFR4, such as any of the antibodies disclosed herein. In some embodiments, an antibody fragment, such as a scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds FGFR4. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting FGFR4 in a biological sample generally includes the steps of contacting the biological sample with an antibody which specifically reacts, under immunologically reactive conditions, to a FGFR4 polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the monoclonal antibodies that bind FGFR4, as disclosed herein, can be used in these assays. Thus, the antibodies can be used in a conventional immunoassay, including, without limitation, an ELISA, an RIA, FACS, tissue immunohistochemistry, Western blot or immunoprecipitation.

The following examples are provided to illustrate certain particular features and/or embodiments. These examples should not be construed to limit the disclosure to the particular features or embodiments described.

EXAMPLES

Example 1: Development and Characterization of Anti-FGFR4 Monoclonal Antibodies as Therapeutic Agents Rhabdomyosarcoma (RMS) is the most common soft tissue sarcoma of childhood with two major subtypes—embryonal (ERMS) and alveolar (ARMS), and current treatment modalities have yielded event free 5-year survival in only 30% of the patients with high-risk disease. Therefore, there is a need for novel strategies to identify and validate clinically relevant targets for the treatment of RMS. The fibroblast growth factor receptor 4 (FGFR4) is a very attractive therapeutic target because: 1) the FGFR4 gene is over expressed in RMS, 2) it is crucial for survival, proliferation, metastasis and drug resistance, 3) activating mutations in the kinase domain lead to aggressive growth and poor survival in patients with alveolar RMS and 4) genetic or pharmacologic inhibition of FGFR4-mediated signaling inhibited tumor growth in vitro and in vivo. Recent reports have shown overexpression of FGFR4 in several other human pediatric and adult cancers including liver, lung, pancreas, ovary, prostate and breast cancer.

Table 2 provides a summary of five rabbit or mouse monoclonal antibodies that specifically bind FGFR4. All five antibodies detect FGFR4 protein by both ELISA and flow cytometry.

TABLE 2

Monoclonal antibodies against human FGFR4

| mAb Clone | Immunogen | Host Species | Isotype | Assay Positive |
|---|---|---|---|---|
| 29.2 | hFGFR4-ECD | Rabbit | IgG | ELISA, flow cytometer |
| 57.1 | hFGFR4-ECD | Rabbit | IgG | ELISA, flow cytometer |
| BT53 | hFGFR4 transfected cells | Mouse | IgGbk | ELISA, flow cytometer |
| 1G5 | hFGFR4-Fc | Mouse | ND | ELISA, flow cytometer |
| 3A11 | hFGFR4-Fc | Mouse | ND | ELISA, flow cytometer |

The affinity of two of the FGFR4-specific mAbs was tested using surface plasmon resonance. The results are shown in Table 3.

TABLE 3

Affinity measurements of anti-FGFR4 mAbs

| Ligand | Analyte (mAb) | $K_{on}$ [$10^4$ $S^{-1}M^{-1}$] | $K_{off}$ [$10^4$ $S^{-1}$] | Observed $K_D$ [$10^{-9}$ M] |
|---|---|---|---|---|
| 29.2 | FGFR4-ECD | 2.5 | 4.3 | 17 |
| 57.1 | FGFR4-ECD | 0.17 | 1.8 | 110 |

Figure 1:
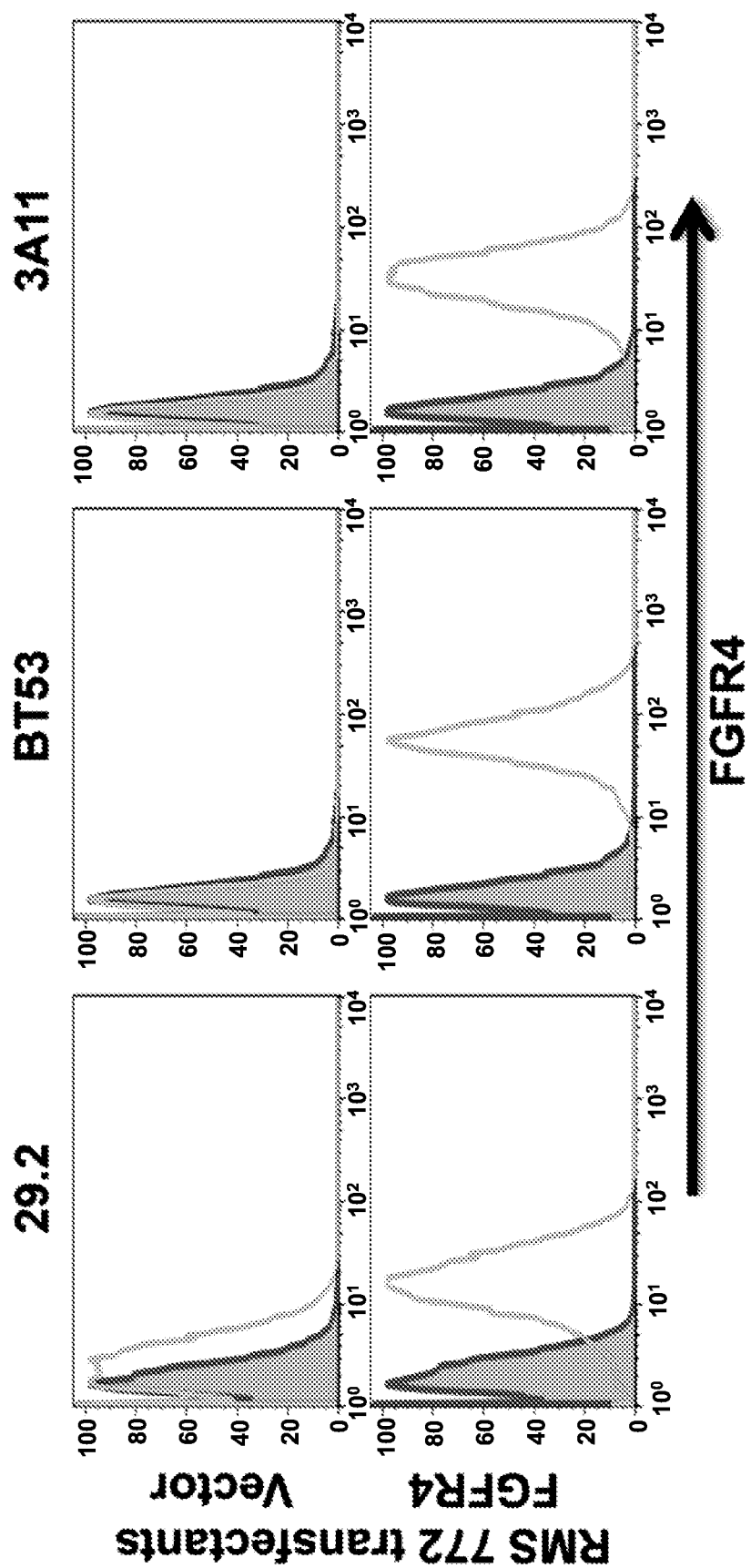
FIG. 1 is a series of flow cytometry plots showing the specificity of anti-FGFR4 mAbs binding to cell surface FGFR4. The murine RMS772 cell line was transfected with a plasmid containing the puromycin resistance gene alone (RMS772-puro) or a plasmid containing the puromycin resistance gene and the gene encoding full-length human wild type FGFR4 (RMS772-FGFR4). Cells grown in selection medium were stained with 1 µg/mL of anti-hFGFR4 monoclonal antibody from rabbit (29.2) or mouse (BT53, 3A11), and subsequently stained with fluorochrome-conjugated secondary antibody. Flow cytometry was performed using FACSCalibur. All three monoclonal antibodies exhibited significant binding to the FGFR4-transfected cells (non-filled histograms), but not to the vector control cells (filled histograms). Normal rabbit IgG and mouse IgG were used as isotype controls.

The mAb was immobilized in a CMS chip and the binding of FGFR4 extracellular domain (FGFR4-ECD) was detected by measuring surface plasmon resonance in a BIACORE™ instrument The specificity of anti-FGFR4 monoclonal antibodies 29.2, BT53 and 3A11 for binding cell surface FGFR4 was evaluated by flow cytometry. The murine RMS772 cell line was transfected with a control plasmid (RMS772-puro) or a plasmid encoding full-length human wild type FGFR4 (RMS772-FGFR4). Both plasmids contained a puromycin resistance gene. Cells grown in puromycin selection medium were stained with 1 µg/mL anti-hFGFR4 mAbs from rabbit (29.2) or mouse (BT53, 3A11), and subsequently stained with fluorochrome-conjugated secondary (anti-mouse or anti-rabbit as appropriate) antibody. Flow cytometry was performed using FACSCalibur. As shown in FIG. 1, all the three mAbs exhibited significant binding to the FGFR4 transfected cells, but not to the vector control cells.

A similar experiment was carried out to evaluate binding of FGFR4-specific mAbs to two well-characterized RMS cell lines, each cell line representing one of the two subtypes of the disease. Binding of 29.2, BT53 and 3A11 to RD cells (representing ERMS) and RH30 cells (representing ARMS) was evaluated by flow cytometry. All three antibodies bound to both cell types.

Eight ARMS cell lines and six ERMS cell lines were tested for cell surface expression of FGFR4. The values listed in Table 4 represent mean fluorescence intensity (MFI) obtained with individual mAbs minus the MFI obtained with corresponding isotype controls for each cell line. The mAbs were used at different concentrations and the values obtained with the optimal concentration (1-2 µg/mL).

TABLE 4

Comparison of FGFR4 expression between ERMS and ARMS cell lines

| Cell Line | Fusion Gene | Subtype | 29.2* | BT53* | 3A11* |
|---|---|---|---|---|---|
| Birch | Negative | Embryonal | 15.0 | 5.3 | 3.6 |
| CT10 | Negative | Embryonal | 6.6 | 13.9 | 10.1 |
| RD | Negative | Embryonal | 44.8 | 12.1 | 4.0 |
| Rh36 | Negative | Embryonal | 20.6 | 0.2 | 0.2 |
| TTC442 | Negative | Embryonal | 12.9 | 0.6 | 0.1 |
| JR.seq | PAX3/FOX01 | Embryonal | 20.2 | 51.2 | 36.3 |
| RJ3.UK | PAX3/FOX01 | Alveolar | 22.3 | 16.9 | 11.9 |
| Rh30 | PAX3/FOX01 | Alveolar | 69.2 | 34.7 | 17.6 |
| Rh41 | PAX3/FOX01 | Alveolar | 22.9 | 8.2 | 5.3 |
| Rh41.UK | PAX3/FOX01 | Alveolar | 15.6 | 14.0 | 9.2 |
| Rh5.UK | PAX3/FOX01 | Alveolar | 13.0 | 13.2 | 8.9 |
| Rh5 | PAX3/FOX01 | Alveolar | 17.0 | 3.2 | 2.1 |
| SCMC.UK | PAX3/FOX01 | Alveolar | 12.9 | 10.2 | 7.1 |
| T91-95.UK | PAX7/FOX01 | Alveolar | 58.1 | 0.2 | 0.1 |

*ΔMFI with indicated mAb

FGFR4 expression was also evaluated in fresh and short-term cultured ARMS tumor cells. Fresh tumor cells isolated from a metastatic breast nodule of a patient with ARMS were incubated with rabbit IgG (as a control) or the FGFR4-specific mAb 29.2, and subsequently stained with fluorochrome-conjugated goat anti-rabbit IgG. The fresh tumor cells exhibited low levels of FGFR4 expression. The tumor cells were also cultured for about one month in the presence of irradiated fibroblasts (3T3-J2) and ROCK inhibitor Y-27632. The cultured cells were harvested and stained for FGFR4 as described above. The short-term cultured ARMS tumor cells exhibited higher levels of FGFR4 expression than the fresh tumor cells.

In another study, binding of anti-FGFR4 monoclonal antibodies to RMS cell lines RH30 and RD was evaluated. Each RMS cell line was incubated with increasing concentrations of mAb 29.2 (0, 0.0001, 0.001, 0.01, 0.1, 1 and 10 µg/ml) or mAb BT53 (0, 0.00032, 0.0016, 0.008, 0.04, 0.2 and 1 µg/ml). Significant binding was observed with as little as 10 ng/mL of mAb. The results also demonstrated that ARMS cell lines expressed higher levels of cell surface FGFR4 than the ERMS cell lines.

To determine whether cell-surface binding of the FGFR4-specific mAbs leads to FGFR4 internalization, the follow study was carried out. RMS cell lines (RMS772-WtFGFR4, RH30, RH41, RD and CT10) were incubated with saturating amounts of mAb 29.2 or BT53 at 40° C. After washing, the cells were kept at 40° C. or further incubated at 37° C. for 0, 15, 30, 60 or 120 minutes in the presence of 10 µM phenylarsine oxide (PAO), an inhibitor of receptor-mediated endocytosis, or its diluent DMSO, or medium only. Subsequently, all cells were stained with an appropriate (anti-rabbit or anti-mouse) fluorochrome-conjugated secondary antibody. As shown in FIG. 2, binding of 29.2 or BT53 led to FGFR4 internalization.

Conclusions

The cell surface expression of FGFR4 protein in well characterized RMS cell lines, as well as in freshly isolated tumor cells from a patient, indicates that FGFR4 can serve as a therapeutic target for antibody-mediated intervention of RMS. The specificity of the anti-FGFR4 mAbs described herein indicates that one or more of these mAbs can be developed into a therapeutic agent. The finding that cell-surface FGFR4 facilitated rapid internalization of the membrane bound mAb encourages the development of antibody drug conjugates, immunotoxins and chimeric antigen receptor bearing T cells (CAR-T cells) and their evaluation as therapeutic agents.

Example 2: FGFR4 as a Therapeutic Target for Monoclonal Antibody Based Intervention in Rhabdomyosarcoma This example describes rabbit, mouse and human monoclonal antibodies that specifically bind FGFR4 and their characterization.

Two rabbit (29.2 and 57.1), three mouse (BT53, 3A11 and 1G5) and 10 human (M408, M409, M410, M412, M414, M415, M417, M418, M422 and M424) anti-FGFR4 monoclonal antibodies were identified. The immunogen used to develop the rabbit and human antibodies was hFGFR4-ECD. Mouse mAb BT53 was developed using hFGFR4-transfected cells as the antigen, while mouse mAbs 3A11 and 1G5 were generated using hFGFR4-Fc as the immunogen. The mouse and rabbit antibodies were produced using hybridoma technology. Using recombinant DNA technology, a human immunoglobulin library was selected using FGFR4 extracellular domain (FGFR4 ECD) to derive human anti-FGFR4 mAbs.

FGFR4 is overexpressed in RMS cell lines and RMS tumors in patients, compared to normal tissues. FGFR4 overexpression in RMS tumors and RMS xenograft tissue was further demonstrated by IHC on tissue microarrays. Rh30 (ARMS), Rh41 (ARMS), Rh18 (ERMS) and Rh36 (ERMS) tumor xenograft tissue exhibited positive staining with anti-FGFR4 mAb 29.2. RMS tumors from calf, cheek, intra-abdominal, nasopharynx, flank and nose tissue also stained positive by IHC using mAb 29.2.

FGFR4 expression was further evaluated in total lysates of normal tissue and RMS cell lines. As shown in FIG. 3, FGFR4 expression is significantly higher in RMS cell lines (RH30, RD, RHS, RH28 and RMS559) than in normal tissues (heart, stomach, bladder, lung, liver, cerebellum, pancreas, colon, kidney and spleen).

To evaluate cell-surface expression of FGFR4, the murine RMS772 cell line was transfected with a control plasmid (RMS772-puro) or with a plasmid expressing full-length human FGFR4 (RMS772-FGFR4). Both plasmids contained a puromycin resistance gene. Cells grown in puromycin selection medium were stained with 1 µg/mL anti-hFGFR4 mAbs from rabbit (29.2) or mouse (BT53), and subsequently stained with fluorochrome-conjugated secondary antibody. Flow cytometry was performed using FACSCalibur. All the three mAbs exhibited significant binding to the FGFR4 transfected cells, but not to the vector control cells. Normal rabbit IgG and mouse IgG were used as isotype controls. In addition, RMS cell lines were incubated with different amounts of anti-FGFR4 mAb 29.2 (0, 0.0001, 0.001, 0.01, 1 and 10 µg/ml) or mAb BT53 (0, 0.00032, 0.0016, 0.008, 0.04, 0.04 or 1 µg/ml). Significant binding was observed with as little as 10 ng/mL of each mAb. It was further noted that ARMS cell lines expressed higher levels of cell surface FGFR4 than the ERMS cell lines.

As described in Example 1, binding of anti-FGFR4 mAb induced internalization of cell-surface FGFR4. Therefore, an experiment was carried out to determine whether an anti-FGFR4 mAb conjugated to a secondary antibody-drug conjugate (ADC) could mediate cytotoxicity of RMS cells. RMS cell line RH30 was incubated with murine IgG or BT53 mAb at a concentration of 0.0001, 0.001, 0.01, 0.1, 1, 10 or 100 nM. Subsequently, secondary ADC (anti-mouse-Fc-drug) was added at 6.6 nM (FIG. 4). Dose-dependent cytotoxic activity was observed following the addition of secondary ADC. Among the two drugs tested, DMDM showed more potent activity than MMAF.

Conclusions

IHC analysis showed that FGFR4 is highly expressed in RMS cell lines and xenograft tissue compared to normal tissues. In addition, a different independent and more sensitive MSD assay also provided confirmation of high FGFR4 expression on RMS cell lines compared to normal tissues. The cell-surface expression of FGFR4 protein in well-characterized RMS cells indicates that FGFR4 can serve as a therapeutic target for antibody-mediated intervention of RMS. The specificity of the anti-FGFR4 mAbs disclosed herein indicate that these mAbs can be used as therapeutic agents. The data disclosed herein also demonstrated that cell-surface FGFR4 facilitated rapid internalization of the membrane-bound mAb and secondary ADC mediated cytotoxicity. Thus, the disclosed anti-FGFR4 mAbs can be used to develop ADCs for the treatment of RMS and other cancers expressing FGFR4.

Example 3: Cytotoxic Activity Mediated by FGFR4-Specific CARs

This example describes two FGFR4-specific CARs that include the scFv sequence of the 29.2 or 57.1 antibody and their cytotoxicity against FGFR4-positive cells.

The 29.2L and 57.1L CARs include an N-terminal signal peptide, the 29.2 scFv or 57.1 scFv sequences (respectively) and a CH2CH3 spacer. As shown in FIG. 5, transduced T cells are capable of expressing the FGFR4 CARs.

The FGFR4 CARs were evaluated in $^{51}$Cr release assays. The cytotoxicity of T cells expressing the FGFR4 CARs 29.2L and 57.1L (at 10 days post-activation) was evaluated. Percent lysis of rhabdomyosarcoma cells (RH41), osteosarcoma cells (143B) and myelogenous leukemia cells (K562) is shown in FIG. 6. Both FGFR4 CARs are cytotoxic against FGFR4-positive cells.

Example 4: Cytotoxic Activity Mediated by FGFR4-Specific Secondary ADCs

This example describes secondary ADCs comprising the anti-FGFR4 monoclonal antibodies BT53 and 3A11 and their cytotoxicity against FGFR4-expressing cells.

Secondary ADCs comprising BT53 or 3A11 bound to a secondary antibody conjugated to a drug (either MMAF or DMDM) were tested. As shown in FIG. 7, both secondary ADCs were cytotoxic to the FGFR4-positive RH30 cell line. FIG. 8 shows that the BT53 secondary ADCs were also cytotoxic to RMS-559 cells.

Next, the specificity of the FGFR4 ADCs was evaluated. The BT53 and 3A11 secondary ADCs comprising the drug DMDM were tested with FGFR4-positive rhabdomyosarcoma cells (RH30) and FGFR4-negative human skeletal muscle cells (SKMC) cells. The results are shown in FIG. 9. The FGFR4 secondary ADCs were cytotoxic only to the FGFR4 expressing cells. This finding was confirmed by evaluating the growth of FGFR4-positive RH30 cells and FGFR4-negative SKMC cells in the presence of the BT53 monoclonal antibody or the BT53 secondary ADC. As shown in FIG. 10A, the BT53 secondary ADC inhibited growth of the RH30 cells, while antibody alone did not. Neither the BT53 monoclonal antibody nor the BT53 secondary ADC inhibited growth of the FGFR4-negative SKMC cells (FIG. 10B).

Example 5: Cytotoxic Activity Mediated by FGFR4-Specific M410 and M412 CARs

This example describes three FGFR4-specific CARs that include the scFv sequences of either M410 or M412.

Three CARs were generated and tested: M410 long, M412 short and M412 long. Each of the FGFR4-specific CARs described in this example include a CD8 transmembrane domain, CD137 (4-1BB) signaling domain, and a CD3 zeta signaling domain (collectively having the amino acid sequence of SEQ ID NO: 66). The M410 long and M412 long CARs also include a linker domain composed of CH2CH3 (SEQ ID NO: 36).

T cells expressing the CARs were evaluated for their ability to induce cytotoxicity and IFN-γ release of FGFR4-expressing cells. Target RH30 (FGRR4+/CD22−) and Raji (FGFR4−/CD22+) cells were transduced with luciferase and the CELLTITER-GLO™ assay was used to measure the number of viable cells. A CD22-specific CAR was used as a control. Percent specific lysis induced by each CAR is shown in FIGS. 11A and 11B. FGFR4-specific CARs induced lysis of FGFR4-positive RH30 cells, but not FGFR4-negative Raji cells. The CD22-specific CAR was capable of inducing significant cell lysis of CD22+ Raji cells, but induced only low levels of lysis when tested with CD22-negative RH30 cells.

IFN-γ release induced by the FGFR4-specific CARs was also tested in RH30, Raji, SKES1 and K562 cells. SKES1 cells are a Ewing's sarcoma cells line with detectable (by Western blot) levels of FGFR4, but FGFR4 expression in these cells is not as high as in RH30 cells. K562 cells are FGFR4-negative. As shown in FIG. 12, M410 long induced the greatest level of IFN-γ release in FGFR4-positive cells. Background IFN-γ release was also observed on K562 cells. The CD22-specific CAR induced IFN-γ release of only CD22-positive Raji cells.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. An isolated monoclonal antibody that specifically binds fibroblast growth factor receptor 4 (FGFR4), or an antigen-binding fragment thereof, comprising a variable heavy (VH) domain and a variable light (VL) domain, wherein:
 the amino acid sequence of the VH domain of the antibody comprises the complementarity determining region 1 (CDR1), CDR2 and CDR3 sequences of SEQ ID NO: 3, wherein the CDR1, CDR2, and CDR3 sequences respectively comprise residues 26-33, 52-59, and 98-111 of SEQ ID NO:3; and
 the amino acid sequence of the VL domain of the antibody comprises the CDR1, CDR2 and CDR3 sequences of SEQ ID NO: 4, wherein the CDR1, CDR2, and CDR3 sequences respectively comprise residues 27-32, 50-52, and 88-98 of SEQ ID NO:4.

2. The monoclonal antibody or antigen-binding fragment of claim 1, wherein:
 the amino acid sequence of the VH domain is at least 90% identical to SEQ ID NO: 3 and the amino acid sequence of the VL domain is at least 90% identical to SEQ ID NO: 4.

3. The monoclonal antibody or antigen-binding fragment of claim 1, wherein:
 the amino acid sequence of the VH domain comprises SEQ ID NO: 3 and the amino acid sequence of the VL domain comprises SEQ ID NO: 4.

4. The antigen-binding fragment of claim 1, wherein the antigen-binding fragment is an Fab fragment, an Fab' fragment, an F(ab)'$_2$ fragment, a single chain variable fragment (scFv) or a disulfide stabilized variable fragment (dsFv).

5. The monoclonal antibody of claim 1, wherein the antibody is an IgG.

6. The monoclonal antibody or antigen-binding fragment of claim 1, which is a fully human antibody or antigen-binding fragment.

7. The monoclonal antibody or antigen-binding fragment of claim 1, which is a chimeric, synthetic, or humanized antibody or antigen-binding fragment.

8. A composition comprising the monoclonal antibody or antigen-binding fragment of claim 1 and a pharmaceutically acceptable carrier.

9. The antigen-binding fragment of claim 4, wherein the fragment is a scFv comprising the amino acid sequence of SEQ ID NO: 38.

* * * * *

SEQUENCE LISTING

<160> NUMBER OF SEQ ID NOS: 71

<210> SEQ ID NO 1
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 1

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Lys Ile Pro Val Tyr Gly Leu Glu Trp Ile
        35                  40                  45

Gly Ala Ile Asp Pro Glu Thr Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Val Arg Ser Leu Thr Ser Glu Asp Ser Ala Val Tyr Tyr Cys
                85                  90                  95

Thr Arg Gly Gly Tyr Tyr Gly Ser Asp Phe Asp Tyr Trp Gly Gln Gly
            100                 105                 110

Thr Thr Leu Thr Val Ser Ser
        115
```

<210> SEQ ID NO 2
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 2

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Asp Pro Tyr
                85                  90                  95

Thr Phe Gly Gly Gly Thr Lys Leu Glu Ile Lys
            100                 105

<210> SEQ ID NO 3
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 3

Gln Val Gln Leu Glu Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Asn Tyr Tyr Gly Ser Asp Tyr Asp Tyr Trp Gly Gln Gly
            100                 105                 110

Thr Thr Leu Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 4

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Lys Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Gln Thr Phe Gly Gly Gly Thr Lys Leu Glu Ile Lys
            100                 105                 110

<210> SEQ ID NO 5
<211> LENGTH: 111
<212> TYPE: PRT
<213> ORGANISM: Artificial Sequence
<220> FEATURE:
<223> OTHER INFORMATION: Synthetic polypeptide

<400> SEQUENCE: 5

Gln Val Gln Leu Gln Gln Ser Gly Ala Glu Leu Val Arg Pro Gly Ala
 1               5                  10                  15

Ser Val Thr Leu Ser Cys Lys Ala Ser Gly Tyr Thr Phe Thr Asp Tyr
                 20                  25                  30

Glu Met His Trp Val Lys Lys Ile Pro Val Tyr Gly Leu Glu Trp Ile
            35                  40                  45

Gly Ala Ile Asp Pro Glu Thr Gly Tyr Thr Ala Tyr Asn Gln Lys Phe
 50                  55                  60

Lys Gly Lys Ala Thr Leu Thr Ala Asp Lys Ser Ser Ser Thr Ala Tyr
 65                  70                  75                  80

Met Glu Val Arg Ser Leu Thr Ser Glu Asp Ser Ala Val Tyr Tyr Cys
                 85                  90                  95

Thr Arg Gly Gly Tyr Tyr Gly Ser Asp Phe Asp Tyr Trp Gly Gln
            100                 105                 110

<210> SEQ ID NO 6
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 6

Asp Ile Gln Met Asn Gln Ser Pro Ser Ser Leu Ser Ala Ser Leu Gly
 1               5                  10                  15

Asp Thr Ile Thr Ile Thr Cys His Ala Ser Gln Asn Ile Asn Val Trp
                 20                  25                  30

Leu Ser Trp Tyr Gln Gln Lys Pro Gly Asn Ile Pro Lys Leu Leu Ile
            35                  40                  45

Tyr Lys Ala Ser Asn Leu His Thr Gly Val Pro Ser Arg Phe Ser Gly
 50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Trp
                 85                  90                  95

Thr Phe Gly Gly Gly Thr Lys Leu Glu Ile Lys
            100                 105

```
<210> SEQ ID NO 7
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 7
```

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Asn Ser
            20                  25                  30

Val Gly Trp Val Arg Gln Ala Pro Gly Lys Gly Leu Glu Trp Ile Gly
            35                  40                  45

Ile Ile Ser Ser Ser Gly Asn Arg Tyr Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Gly Gly Asp Pro
                85                  90                  95

Val Ser Trp Tyr Gly Asp Ile Trp Gly Pro Gly Thr Leu Val Thr Val
            100                 105                 110

Ser Ser

```
<210> SEQ ID NO 8
<211> LENGTH: 135
<212> TYPE: PRT
<213> ORGANISM: Artificial Sequence
<220> FEATURE:
<223> OTHER INFORMATION: Synthetic polypeptide

<400> SEQUENCE: 8
```

Leu Leu Val Thr Ser Leu Leu Cys Glu Leu Pro His Pro Ala Phe
1               5                   10                  15

Leu Leu Ile Pro Asp Thr Glu Leu Val Leu Thr Gln Thr Pro Ser Ser
            20                  25                  30

Val Ser Ala Ala Val Gly Gly Thr Val Thr Ile Asn Cys Gln Ser Ser
            35                  40                  45

Pro Ser Leu Tyr Lys Asn Asn Tyr Leu Ser Trp Tyr Gln Gln Lys Pro
        50                  55                  60

Gly Gln Pro Pro Lys Leu Leu Ile Tyr Ser Ala Ser Thr Leu Ala Ser
65                  70                  75                  80

Gly Val Pro Ser Arg Phe Lys Gly Ser Gly Ser Gly Thr Glu Tyr Thr
                85                  90                  95

Leu Thr Ile Ser Gly Val Gln Cys Asp Asp Ala Ala Thr Tyr Tyr Cys
            100                 105                 110

Leu Gly Gly Tyr Ser Leu Ser Ser Asp Ser Pro Arg Ala Phe Gly Gly
            115                 120                 125

Gly Thr Glu Val Val Val Lys
    130                 135

```
<210> SEQ ID NO 9
<211> LENGTH: 118
<212> TYPE: PRT
<213> ORGANISM: Artificial Sequence
<220> FEATURE:
<223> OTHER INFORMATION: Synthetic polypeptide
```

-continued

```
<400> SEQUENCE: 9

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Met Ser Trp Val Arg Gln Ala Pro Glu Lys Gly Leu Glu Trp Ile Gly
        35                  40                  45

Ile Ile Tyr Ala Thr Ala Glu Thr Tyr Tyr Ala Thr Trp Ala Arg Gly
    50                  55                  60

Arg Phe Thr Ile Ser Lys Thr Ser Thr Thr Val Asp Leu Lys Ile Thr
65                  70                  75                  80

Ser Pro Ala Thr Glu Asp Thr Ala Thr Tyr Phe Cys Ala Arg Leu Asn
                85                  90                  95

Gly Asp Gly Ser Gly Thr Tyr Ala Tyr Asp Ile Trp Gly Pro Gly Thr
            100                 105                 110

Leu Val Thr Val Ser Ser
        115

<210> SEQ ID NO 10
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 10

Leu Leu Val Thr Ser Leu Leu Cys Glu Leu Pro His Pro Ala Phe
1               5                   10                  15

Leu Leu Ile Pro Asp Thr Glu Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

Gln Ser Ile Ser Ser Ser Tyr Leu Ser Trp Tyr Gln Gln Lys Pro Gly
    50                  55                  60

Gln Pro Pro Lys Leu Leu Ile Tyr Lys Ala Ser Thr Arg Pro Ser Gly
65                  70                  75                  80

Val Ser Ser Arg Phe Lys Gly Ser Gly Ser Gly Thr Gln Phe Thr Leu
                85                  90                  95

Thr Ile Ser Gly Val Gln Cys Ala Asp Ala Ala Thr Tyr Tyr Cys Leu
            100                 105                 110

Tyr Gly Tyr Tyr Ile Asp Ser Gly Ala Asp Asn Ser Phe Gly Gly Gly
        115                 120                 125

Thr Glu Val Val Val Lys
    130

<210> SEQ ID NO 11
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 11

Glu Val Gln Leu Val Gln Ser Gly Val Glu Gly Lys Lys Pro Glu Ala
1               5                   10                  15

Pro Val Lys Val Ser Cys Lys Ala Ser Gly Tyr Thr Phe Thr Asn Tyr
            20                  25                  30
```

```
Tyr Met His Trp Val Gln Gln Ala Pro Gly Lys Gly Leu Glu Trp Met
         35                  40                  45
Gly Leu Val Asp Pro Glu Asp Gly Glu Thr Ile Tyr Ala Glu Lys Phe
 50                  55                  60
Gln Gly Arg Val Thr Ile Thr Ala Asp Thr Ser Thr Asp Thr Ala Tyr
 65                  70                  75                  80
Met Glu Leu Ser Ser Leu Arg Ser Glu Asp Thr Ala Val Tyr Tyr Cys
                 85                  90                  95
Ala Arg Asp Pro Val Leu Leu Trp Asp Gly Met Asp Val Trp Gly Gln
                100                 105                 110
Gly Thr Thr
        115

<210> SEQ ID NO 12
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 12

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Thr Ile Ser Arg Tyr
                20                  25                  30
Leu Asn Trp Tyr Gln Gln Lys Pro Gly Lys Ala Pro Lys Leu Leu Ile
             35                  40                  45
Tyr Ala Ala Ser Ser Leu Gln Ser Gly Val Ser Ser Arg Phe Ser Gly
 50                  55                  60
Ser Gly Ser Gly Thr Glu Phe Thr Leu Thr Ile Ser Ser Leu Gln Pro
 65                  70                  75                  80
Glu Asp Phe Ala Thr Tyr Phe Cys Gln Gln Thr Tyr Ser Pro Pro Ile
                 85                  90                  95
Thr Phe Gly Gln Gly Thr Arg Leu Glu Ile Lys Arg
                100                 105

<210> SEQ ID NO 13
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 13

Ala Ala Gln Ala Ala Gln Val Gln Leu Gln Gln Ser Gly Pro Gly Leu
 1               5                  10                  15
Val Lys Pro Ser Gln Thr Leu Ser Leu Thr Cys Ala Ile Ser Gly Asp
                20                  25                  30
Ser Val Ser Ser Asn Ser Ala Ala Trp Asn Trp Ile Arg Gln Ser Pro
             35                  40                  45
Ser Arg Gly Leu Glu Trp Leu Gly Arg Thr Tyr Tyr Arg Ser Lys Trp
 50                  55                  60
Tyr Asn Asp Tyr Ala Val Ser Val Lys Ser Arg Ile Thr Ile Asn Pro
 65                  70                  75                  80
Asp Ala Ser Lys Asn Gln Phe Ser Leu Gln Leu Asn Ser Val Thr Pro
                 85                  90                  95
```

```
Glu Asp Thr Ala Val Tyr Tyr Cys Ser Gly Ser Tyr Ser Thr Phe Asp
                100                 105                 110

Ile Trp Gly Gln Gly Thr Met
            115
```

<210> SEQ ID NO 14
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 14

```
Asn Phe Met Leu Thr Gln Pro His Ser Val Ser Gly Ser Pro Gly Lys
1               5                   10                  15

Thr Val Thr Leu Ser Cys Thr Cys Ser Gly Gly Asn Ile Ala Asp Ala
            20                  25                  30

Tyr Val Gln Trp Tyr Gln Gln Arg Pro Gly Ser Ala Pro Arg Ile Val
        35                  40                  45

Ile Tyr Glu Asp Lys Gln Arg Pro Ser Gly Val Pro Asp Arg Phe Ser
    50                  55                  60

Gly Ser Ile Asp Ser Ser Ser Asn Ser Ala Ser Leu Thr Ile Ser Gly
65                  70                  75                  80

Leu Arg Thr Glu Asp Glu Ala Asp Tyr Tyr Cys Gln Ser Tyr Asp Thr
                85                  90                  95

Asn Asn Phe Trp Val Phe Gly Gly Gly Thr Lys Leu Thr Val Leu Gly
            100                 105                 110
```

<210> SEQ ID NO 15
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 15

```
Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Thr Ile Pro Tyr Tyr Asp Tyr Val Glu Asp Tyr Tyr Gly
            100                 105                 110

Met Asp Val Trp Gly Gln Gly Thr Thr
        115                 120
```

<210> SEQ ID NO 16
<211> LENGTH: 112
<212> TYPE: PRT
<213> ORGANISM: Artificial Sequence
<220> FEATURE:
<223> OTHER INFORMATION: Synthetic polypeptide

```
<400> SEQUENCE: 16

Asn Phe Met Leu Thr Gln Pro His Ser Val Ser Glu Ser Pro Gly Arg
1               5                   10                  15

Thr Val Ser Ile Ser Cys Thr Arg Gly Ser Gly Ser Ile Ala Asp Asp
            20                  25                  30

Tyr Val Gln Trp Tyr Gln Gln Arg Pro Gly Gly Ser Pro Thr Ile Val
        35                  40                  45

Ile Tyr Glu Asp Asn Gln Arg Pro Ser Gly Val Pro Asp Arg Phe Ser
50                  55                  60

Gly Ser Ile Asp Thr Ser Ser Asn Ser Ala Ser Leu Thr Ile Ser Gly
65                  70                  75                  80

Leu Thr Thr Glu Asp Glu Ala Val Tyr Tyr Cys Gln Ser Tyr Asp Tyr
                85                  90                  95

Arg Asp His Trp Val Phe Gly Gly Gly Thr Gln Leu Thr Val Leu Gly
            100                 105                 110

<210> SEQ ID NO 17
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 17

Gln Ala Ala Gln Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Val Ile Tyr Ser Gly Gly Ser Thr Tyr Tyr Ala Asp
50                  55                  60

Ser Val Lys Gly Arg Phe Thr Met Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Val Gly Leu Gln Ser Gly Ala Phe Asp Ile Trp Gly
            100                 105                 110

Gln Gly Thr Thr
        115

<210> SEQ ID NO 18
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Tyr Thr Tyr
            20                  25                  30

Leu Asn Trp Tyr Gln Gln Lys Pro Gly Lys Ala Pro Met Leu Val Ile
        35                  40                  45

His Asp Thr Ser Asn Leu Glu Thr Gly Ala Pro Ser Arg Phe Ser Gly
50                  55                  60
```

```
Gly Gly Ser Gly Thr Asp Phe Ser Phe Thr Ile Ser Ser Leu Gln Pro
65                  70                  75                  80

Glu Asp Phe Ala Thr Tyr Tyr Cys Gln Gln Tyr Asp Ala Leu Pro Phe
                85                  90                  95

Thr Phe Gly Gln Gly Thr Lys Leu Glu Ile Lys Arg
            100                 105
```

<210> SEQ ID NO 19
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 19

```
Glu Val Gln Leu Val Gln Phe Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Gly Glu Gly Leu Gly Ala Ile Asp Gly Phe Asp
                100                 105                 110

Ile Trp Gly Gln Gly Thr Thr
            115
```

<210> SEQ ID NO 20
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Ala Cys Arg Ala Ser Gln Thr Ile Ser Arg Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Gln Gln Thr Tyr Ser Pro Pro Ile
                85                  90                  95

Thr Phe Gly Gln Gly Thr Arg Leu Glu Ile Lys Arg
            100                 105
```

<210> SEQ ID NO 21
<211> LENGTH: 118
<212> TYPE: PRT
<213> ORGANISM: Artificial Sequence

```
<220> FEATURE:
<223> OTHER INFORMATION: Synthetic polypeptide

<400> SEQUENCE: 21

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Trp Pro Glu Tyr Ser Ser Ser Ala Asp Ala Phe Asp Ile
            100                 105                 110

Trp Gly Gln Gly Thr Met
            115

<210> SEQ ID NO 22
<211> LENGTH: 118
<212> TYPE: PRT
<213> ORGANISM: Artificial Sequence
<220> FEATURE:
<223> OTHER INFORMATION: Synthetic polypeptide

<400> SEQUENCE: 22

Asp Ile Gln Leu Thr Gln Ser Pro Ser Ser Leu Ser Ala Ser Val Gly
1               5                   10                  15

Asp Arg Val Thr Ile Thr Cys Gln Ala Ser Gln Asp Ile Asp Asn Tyr
            20                  25                  30

Leu Asn Trp Phe Gln Gln Lys Pro Gly Lys Pro Pro Lys Leu Leu Ile
        35                  40                  45

Ser Asp Ala Ser Ser Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Phe Pro Ile
                85                  90                  95

Thr Phe Gly Gln Gly Thr Lys Leu Glu Ile Lys Arg Gly Gln Ala Gly
            100                 105                 110

Gln Gly Pro Asp Lys Thr
            115

<210> SEQ ID NO 23
<211> LENGTH: 110
<212> TYPE: PRT
<213> ORGANISM: Artificial Sequence
<220> FEATURE:
<223> OTHER INFORMATION: Synthetic polypeptide

<400> SEQUENCE: 23

Glu Val Gln Leu Val Glu Ser Gly Gly Ala Leu Val Gln Pro Gly Gly
1               5                   10                  15

Ser Leu Arg Leu Ser Cys Ala Ala Ser Gly Phe Thr Phe Thr Asn Tyr
            20                  25                  30
```

Gly Ile Ile Trp Val Arg Gln Ala Pro Gly Lys Gly Glu Trp Val
            35                  40                  45

Ser Gly Val Ser Gly Asn Ala Val His Thr Tyr Tyr Ala Asp Ser Val
 50                  55                  60

Lys Gly Arg Phe Thr Ile Ser Arg Asp Asn Ser Lys Asn Met Val Tyr
 65                  70                  75                  80

Leu Gln Met Asn Ser Leu Arg Ser Asp Asp Thr Ala Val Tyr Tyr Cys
                 85                  90                  95

Ala Arg Gly Trp Asp Leu Asp Tyr Trp Gly Gln Gly Thr Leu
                100                 105                 110

<210> SEQ ID NO 24
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 24

Glu Ile Val Leu Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ile Gly
 50                  55                  60

Gly Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Asp Ser Leu Pro Leu
                 85                  90                  95

Ser Phe Gly Gly Gly Thr Lys Leu Glu Ile Lys Arg
                100                 105

<210> SEQ ID NO 25
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 25

Gln Leu Gln Leu Gln Glu Ser Gly Pro Gly Leu Val Lys Pro Ser Glu
 1               5                  10                  15

Thr Leu Ser Leu Thr Cys Val Val Phe Asp Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Asn Tyr Ser Gly Asn Thr Tyr Tyr Asn Pro Ser Leu
 50                  55                  60

Lys Ser Arg Val Thr Ile Ser Val Asp Thr Ser Lys Asn Gln Phe Ser
 65                  70                  75                  80

Leu Asn Leu Arg Ser Val Thr Ala Ala Asp Thr Ala Val Tyr Tyr Cys
                 85                  90                  95

Ala Arg Ser Val Asp Thr Ala Pro Gly Phe Asp Tyr Trp Gly Gln Gly
                100                 105                 110

Thr Leu

<210> SEQ ID NO 26
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 26

```
Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Leu Asp Ile Lys Arg
            100                 105
```

<210> SEQ ID NO 27
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 27

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Arg Ala Val Ala Gly Pro Gly Ala Phe Asp Ile Trp Gly
            100                 105                 110

Gln Gly Thr Met
        115
```

<210> SEQ ID NO 28
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 28

```
Glu Ile Val Leu Thr Gln Ser Pro Ser Ser Leu Ser Ala Ser Val Gly
1               5                   10                  15

Asp Arg Val Thr Ile Ala Cys Arg Ala Ser Gln Thr Ile Ser Arg Tyr
            20                  25                  30
```

```
Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Phe Cys Gln Gln Thr Tyr Ser Pro Pro Ile
                 85                  90                  95

Thr Phe Gly Gln Gly Thr Arg Leu Glu Ile Lys Arg
                100                 105
```

<210> SEQ ID NO 29
<211> LENGTH: 114
<212> TYPE: PRT
<213> ORGANISM: Artificial Sequence
<220> FEATURE:
<223> OTHER INFORMATION: Synthetic polypeptide

<400> SEQUENCE: 29

```
Gln Val Gln Leu Val Glu Thr Gly Gly Gly Val Val Gln Pro Gly Thr
 1               5                  10                  15

Ser Leu Arg Leu Ser Cys Ala Gly Ser Gly Phe Thr Phe Ser Glu Ser
             20                  25                  30

Gly Met His Trp Val Arg Gln Ala Pro Gly Lys Gly Leu Glu Trp Met
         35                  40                  45

Ala Leu Ile Leu Asn Asp Gly Ile Ser Asn Phe Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Ser Leu Gly Gly Asn Gly Ala Phe Asp Ile Trp Gly Gln Gly
                100                 105                 110

Thr Met
```

<210> SEQ ID NO 30
<211> LENGTH: 108
<212> TYPE: PRT
<213> ORGANISM: Artificial Sequence
<220> FEATURE:
<223> OTHER INFORMATION: Synthetic polypeptide

<400> SEQUENCE: 30

```
Asp Ile Gln Leu Thr Gln Ser Pro Ser Ser Leu Ser Ala Ser Val Gly
 1               5                  10                  15

Asp Arg Val Thr Ile Thr Cys Gln Ala Ser Gln Asp Ile Ser Asn Tyr
             20                  25                  30

Leu Asn Trp Tyr Gln Gln Lys Pro Gly Lys Ala Pro Lys Leu Leu Ile
             35                  40                  45

Tyr Asp Ala Ser Asn Leu Glu Ile Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln His Asp Asn Leu Pro Leu
                 85                  90                  95

Ser Phe Gly Gly Gly Thr Lys Leu Asp Ile Lys Arg
                100                 105
```

```
<210> SEQ ID NO 31
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 32

Val Thr Val Ser Ser Gly Gly Gly Ser Gly Gly Gly Ala Ser Ser
1               5                   10                  15

Gly Gly Gly Ser
            20

<210> SEQ ID NO 33
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 33

Val Thr Val Ser Ser Gly Gly Gly Ser Gly Gly Gly Ala Ser Gly
1               5                   10                  15

Gly Gly Gly Ser
            20

<210> SEQ ID NO 34
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 34

Leu Leu Val Thr Ser Leu Leu Leu Cys Glu Leu Pro His Pro Ala Phe
1               5                   10                  15

Leu Leu Ile Pro Asp Thr
            20

<210> SEQ ID NO 35
<211> LENGTH: 20
<212> TYPE: PRT
<213> ORGANISM: Artificial Sequence
<220> FEATURE:
<223> OTHER INFORMATION: Synthetic polypeptide

<400> SEQUENCE: 35

Lys Thr Thr Pro Pro Ser Val Tyr Gly Arg Val Lys Asp Pro Lys Ala
1               5                   10                  15

Ala Ala Ile Glu
            20
```

```
<210> SEQ ID NO 36
<211> LENGTH: 241
<212> TYPE: PRT
<213> ORGANISM: Artificial Sequence
<220> FEATURE:
<223> OTHER INFORMATION: Synthetic polypeptide

<400> SEQUENCE: 36
```

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp Pro Lys Ala Ala Ala Ile
225                 230                 235                 240

Glu

```
<210> SEQ ID NO 37
<211> LENGTH: 241
<212> TYPE: PRT
<213> ORGANISM: Artificial Sequence
<220> FEATURE:
<223> OTHER INFORMATION: Synthetic polypeptide

<400> SEQUENCE: 37
```

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Lys Ile Pro Val Tyr Gly Leu Glu Trp Ile
        35                  40                  45

Gly Ala Ile Asp Pro Glu Thr Tyr Gly Thr Ala Tyr Asn Gln Lys Phe
    50                  55                  60

```
Lys Gly Lys Ala Thr Leu Thr Ala Asp Lys Ser Ser Thr Ala Tyr
 65                  70                  75                  80

Met Glu Val Arg Ser Leu Thr Ser Glu Asp Ser Ala Val Tyr Tyr Cys
                 85                  90                  95

Thr Arg Gly Gly Tyr Tyr Gly Ser Asp Phe Asp Tyr Trp Gly Gln Gly
            100                 105                 110

Thr Thr Leu Thr Val Ser Ser Gly Gly Gly Ser Gly Gly Gly Gly
        115                 120                 125

Ser Gly Gly Gly Gly Ser Asn Ile Val Met Thr Gln Ser Pro Lys Ser
130                 135                 140

Met Ser Met Ser Val Gly Glu Arg Val Thr Leu Thr Cys Lys Ala Ser
145                 150                 155                 160

Glu Asn Val Val Thr Tyr Val Ser Trp Tyr Gln Gln Lys Pro Glu Gln
                165                 170                 175

Ser Pro Lys Leu Leu Ile Tyr Gly Ala Ser Asn Arg Tyr Thr Gly Val
            180                 185                 190

Pro Asp Arg Phe Thr Gly Ser Gly Ser Ala Thr Asp Phe Thr Leu Thr
            195                 200                 205

Ile Ser Ser Val Gln Ala Glu Asp Leu Ala Asp Tyr His Cys Gly Gln
210                 215                 220

Gly Tyr Ser Asp Pro Tyr Thr Phe Gly Gly Gly Thr Lys Leu Glu Ile
225                 230                 235                 240

Lys

<210> SEQ ID NO 38
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 38

Gln Val Gln Leu Glu Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Thr Arg Gly Asn Tyr Tyr Gly Ser Asp Tyr Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Asp Val Val Met Thr Gln Thr Pro Leu Thr
130                 135                 140

Leu Ser Val Thr Ile Gly Gln Pro Ala Ser Ile Ser Cys Lys Ser Ser
145                 150                 155                 160

Gln Ser Leu Leu Asp Ser Asp Gly Glu Thr Tyr Leu Asn Trp Leu Leu
                165                 170                 175
```

```
Lys Arg Pro Gly Gln Ser Pro Lys Arg Leu Ile Tyr Leu Val Ser Lys
            180                 185                 190

Leu Asp Ser Gly Val Pro Asp Arg Phe Thr Gly Ser Gly Ser Gly Thr
        195                 200                 205

Asp Phe Thr Leu Lys Ile Ser Arg Val Glu Ala Glu Asp Leu Gly Val
    210                 215                 220

Tyr Tyr Cys Trp Gln Gly Thr His Phe Pro Gln Thr Phe Gly Gly Gly
225                 230                 235                 240

Thr Lys Leu Glu Ile Lys
                245

<210> SEQ ID NO 39
<211> LENGTH: 233
<212> TYPE: PRT
<213> ORGANISM: Artificial Sequence
<220> FEATURE:
<223> OTHER INFORMATION: Synthetic polypeptide

<400> SEQUENCE: 39

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Lys Ile Pro Val Tyr Gly Leu Glu Trp Ile
        35                  40                  45

Gly Ala Ile Asp Pro Glu Thr Tyr Gly Thr Ala Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Glu Val Arg Ser Leu Thr Ser Glu Asp Ser Ala Val Tyr Tyr Cys
                85                  90                  95

Thr Arg Gly Gly Tyr Tyr Gly Ser Asp Phe Asp Tyr Trp Gly Gln Gly
            100                 105                 110

Gly Gly Gly Ser Gly Gly Gly Gly Ser Gly Gly Gly Gly Ser Asp Ile
        115                 120                 125

Gln Met Asn Gln Ser Pro Ser Ser Leu Ser Ala Ser Leu Gly Asp Thr
    130                 135                 140

Ile Thr Ile Thr Cys His Ala Ser Gln Asn Ile Asn Val Trp Leu Ser
145                 150                 155                 160

Trp Tyr Gln Gln Lys Pro Gly Asn Ile Pro Lys Leu Leu Ile Tyr Lys
                165                 170                 175

Ala Ser Asn Leu His Thr Gly Val Pro Ser Arg Phe Ser Gly Ser Gly
            180                 185                 190

Ser Gly Thr Gly Phe Thr Leu Thr Ile Ser Ser Leu Gln Pro Glu Asp
        195                 200                 205

Ile Ala Thr Tyr Tyr Cys Gln Gln Gly Gln Ser Tyr Pro Trp Thr Phe
    210                 215                 220

Gly Gly Gly Thr Lys Leu Glu Ile Lys
225                 230

<210> SEQ ID NO 40
<211> LENGTH: 242
<212> TYPE: PRT
<213> ORGANISM: Artificial Sequence
<220> FEATURE:
<223> OTHER INFORMATION: Synthetic polypeptide
```

<400> SEQUENCE: 40

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile Ser Trp Val Arg Gln Ala Pro Gly Gln Gly Leu Glu Trp Met
        35                  40                  45

Gly Gly Ile Asp Pro Glu Thr Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Gly Ser Asp Phe Asp Tyr Trp Trp Gly Gln
            100                 105                 110

Gly Thr Met Val Thr Val Ser Ser Gly Gly Gly Ser Gly Gly Gly
        115                 120                 125

Gly Ser Gly Gly Gly Ser Glu Ile Val Leu Thr Gln Ser Pro Ala
    130                 135                 140

Thr Leu Ser Leu Ser Pro Gly Glu Arg Ala Thr Leu Ser Cys Arg Ala
145                 150                 155                 160

Ser Glu Asn Val Val Thr Tyr Ala Trp Tyr Gln Gln Lys Pro Gly Gln
                165                 170                 175

Ala Pro Arg Leu Leu Ile Tyr Gly Ala Ser Arg Ala Thr Gly Ile Pro
            180                 185                 190

Ala Arg Phe Ser Gly Ser Gly Ser Gly Thr Asp Phe Thr Leu Thr Ile
        195                 200                 205

Ser Ser Leu Glu Pro Glu Asp Phe Ala Val Tyr Tyr Cys Gln Gln Gly
    210                 215                 220

Tyr Ser Asp Pro Tyr Thr Phe Phe Gly Gln Gly Thr Lys Leu Glu Ile
225                 230                 235                 240

Lys Arg
```

<210> SEQ ID NO 41
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 41

```
Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Glu Ile Ser Trp Val Arg Gln Ala Pro Gly Gln Gly Leu Glu Trp Met
        35                  40                  45

Gly Gly Ile Asp Pro Glu Thr Gly Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Asn Tyr Tyr Gly Ser Asp Tyr Asp Tyr Trp Trp Gly Gln
            100                 105                 110
```

Gly Thr Met Val Thr Val Ser Gly Gly Gly Ser Gly Gly Gly
            115                 120                 125

Gly Ser Gly Gly Gly Ser Glu Ile Val Leu Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Ser Leu Leu Asp Ser Asp Ala Trp Tyr Gln Lys Pro Gly
                165                 170                 175

Gln Ala Pro Arg Leu Leu Ile Tyr Leu Val Ser Arg Ala Thr Gly Ile
                180                 185                 190

Pro Ala Arg Phe Ser Gly Ser Gly Ser Gly Thr Asp Phe Thr Leu Thr
                195                 200                 205

Ile Ser Ser Leu Glu Pro Glu Asp Phe Ala Val Tyr Tyr Cys Trp Gln
210                 215                 220

Gly Thr His Phe Pro Gln Thr Phe Phe Gly Gln Gly Thr Lys Leu Glu
225                 230                 235                 240

Ile Lys Arg

<210> SEQ ID NO 42
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 42

Gln Val Gln Leu Gln Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Glu Ile Ser Trp Val Arg Gln Ala Pro Gly Gln Gly Leu Glu Trp Met
            35                  40                  45

Gly Gly Ile Asp Pro Glu Thr Tyr Gly Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Gly Ser Asp Phe Asp Tyr Trp Trp Gly Gln
            100                 105                 110

Gly Thr Met Val Thr Val Ser Ser Gly Gly Gly Ser Gly Gly Gly
            115                 120                 125

Gly Ser Gly Gly Gly Ser Glu Ile Val Leu Thr Gln Ser Pro Ala
130                 135                 140

Thr Leu Ser Leu Ser Pro Gly Glu Arg Ala Thr Leu Ser Cys Arg Ala
145                 150                 155                 160

Ser Gln Asn Ile Asn Val Trp Ala Trp Tyr Gln Gln Lys Pro Gly Gln
                165                 170                 175

Ala Pro Arg Leu Leu Ile Tyr Lys Ala Ser Arg Ala Thr Gly Ile Pro
                180                 185                 190

Ala Arg Phe Ser Gly Ser Gly Ser Gly Thr Asp Phe Thr Leu Thr Ile
                195                 200                 205

Ser Ser Leu Glu Pro Glu Asp Phe Ala Val Tyr Tyr Cys Gln Gln Gly
210                 215                 220

Gln Ser Tyr Pro Trp Thr Phe Phe Gly Gln Gly Thr Lys Leu Glu Ile
225                 230                 235                 240

Lys Arg

<210> SEQ ID NO 43
<211> LENGTH: 264
<212> TYPE: PRT
<213> ORGANISM: Artificial Sequence
<220> FEATURE:
<223> OTHER INFORMATION: Synthetic polypeptide

<400> SEQUENCE: 43

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Ser Asn Ser
                20                  25                  30

Val Gly Trp Val Arg Gln Ala Pro Gly Lys Gly Leu Glu Trp Ile Gly
            35                  40                  45

Ile Ile Ser Ser Ser Gly Asn Arg Tyr Tyr Ala Ser Trp Ala Lys Gly
        50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Gly Gly Asp Pro
                85                  90                  95

Val Ser Trp Tyr Gly Asp Ile Trp Gly Pro Gly Thr Leu Val Thr Val
            100                 105                 110

Ser Ser Gly Gly Gly Gly Ser Gly Gly Gly Ser Gly Gly Gly Gly
        115                 120                 125

Ser Leu Leu Val Thr Ser Leu Leu Cys Glu Leu Pro His Pro Ala
        130                 135                 140

Phe Leu Leu Ile Pro Asp Thr Glu Leu Val Leu Thr Gln Thr Pro Ser
145                 150                 155                 160

Ser Val Ser Ala Ala Val Gly Gly Thr Val Thr Ile Asn Cys Gln Ser
                165                 170                 175

Ser Pro Ser Leu Tyr Lys Asn Asn Tyr Leu Ser Trp Tyr Gln Gln Lys
            180                 185                 190

Pro Gly Gln Pro Pro Lys Leu Leu Ile Tyr Ser Ala Ser Thr Leu Ala
        195                 200                 205

Ser Gly Val Pro Ser Arg Phe Lys Gly Ser Gly Ser Gly Thr Glu Tyr
    210                 215                 220

Thr Leu Thr Ile Ser Gly Val Gln Cys Asp Asp Ala Ala Thr Tyr Tyr
225                 230                 235                 240

Cys Leu Gly Gly Tyr Ser Leu Ser Ser Asp Ser Pro Arg Ala Phe Gly
                245                 250                 255

Gly Gly Thr Glu Val Val Val Lys
            260

<210> SEQ ID NO 44
<211> LENGTH: 267
<212> TYPE: PRT
<213> ORGANISM: Artificial Sequence
<220> FEATURE:
<223> OTHER INFORMATION: Synthetic polypeptide

<400> SEQUENCE: 44

Gln Ser Val Lys Glu Ser Glu Gly Arg Leu Val Thr Pro Gly Thr Pro
1               5                   10                  15

Leu Thr Leu Thr Cys Thr Val Ser Gly Phe Ser Leu Ser Thr Tyr Ala
            20                  25                  30

Met Ser Trp Val Arg Gln Ala Pro Glu Lys Gly Leu Glu Trp Ile Gly
        35                  40                  45

Ile Ile Tyr Ala Thr Ala Glu Thr Tyr Tyr Ala Thr Trp Ala Arg Gly
50                  55                  60

Arg Phe Thr Ile Ser Lys Thr Ser Thr Thr Val Asp Leu Lys Ile Thr
65                  70                  75                  80

Ser Pro Ala Thr Glu Asp Thr Ala Thr Tyr Phe Cys Ala Arg Leu Asn
                85                  90                  95

Gly Asp Gly Ser Gly Thr Tyr Ala Tyr Asp Ile Trp Gly Pro Gly Thr
            100                 105                 110

Leu Val Thr Val Ser Ser Gly Gly Gly Ser Gly Gly Gly Gly Ser
        115                 120                 125

Gly Gly Gly Gly Ser Leu Leu Val Thr Ser Leu Leu Leu Cys Glu Leu
130                 135                 140

Pro His Pro Ala Phe Leu Leu Ile Pro Asp Thr Glu Leu Val Met Thr
145                 150                 155                 160

Gln Thr Pro Ser Pro Val Ser Ala Ala Val Gly Gly Thr Val Thr Ile
                165                 170                 175

Asn Cys Gln Ala Ser Gln Ser Ile Ser Ser Tyr Leu Ser Trp Tyr
            180                 185                 190

Gln Gln Lys Pro Gly Gln Pro Pro Lys Leu Leu Ile Tyr Lys Ala Ser
        195                 200                 205

Thr Arg Pro Ser Gly Val Ser Ser Arg Phe Lys Gly Ser Gly Ser Gly
210                 215                 220

Thr Gln Phe Thr Leu Thr Ile Ser Gly Val Gln Cys Ala Asp Ala Ala
225                 230                 235                 240

Thr Tyr Tyr Cys Leu Tyr Gly Tyr Tyr Ile Asp Ser Gly Ala Asp Asn
                245                 250                 255

Ser Phe Gly Gly Gly Thr Glu Val Val Val Lys
            260                 265

<210> SEQ ID NO 45
<211> LENGTH: 246
<212> TYPE: PRT
<213> ORGANISM: Artificial Sequence
<220> FEATURE:
<223> OTHER INFORMATION: Synthetic polypeptide

<400> SEQUENCE: 45

Gln Val Gln Leu Gln Gln Ser Gly Ala Glu Val Lys Lys Pro Gly Ser
1               5                   10                  15

Ser Val Lys Val Ser Cys Lys Ala Ser Gly Phe Ser Leu Ser Ser Asn
            20                  25                  30

Ser Ile Ser Trp Val Arg Gln Ala Pro Gly Gln Gly Leu Glu Trp Met
        35                  40                  45

Gly Gly Ile Ser Ser Ser Gly Asn Arg Asn Tyr Ala Gln Lys Phe Gln
50                  55                  60

Gly Arg Val Thr Ile Thr Ala Asp Glu Ser Thr Ser Thr Ala Tyr Met
65                  70                  75                  80

```
Glu Leu Ser Ser Leu Arg Ser Glu Asp Thr Ala Val Tyr Tyr Cys Gly
                85                  90                  95

Gly Asp Pro Val Ser Trp Tyr Gly Asp Ile Trp Trp Gly Gln Gly Thr
            100                 105                 110

Met Val Thr Val Ser Ser Gly Gly Gly Ser Gly Gly Gly Gly Ser
        115                 120                 125

Gly Gly Gly Gly Ser Glu Ile Val Leu Thr Gln Ser Pro Ala Thr Leu
130                 135                 140

Ser Leu Ser Pro Gly Glu Arg Ala Thr Leu Ser Cys Arg Ala Ser Pro
145                 150                 155                 160

Ser Leu Tyr Lys Asn Asn Tyr Ala Trp Tyr Gln Gln Lys Pro Gly Gln
                165                 170                 175

Ala Pro Arg Leu Leu Ile Tyr Ser Ala Ser Arg Ala Thr Gly Ile Pro
            180                 185                 190

Ala Arg Phe Ser Gly Ser Gly Ser Gly Thr Asp Phe Thr Leu Thr Ile
            195                 200                 205

Ser Ser Leu Glu Pro Glu Asp Phe Ala Val Tyr Tyr Cys Leu Gly Gly
        210                 215                 220

Tyr Ser Leu Ser Ser Asp Ser Pro Arg Ala Phe Phe Gly Gln Gly Thr
225                 230                 235                 240

Lys Leu Glu Ile Lys Arg
                245

<210> SEQ ID NO 46
<211> LENGTH: 249
<212> TYPE: PRT
<213> ORGANISM: Artificial Sequence
<220> FEATURE:
<223> OTHER INFORMATION: Synthetic polypeptide

<400> SEQUENCE: 46

Gln Val Gln Leu Gln Gln Ser Gly Ala Glu Val Lys Lys Pro Gly Ser
1               5                   10                  15

Ser Val Lys Val Ser Cys Lys Ala Ser Gly Phe Ser Leu Ser Thr Tyr
            20                  25                  30

Ala Ile Ser Trp Val Arg Gln Ala Pro Gly Gln Gly Leu Glu Trp Met
        35                  40                  45

Gly Gly Ile Tyr Ala Thr Ala Glu Thr Asn Tyr Ala Gln Lys Phe Gln
    50                  55                  60

Gly Arg Val Thr Ile Thr Ala Asp Glu Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Leu Asn Gly Asp Gly Ser Gly Thr Tyr Ala Tyr Asp Ile Trp Trp
            100                 105                 110

Gly Gln Gly Thr Met Val Thr Val Ser Ser Gly Gly Gly Ser Gly
            115                 120                 125

Gly Gly Gly Ser Gly Gly Gly Ser Glu Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Gln Ser Ile Ser Ser Tyr Ala Trp Tyr Gln Gln Lys
                165                 170                 175

Pro Gly Gln Ala Pro Arg Leu Leu Ile Tyr Lys Ala Ser Arg Ala Thr
            180                 185                 190
```

```
Gly Ile Pro Ala Arg Phe Ser Gly Ser Gly Ser Gly Thr Asp Phe Thr
            195                 200                 205

Leu Thr Ile Ser Ser Leu Glu Pro Glu Asp Phe Ala Val Tyr Tyr Cys
        210                 215                 220

Leu Tyr Gly Tyr Tyr Ile Asp Ser Gly Ala Asp Asn Ser Phe Phe Gly
225                 230                 235                 240

Gln Gly Thr Lys Leu Glu Ile Lys Arg
                245

<210> SEQ ID NO 47
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 47

Glu Val Gln Leu Val Gln Ser Gly Val Glu Gly Lys Lys Pro Glu Ala
1               5                   10                  15

Pro Val Lys Val Ser Cys Lys Ala Ser Gly Tyr Thr Phe Thr Asn Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Val Leu Leu Trp Asp Gly Met Asp Val Trp Gly Gln
            100                 105                 110

Gly Thr Thr Val Thr Val Ser Ser Gly Gly Gly Ser Gly Gly Gly
        115                 120                 125

Ala Ser Ser Gly Gly Gly Ser Asp Ile Gln Met Thr Gln Ser Pro Ser
    130                 135                 140

Ser Leu Ser Ala Ser Val Gly Asp Arg Val Thr Ile Thr Cys Arg Ala
145                 150                 155                 160

Ser Gln Thr Ile Ser Arg Tyr Leu Asn Trp Tyr Gln Gln Lys Pro Gly
                165                 170                 175

Lys Ala Pro Lys Leu Leu Ile Tyr Ala Ala Ser Ser Leu Gln Ser Gly
            180                 185                 190

Val Ser Arg Phe Ser Gly Ser Gly Ser Gly Thr Glu Phe Thr Leu
        195                 200                 205

Thr Ile Ser Ser Leu Gln Pro Glu Asp Phe Ala Thr Tyr Phe Cys Gln
    210                 215                 220

Gln Thr Tyr Ser Pro Pro Ile Thr Phe Gly Gln Gly Thr Arg Leu Glu
225                 230                 235                 240

Ile Lys Arg

<210> SEQ ID NO 48
<211> LENGTH: 251
<212> TYPE: PRT
<213> ORGANISM: Artificial Sequence
<220> FEATURE:
<223> OTHER INFORMATION: Synthetic polypeptide
```

-continued

<400> SEQUENCE: 48

Ala Ala Gln Ala Ala Gln Val Gln Leu Gln Gln Ser Gly Pro Gly Leu
1               5                   10                  15

Val Lys Pro Ser Gln Thr Leu Ser Leu Thr Cys Ala Ile Ser Gly Asp
            20                  25                  30

Ser Val Ser Ser Asn Ser Ala Ala Trp Asn Trp Ile Arg Gln Ser Pro
        35                  40                  45

Ser Arg Gly Leu Glu Trp Leu Gly Arg Thr Tyr Tyr Arg Ser Lys Trp
    50                  55                  60

Tyr Asn Asp Tyr Ala Val Ser Val Lys Ser Arg Ile Thr Ile Asn Pro
65                  70                  75                  80

Asp Ala Ser Lys Asn Gln Phe Ser Leu Gln Leu Asn Ser Val Thr Pro
                85                  90                  95

Glu Asp Thr Ala Val Tyr Tyr Cys Ser Gly Ser Tyr Ser Thr Phe Asp
            100                 105                 110

Ile Trp Gly Gln Gly Thr Met Val Thr Val Ser Ser Gly Gly Gly Gly
        115                 120                 125

Ser Gly Gly Gly Ala Ser Ser Gly Gly Gly Ser Asn Phe Met Leu Thr
    130                 135                 140

Gln Pro His Ser Val Ser Gly Ser Pro Gly Lys Thr Val Thr Leu Ser
145                 150                 155                 160

Cys Thr Cys Ser Gly Gly Asn Ile Ala Asp Ala Tyr Val Gln Trp Tyr
                165                 170                 175

Gln Gln Arg Pro Gly Ser Ala Pro Arg Ile Val Ile Tyr Glu Asp Lys
            180                 185                 190

Gln Arg Pro Ser Gly Val Pro Asp Arg Phe Ser Gly Ser Ile Asp Ser
        195                 200                 205

Ser Ser Asn Ser Ala Ser Leu Thr Ile Ser Gly Leu Arg Thr Glu Asp
    210                 215                 220

Glu Ala Asp Tyr Tyr Cys Gln Ser Tyr Asp Thr Asn Asn Phe Trp Val
225                 230                 235                 240

Phe Gly Gly Gly Thr Lys Leu Thr Val Leu Gly
                245                 250

<210> SEQ ID NO 49
<211> LENGTH: 253
<212> TYPE: PRT
<213> ORGANISM: Artificial Sequence
<220> FEATURE:
<223> OTHER INFORMATION: Synthetic polypeptide

<400> SEQUENCE: 49

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Thr Ile Pro Tyr Tyr Gly Asp Tyr Val Glu Asp Tyr Gly
            100                 105                 110

Met Asp Val Trp Gly Gln Gly Thr Thr Val Thr Val Ser Ser Gly Gly
        115                 120                 125

Gly Gly Ser Gly Gly Gly Ala Ser Ser Gly Gly Gly Ser Asn Phe Met
    130                 135                 140

Leu Thr Gln Pro His Ser Val Ser Glu Ser Pro Gly Arg Thr Val Ser
145                 150                 155                 160

Ile Ser Cys Thr Arg Gly Ser Gly Ser Ile Ala Asp Asp Tyr Val Gln
                165                 170                 175

Trp Tyr Gln Gln Arg Pro Gly Gly Ser Pro Thr Ile Val Ile Tyr Glu
            180                 185                 190

Asp Asn Gln Arg Pro Ser Gly Val Pro Asp Arg Phe Ser Gly Ser Ile
        195                 200                 205

Asp Thr Ser Ser Asn Ser Ala Ser Leu Thr Ile Ser Gly Leu Thr Thr
    210                 215                 220

Glu Asp Glu Ala Val Tyr Tyr Cys Gln Ser Tyr Asp Tyr Arg Asp His
225                 230                 235                 240

Trp Val Phe Gly Gly Gly Thr Gln Leu Thr Val Leu Gly
                245                 250

<210> SEQ ID NO 50
<211> LENGTH: 244
<212> TYPE: PRT
<213> ORGANISM: Artificial Sequence
<220> FEATURE:
<223> OTHER INFORMATION: Synthetic polypeptide

<400> SEQUENCE: 50

Gln Ala Ala Gln Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Val Ile Tyr Ser Gly Gly Ser Thr Tyr Tyr Ala Asp
    50                  55                  60

Ser Val Lys Gly Arg Phe Thr Met Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Val Gly Leu Gln Ser Gly Ala Phe Asp Ile Trp Gly
            100                 105                 110

Gln Gly Thr Thr Val Thr Val Ser Ser Gly Gly Gly Gly Ser Gly Gly
        115                 120                 125

Gly Ala Ser Gly Gly Gly Gly Ser Asp Ile Gln Met Thr Gln Ser Pro
    130                 135                 140

Ser Ser Leu Ser Ala Ser Val Gly Asp Arg Val Thr Ile Thr Cys Gln
145                 150                 155                 160

Ala Ser Gln Asp Ile Tyr Thr Tyr Leu Asn Trp Tyr Gln Gln Lys Pro
                165                 170                 175

Gly Lys Ala Pro Met Leu Val Ile His Asp Thr Ser Asn Leu Glu Thr
            180                 185                 190

Gly Ala Pro Ser Arg Phe Ser Gly Gly Gly Ser Gly Thr Asp Phe Ser
        195                 200                 205

```
Phe Thr Ile Ser Ser Leu Gln Pro Glu Asp Phe Ala Thr Tyr Tyr Cys
            210                 215                 220

Gln Gln Tyr Asp Ala Leu Pro Phe Thr Phe Gly Gln Gly Thr Lys Leu
225                 230                 235                 240

Glu Ile Lys Arg

<210> SEQ ID NO 51
<211> LENGTH: 247
<212> TYPE: PRT
<213> ORGANISM: Artificial Sequence
<220> FEATURE:
<223> OTHER INFORMATION: Synthetic polypeptide

<400> SEQUENCE: 51

Glu Val Gln Leu Val Gln Phe Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Gln Gln Ala Pro Gly Lys Gly Leu Glu Trp Met
            35                  40                  45

Gly Leu Val Asp Pro Glu Asp Gly Glu Thr Ile Tyr Ala Glu Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Pro Gly Gly Glu Gly Leu Gly Ala Ile Asp Gly Phe Asp
            100                 105                 110

Ile Trp Gly Gln Gly Thr Thr Val Thr Val Ser Ser Gly Gly Gly Gly
        115                 120                 125

Ser Gly Gly Gly Ala Ser Gly Gly Gly Ser Asp Ile Gln Met Thr
            130                 135                 140

Gln Ser Pro Ser Ser Leu Ser Ala Ser Val Gly Asp Arg Val Thr Ile
145                 150                 155                 160

Ala Cys Arg Ala Ser Gln Thr Ile Ser Arg Tyr Leu Asn Trp Tyr Gln
                165                 170                 175

Gln Lys Pro Gly Lys Ala Pro Lys Leu Leu Ile Tyr Ala Ala Ser Ser
            180                 185                 190

Leu Gln Ser Gly Val Ser Ser Arg Phe Ser Gly Ser Gly Ser Gly Thr
        195                 200                 205

Glu Phe Thr Leu Thr Ile Ser Ser Leu Gln Pro Glu Asp Phe Ala Thr
            210                 215                 220

Tyr Phe Cys Gln Gln Thr Tyr Ser Pro Pro Ile Thr Phe Gly Gln Gly
225                 230                 235                 240

Thr Arg Leu Glu Ile Lys Arg
                245

<210> SEQ ID NO 52
<211> LENGTH: 256
<212> TYPE: PRT
<213> ORGANISM: Artificial Sequence
<220> FEATURE:
<223> OTHER INFORMATION: Synthetic polypeptide
```

<400> SEQUENCE: 52

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Trp Pro Glu Tyr Ser Ser Ala Asp Ala Phe Asp Ile
            100                 105                 110

Trp Gly Gln Gly Thr Met Val Thr Val Ser Ser Gly Gly Gly Gly Ser
            115                 120                 125

Gly Gly Gly Ala Ser Gly Gly Gly Ser Asp Ile Gln Leu Thr Gln
        130                 135                 140

Ser Pro Ser Ser Leu Ser Ala Ser Val Gly Asp Arg Val Thr Ile Thr
145                 150                 155                 160

Cys Gln Ala Ser Gln Asp Ile Asp Asn Tyr Leu Asn Trp Phe Gln Gln
            165                 170                 175

Lys Pro Gly Lys Pro Lys Leu Leu Ile Ser Asp Ala Ser Ser Leu
            180                 185                 190

Glu Thr Gly Val Pro Ser Arg Phe Ser Gly Ser Gly Thr Asp
            195                 200                 205

Phe Thr Phe Thr Ile Ser Ser Leu Gln Pro Glu Asp Ile Ala Thr Tyr
            210                 215                 220

Tyr Cys Gln Gln Tyr Asp Asn Phe Pro Ile Thr Phe Gly Gln Gly Thr
225                 230                 235                 240

Lys Leu Glu Ile Lys Arg Gly Gln Ala Gly Gln Gly Pro Asp Lys Thr
            245                 250                 255

<210> SEQ ID NO 53
<211> LENGTH: 238
<212> TYPE: PRT
<213> ORGANISM: Artificial Sequence
<220> FEATURE:
<223> OTHER INFORMATION: Synthetic polypeptide

<400> SEQUENCE: 53

Glu Val Gln Leu Val Glu Ser Gly Gly Ala Leu Val Gln Pro Gly Gly
1               5                   10                  15

Ser Leu Arg Leu Ser Cys Ala Ser Gly Phe Thr Phe Thr Asn Tyr
            20                  25                  30

Gly Ile Ile Trp Val Arg Gln Ala Pro Gly Lys Gly Pro Glu Trp Val
        35                  40                  45

Ser Gly Val Ser Gly Asn Ala Val His Thr Tyr Tyr Ala Asp Ser Val
    50                  55                  60

Lys Gly Arg Phe Thr Ile Ser Arg Asp Asn Ser Lys Asn Met Val Tyr
65                  70                  75                  80

Leu Gln Met Asn Ser Leu Arg Ser Asp Asp Thr Ala Val Tyr Tyr Cys
                85                  90                  95

Ala Arg Gly Trp Asp Leu Asp Tyr Trp Gly Gln Gly Thr Leu Val Thr
            100                 105                 110

Val Ser Ser Gly Gly Gly Gly Ser Gly Gly Ala Ser Gly Gly Gly
        115                 120                 125

Gly Ser Glu Ile Val Leu Thr Gln Ser Pro Ser Ser Leu Ser Ala Ser
    130                 135                 140

Val Gly Asp Arg Val Thr Ile Thr Cys Gln Ala Ser Gln Asp Ile Ser
145                 150                 155                 160

Asn Tyr Leu Asn Trp Tyr Gln Gln Lys Pro Gly Lys Ala Pro Lys Leu
                165                 170                 175

Leu Ile Tyr Asp Ala Ser Asn Leu Glu Thr Gly Val Pro Ser Arg Phe
            180                 185                 190

Ile Gly Gly Gly Ser Gly Thr Asp Phe Thr Leu Thr Ile Ser Ser Leu
        195                 200                 205

Gln Pro Glu Asp Phe Ala Thr Tyr Tyr Cys Gln Gln His Asp Ser Leu
    210                 215                 220

Pro Leu Ser Phe Gly Gly Gly Thr Lys Leu Glu Ile Lys Arg
225                 230                 235

<210> SEQ ID NO 54
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 54

Gln Leu Gln Leu Gln Glu Ser Gly Pro Gly Leu Val Lys Pro Ser Glu
1               5                   10                  15

Thr Leu Ser Leu Thr Cys Val Val Phe Asp Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Asn Tyr Ser Gly Asn Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Asn Leu Arg Ser Val Thr Ala Ala Asp Thr Ala Val Tyr Tyr Cys
                85                  90                  95

Ala Arg Ser Val Asp Thr Ala Pro Gly Phe Asp Tyr Trp Gly Gln Gly
            100                 105                 110

Thr Leu Val Thr Val Ser Ser Gly Gly Gly Gly Ser Gly Gly Gly Ala
        115                 120                 125

Ser Ser Gly Gly Gly Ser Asp Ile Gln Met Thr Gln Ser Pro Ser Phe
    130                 135                 140

Leu Ser Ala Ser Val Gly Asp Arg Val Thr Ile Thr Cys Arg Ala Ser
145                 150                 155                 160

Gln Gly Ile Ser Ser Tyr Leu Ala Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Tyr Cys Gln Gln
    210                 215                 220

Tyr Asp Asn Leu Pro Leu Thr Phe Gly Gly Gly Thr Lys Leu Asp Ile
225                 230                 235                 240

Lys Arg

<210> SEQ ID NO 55
<211> LENGTH: 244
<212> TYPE: PRT
<213> ORGANISM: Artificial Sequence
<220> FEATURE:
<223> OTHER INFORMATION: Synthetic polypeptide

<400> SEQUENCE: 55

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Arg Ala Val Ala Gly Pro Gly Ala Phe Asp Ile Trp Gly
            100                 105                 110

Gln Gly Thr Met Val Thr Val Ser Ser Gly Gly Gly Ser Gly Gly
        115                 120                 125

Gly Ala Ser Gly Gly Gly Ser Glu Ile Val Leu Thr Gln Ser Pro
    130                 135                 140

Ser Ser Leu Ser Ala Ser Val Gly Asp Arg Val Thr Ile Ala Cys Arg
145                 150                 155                 160

Ala Ser Gln Thr Ile Ser Arg Tyr Leu Asn Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Ser Ser Arg Phe Ser Gly Ser Gly Ser Gly Thr Glu Phe Thr
        195                 200                 205

Leu Thr Ile Ser Ser Leu Gln Pro Glu Asp Phe Ala Thr Tyr Phe Cys
    210                 215                 220

Gln Gln Thr Tyr Ser Pro Pro Ile Thr Phe Gly Gln Gly Thr Arg Leu
225                 230                 235                 240

Glu Ile Lys Arg

<210> SEQ ID NO 56
<211> LENGTH: 242
<212> TYPE: PRT
<213> ORGANISM: Artificial Sequence
<220> FEATURE:
<223> OTHER INFORMATION: Synthetic polypeptide

<400> SEQUENCE: 56

Gln Val Gln Leu Val Glu Thr Gly Gly Gly Val Val Gln Pro Gly Thr
1               5                   10                  15

Ser Leu Arg Leu Ser Cys Ala Gly Ser Gly Phe Thr Phe Ser Glu Ser
            20                  25                  30

Gly Met His Trp Val Arg Gln Ala Pro Gly Lys Gly Leu Glu Trp Met
            35                  40                  45

Ala Leu Ile Leu Asn Asp Gly Ile Ser Asn Phe Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Ser Leu Gly Gly Asn Gly Ala Phe Asp Ile Trp Gly Gln Gly
            100                 105                 110

Thr Met Val Thr Val Ser Ser Gly Gly Gly Ser Gly Gly Gly Gly Ala
            115                 120                 125

Ser Ser Gly Gly Gly Ser Asp Ile Gln Leu Thr Gln Ser Pro Ser Ser
        130                 135                 140

Leu Ser Ala Ser Val Gly Asp Arg Val Thr Ile Thr Cys Gln Ala Ser
145                 150                 155                 160

Gln Asp Ile Ser Asn Tyr Leu Asn Trp Tyr Gln Gln Lys Pro Gly Lys
                165                 170                 175

Ala Pro Lys Leu Leu Ile Tyr Asp Ala Ser Asn Leu Glu Ile Gly Val
            180                 185                 190

Pro Ser Arg Phe Ser Gly Ser Gly Ser Gly Thr Asp Phe Thr Phe Thr
        195                 200                 205

Ile Ser Ser Leu Gln Pro Glu Asp Ile Ala Thr Tyr Tyr Cys Gln Gln
    210                 215                 220

His Asp Asn Leu Pro Leu Ser Phe Gly Gly Gly Thr Lys Leu Asp Ile
225                 230                 235                 240

Lys Arg

<210> SEQ ID NO 57
<211> LENGTH: 67
<212> TYPE: PRT
<213> ORGANISM: Artificial Sequence
<220> FEATURE:
<223> OTHER INFORMATION: Synthetic polypeptide

<400> SEQUENCE: 57

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg
 65

<210> SEQ ID NO 58
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 58

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 59
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 59

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105

<210> SEQ ID NO 60
<211> LENGTH: 69
<212> TYPE: PRT
<213> ORGANISM: Artificial Sequence
<220> FEATURE:
<223> OTHER INFORMATION: Synthetic polypeptide

<400> SEQUENCE: 60

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 61
<211> LENGTH: 84
<212> TYPE: PRT
<213> ORGANISM: Artificial Sequence
<220> FEATURE:
<223> OTHER INFORMATION: Synthetic polypeptide -continued

```
<400> SEQUENCE: 61

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 62
<211> LENGTH: 42
<212> TYPE: PRT
<213> ORGANISM: Artificial Sequence
<220> FEATURE:
<223> OTHER INFORMATION: Synthetic polypeptide

<400> SEQUENCE: 62

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 63
<211> LENGTH: 47
<212> TYPE: PRT
<213> ORGANISM: Artificial Sequence
<220> FEATURE:
<223> OTHER INFORMATION: Synthetic polypeptide

<400> SEQUENCE: 63

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30

Cys Ser Cys Arg Phe Pro Glu Glu Glu Glu Gly Gly Cys Glu Leu
        35                  40                  45

<210> SEQ ID NO 64
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 64

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60
```

-continued

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 65
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 65

Ala Ala Ala Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
            100                 105                 110

Lys Phe Ser Arg Ser Ala Asp Ala Pro Ala Tyr Gln Gln Gly Gln Asn
        115                 120                 125

Gln Leu Tyr Asn Glu Leu Asn Leu Gly Arg Arg Glu Glu Tyr Asp Val
    130                 135                 140

Leu Asp Lys Arg Arg Gly Arg Asp Pro Glu Met Gly Gly Lys Pro Arg
145                 150                 155                 160

Arg Lys Asn Pro Gln Glu Gly Leu Tyr Asn Glu Leu Gln Lys Asp Lys
                165                 170                 175

Met Ala Glu Ala Tyr Ser Glu Ile Gly Met Lys Gly Glu Arg Arg Arg
            180                 185                 190

Gly Lys Gly His Asp Gly Leu Tyr Gln Gly Leu Ser Thr Ala Thr Lys
        195                 200                 205

Asp Thr Tyr Asp Ala Leu His Met Gln Ala Leu Pro Pro Arg
    210                 215                 220

<210> SEQ ID NO 66
<211> LENGTH: 226
<212> TYPE: PRT
<213> ORGANISM: Artificial Sequence
<220> FEATURE:
<223> OTHER INFORMATION: Synthetic polypeptide

<400> SEQUENCE: 66

Ala Ala Ala Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45

```
Ile Tyr Ile Trp Ala Pro Leu Ala Gly Thr Cys Gly Val Leu Leu Leu
 50                  55                  60

Ser Leu Val Ile Thr Leu Tyr Cys Lys Arg Gly Arg Lys Lys Leu Leu
 65                  70                  75                  80

Tyr Ile Phe Lys Gln Pro Phe Met Arg Pro Val Gln Thr Thr Gln Glu
                 85                  90                  95

Glu Asp Gly Cys Ser Cys Arg Phe Pro Glu Glu Glu Glu Gly Gly Cys
            100                 105                 110

Glu Leu Arg Val Lys Phe Ser Arg Ser Ala Asp Ala Pro Ala Tyr Lys
        115                 120                 125

Gln Gly Gln Asn Gln Leu Tyr Asn Glu Leu Asn Leu Gly Arg Arg Glu
    130                 135                 140

Glu Tyr Asp Val Leu Asp Lys Arg Arg Gly Arg Asp Pro Glu Met Gly
145                 150                 155                 160

Gly Lys Pro Arg Arg Lys Asn Pro Gln Glu Gly Leu Tyr Asn Glu Leu
                165                 170                 175

Gln Lys Asp Lys Met Ala Glu Ala Tyr Ser Glu Ile Gly Met Lys Gly
            180                 185                 190

Glu Arg Arg Arg Gly Lys Gly His Asp Gly Leu Tyr Gln Gly Leu Ser
        195                 200                 205

Thr Ala Thr Lys Asp Thr Tyr Asp Ala Leu His Met Gln Ala Leu Pro
    210                 215                 220

Pro Arg
225

<210> SEQ ID NO 67
<211> LENGTH: 286
<212> TYPE: PRT
<213> ORGANISM: Artificial Sequence
<220> FEATURE:
<223> OTHER INFORMATION: Synthetic polypeptide

<400> SEQUENCE: 67

Ala Ala Ala Phe Val Pro Val Phe Leu Pro Ala Lys Pro Thr Thr Thr
  1               5                  10                  15

Pro Ala Pro Arg Pro Pro Thr Pro Ala Pro Thr Ile Ala Ser Gln Pro
                 20                  25                  30

Leu Ser Leu Arg Pro Glu Ala Cys Arg Pro Ala Ala Gly Gly Ala Val
            35                  40                  45

His Thr Arg Gly Leu Asp Phe Ala Cys Asp Ile Tyr Ile Trp Ala Pro
        50                  55                  60

Leu Ala Gly Thr Cys Gly Val Leu Leu Leu Ser Leu Val Ile Thr Leu
 65                  70                  75                  80

Tyr Cys Asn His Arg Asn Arg Ser Lys Arg Ser Arg Leu Leu His Ser
                 85                  90                  95

Asp Tyr Met Asn Met Thr Pro Arg Arg Pro Gly Pro Thr Arg Lys His
            100                 105                 110

Tyr Gln Pro Tyr Ala Pro Pro Arg Asp Phe Ala Ala Tyr Arg Ser Arg
        115                 120                 125

Phe Ser Val Val Lys Arg Gly Arg Lys Lys Leu Leu Tyr Ile Phe Lys
    130                 135                 140

Gln Pro Phe Met Arg Pro Val Gln Thr Thr Gln Glu Glu Asp Gly Cys
145                 150                 155                 160

Ser Cys Arg Phe Pro Glu Glu Glu Glu Gly Gly Cys Glu Leu Arg Val
                165                 170                 175
```

```
Lys Phe Ser Arg Ser Ala Asp Ala Pro Ala Tyr Gln Gln Gly Gln Asn
                180                 185                 190

Gln Leu Tyr Asn Glu Leu Asn Leu Gly Arg Arg Glu Glu Tyr Asp Val
            195                 200                 205

Leu Asp Lys Arg Arg Gly Arg Asp Pro Glu Met Gly Gly Lys Pro Arg
        210                 215                 220

Arg Lys Asn Pro Gln Glu Gly Leu Tyr Asn Glu Leu Gln Lys Asp Lys
225                 230                 235                 240

Met Ala Glu Ala Tyr Ser Glu Ile Gly Met Lys Gly Glu Arg Arg Arg
                245                 250                 255

Gly Lys Gly His Asp Gly Leu Tyr Gln Gly Leu Ser Thr Ala Thr Lys
            260                 265                 270

Asp Thr Tyr Asp Ala Leu His Met Gln Ala Leu Pro Pro Arg
        275                 280                 285

<210> SEQ ID NO 68
<211> LENGTH: 500
<212> TYPE: PRT
<213> ORGANISM: Artificial Sequence
<220> FEATURE:
<223> OTHER INFORMATION: Synthetic polypeptide

<400> SEQUENCE: 68

Leu Leu Val Thr Ser Leu Leu Cys Glu Leu Pro His Pro Ala Phe
1               5                   10                  15

Leu Leu Ile Pro Asp Thr Glu Leu Val Leu Thr Gln Thr Pro Ser Ser
                20                  25                  30

Val Ser Ala Ala Val Gly Gly Thr Val Thr Ile Asn Cys Gln Ser Ser
            35                  40                  45

Pro Ser Leu Tyr Lys Asn Asn Tyr Leu Ser Trp Tyr Gln Gln Lys Pro
        50                  55                  60

Gly Gln Pro Pro Lys Leu Leu Ile Tyr Ser Ala Ser Thr Leu Ala Ser
65                  70                  75                  80

Gly Val Pro Ser Arg Phe Lys Gly Ser Gly Ser Gly Thr Glu Tyr Thr
                85                  90                  95

Leu Thr Ile Ser Gly Val Gln Cys Asp Asp Ala Ala Thr Tyr Tyr Cys
            100                 105                 110

Leu Gly Gly Tyr Ser Leu Ser Ser Asp Ser Pro Arg Ala Phe Gly Gly
        115                 120                 125

Gly Thr Glu Val Val Val Lys Gly Gly Gly Gly Ser Gly Gly Gly Gly
    130                 135                 140

Ser Gly Gly Gly Gly Ser Gln Ser Val Lys Glu Ser Glu Gly Arg Leu
145                 150                 155                 160

Val Thr Pro Gly Thr Pro Leu Thr Leu Thr Cys Thr Val Ser Gly Phe
                165                 170                 175

Ser Leu Ser Ser Asn Ser Val Gly Trp Val Arg Gln Ala Pro Gly Lys
            180                 185                 190

Gly Leu Glu Trp Ile Gly Ile Ile Ser Ser Ser Gly Asn Arg Tyr Tyr
        195                 200                 205

Ala Ser Trp Ala Lys Gly Arg Phe Thr Ile Ser Lys Thr Ser Thr Thr
    210                 215                 220

Val Asp Leu Lys Ile Thr Ser Pro Thr Thr Glu Asp Thr Ala Thr Tyr
225                 230                 235                 240

Phe Cys Gly Gly Asp Pro Val Ser Trp Tyr Gly Asp Ile Trp Gly Pro
                245                 250                 255
```

```
Gly Thr Leu Val Thr Val Ser Ser Glu Pro Lys Ser Cys Asp Lys Thr
                260                 265                 270

His Thr Cys Pro Pro Cys Pro Ala Pro Glu Leu Leu Gly Gly Pro Ser
            275                 280                 285

Val Phe Leu Phe Pro Pro Lys Pro Lys Asp Thr Leu Met Ile Ser Arg
        290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
                405                 410                 415

Leu Val Lys Gly Phe Tyr Pro Ser Asp Ile Ala Val Glu Trp Glu Ser
            420                 425                 430

Asn Gly Gln Pro Glu Asn Asn Tyr Lys Thr Thr Pro Pro Val Leu Asp
        435                 440                 445

Ser Asp Gly Ser Phe Phe Leu Tyr Ser Lys Leu Thr Val Asp Lys Ser
    450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
                485                 490                 495

Lys Asp Pro Lys
            500

<210> SEQ ID NO 69
<211> LENGTH: 279
<212> TYPE: PRT
<213> ORGANISM: Artificial Sequence
<220> FEATURE:
<223> OTHER INFORMATION: Synthetic polypeptide

<400> SEQUENCE: 69

Leu Leu Val Thr Ser Leu Leu Cys Glu Leu Pro His Pro Ala Phe
1               5                   10                  15

Leu Leu Ile Pro Asp Thr Glu Leu Val Leu Thr Gln Thr Pro Ser Ser
                20                  25                  30

Val Ser Ala Ala Val Gly Gly Thr Val Thr Ile Asn Cys Gln Ser Ser
            35                  40                  45

Pro Ser Leu Tyr Lys Asn Asn Tyr Leu Ser Trp Tyr Gln Gln Lys Pro
        50                  55                  60

Gly Gln Pro Pro Lys Leu Leu Ile Tyr Ser Ala Ser Thr Leu Ala Ser
65                  70                  75                  80

Gly Val Pro Ser Arg Phe Lys Gly Ser Gly Ser Gly Thr Glu Tyr Thr
                85                  90                  95

Leu Thr Ile Ser Gly Val Gln Cys Asp Asp Ala Ala Thr Tyr Tyr Cys
            100                 105                 110
```

```
Leu Gly Gly Tyr Ser Leu Ser Ser Asp Ser Pro Arg Ala Phe Gly Gly
            115                 120                 125

Gly Thr Glu Val Val Lys Gly Gly Gly Ser Gly Gly Gly
        130                 135                 140

Ser Gly Gly Gly Ser Gln Ser Val Lys Glu Ser Glu Gly Arg Leu
145                 150                 155                 160

Val Thr Pro Gly Thr Pro Leu Thr Leu Thr Cys Thr Val Ser Gly Phe
                165                 170                 175

Ser Leu Ser Ser Asn Ser Val Gly Trp Val Arg Gln Ala Pro Gly Lys
            180                 185                 190

Gly Leu Glu Trp Ile Gly Ile Ile Ser Ser Ser Gly Asn Arg Tyr Tyr
        195                 200                 205

Ala Ser Trp Ala Lys Gly Arg Phe Thr Ile Ser Lys Thr Ser Thr Thr
    210                 215                 220

Val Asp Leu Lys Ile Thr Ser Pro Thr Thr Glu Asp Thr Ala Thr Tyr
225                 230                 235                 240

Phe Cys Gly Gly Asp Pro Val Ser Trp Tyr Gly Asp Ile Trp Gly Pro
                245                 250                 255

Gly Thr Leu Val Thr Val Ser Ser Lys Thr Thr Pro Pro Ser Val Tyr
            260                 265                 270

Gly Arg Val Lys Asp Pro Lys
        275

<210> SEQ ID NO 70
<211> LENGTH: 503
<212> TYPE: PRT
<213> ORGANISM: Artificial Sequence
<220> FEATURE:
<223> OTHER INFORMATION: Synthetic polypeptide

<400> SEQUENCE: 70

Leu Leu Val Thr Ser Leu Leu Leu Cys Glu Leu Pro His Pro Ala Phe
1               5                   10                  15

Leu Leu Ile Pro Asp Thr Glu Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

Gln Ser Ile Ser Ser Ser Tyr Leu Ser Trp Tyr Gln Gln Lys Pro Gly
    50                  55                  60

Gln Pro Pro Lys Leu Leu Ile Tyr Lys Ala Ser Thr Arg Pro Ser Gly
65                  70                  75                  80

Val Ser Ser Arg Phe Lys Gly Ser Gly Ser Gly Thr Gln Phe Thr Leu
                85                  90                  95

Thr Ile Ser Gly Val Gln Cys Ala Asp Ala Ala Thr Tyr Tyr Cys Leu
            100                 105                 110

Tyr Gly Tyr Tyr Ile Asp Ser Gly Ala Asp Asn Ser Phe Gly Gly Gly
        115                 120                 125

Thr Glu Val Val Val Lys Gly Gly Gly Gly Ser Gly Gly Gly Gly Ser
    130                 135                 140

Gly Gly Gly Gly Ser Gln Ser Val Lys Glu Ser Glu Gly Arg Leu Val
145                 150                 155                 160

Thr Pro Gly Thr Pro Leu Thr Leu Thr Cys Thr Val Ser Gly Phe Ser
                165                 170                 175

Leu Ser Thr Tyr Ala Met Ser Trp Val Arg Gln Ala Pro Glu Lys Gly
            180                 185                 190
```

Leu Glu Trp Ile Gly Ile Ile Tyr Ala Thr Ala Glu Thr Tyr Ala
            195                 200                 205

Thr Trp Ala Arg Gly Arg Phe Thr Ile Ser Lys Thr Ser Thr Thr Val
    210                 215                 220

Asp Leu Lys Ile Thr Ser Pro Ala Thr Glu Asp Thr Ala Thr Tyr Phe
225                 230                 235                 240

Cys Ala Arg Leu Asn Gly Asp Gly Ser Gly Thr Tyr Ala Tyr Asp Ile
                245                 250                 255

Trp Gly Pro Gly Thr Leu Val Thr Val Ser Ser Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
    370                 375                 380

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
                405                 410                 415

Leu Thr Cys Leu Val Lys Gly Phe Tyr Pro Ser Asp Ile Ala Val Glu
            420                 425                 430

Trp Glu Ser Asn Gly Gln Pro Glu Asn Asn Tyr Lys Thr Thr Pro Pro
        435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Lys Asp Pro Lys
            500

<210> SEQ ID NO 71
<211> LENGTH: 282
<212> TYPE: PRT
<213> ORGANISM: Artificial Sequence
<220> FEATURE:
<223> OTHER INFORMATION: Synthetic polypeptide

<400> SEQUENCE: 71

Leu Leu Val Thr Ser Leu Leu Cys Glu Leu Pro His Pro Ala Phe
1               5                   10                  15

Leu Leu Ile Pro Asp Thr Glu Leu Val Met Thr Gln Thr Pro Ser Pro
            20                  25                  30

Val Ser Ala Ala Val Gly Gly Thr Val Thr Ile Asn Cys Gln Ala Ser
        35                  40                  45

-continued

```
Gln Ser Ile Ser Ser Tyr Leu Ser Trp Tyr Gln Gln Lys Pro Gly
 50                  55                  60

Gln Pro Pro Lys Leu Leu Ile Tyr Lys Ala Ser Thr Arg Pro Ser Gly
 65              70                  75                      80

Val Ser Ser Arg Phe Lys Gly Ser Gly Ser Gly Thr Gln Phe Thr Leu
             85                  90                  95

Thr Ile Ser Gly Val Gln Cys Ala Asp Ala Ala Thr Tyr Tyr Cys Leu
             100             105                 110

Tyr Gly Tyr Tyr Ile Asp Ser Gly Ala Asp Asn Ser Phe Gly Gly Gly
         115             120                 125

Thr Glu Val Val Val Lys Gly Gly Gly Gly Ser Gly Gly Gly Gly Ser
 130                 135                 140

Gly Gly Gly Gly Ser Gln Ser Val Lys Glu Ser Glu Gly Arg Leu Val
 145             150                 155                     160

Thr Pro Gly Thr Pro Leu Thr Leu Thr Cys Thr Val Ser Gly Phe Ser
             165                 170                 175

Leu Ser Thr Tyr Ala Met Ser Trp Val Arg Gln Ala Pro Glu Lys Gly
             180                 185                 190

Leu Glu Trp Ile Gly Ile Ile Tyr Ala Thr Ala Glu Thr Tyr Tyr Ala
             195             200                 205

Thr Trp Ala Arg Gly Arg Phe Thr Ile Ser Lys Thr Ser Thr Thr Val
 210                 215                 220

Asp Leu Lys Ile Thr Ser Pro Ala Thr Glu Asp Thr Ala Thr Tyr Phe
 225                 230                 235                 240

Cys Ala Arg Leu Asn Gly Asp Gly Ser Gly Thr Tyr Ala Tyr Asp Ile
             245                 250                 255

Trp Gly Pro Gly Thr Leu Val Thr Val Ser Ser Lys Thr Thr Pro Pro
             260                 265                 270

Ser Val Tyr Gly Arg Val Lys Asp Pro Lys
             275                 280
```